(12) United States Patent
Littman et al.

(10) Patent No.: US 9,765,063 B2
(45) Date of Patent: *Sep. 19, 2017

(54) AMIDO COMPOUNDS AS RORγT MODULATORS AND USES THEREOF

(75) Inventors: Dan Littman, New York, NY (US); Jun R. Huh, New York, NY (US); Ruili Huang, Rockville, MD (US); Wenwei Huang, Rockville, MD (US); Erika E. Englund, Washington, DC (US)

(73) Assignees: New York University, New York, NY (US); The United States of America, as Represented by the Secretary, Department of Health and Human Services, Washington, DC (US)

( * ) Notice: Subject to any disclaimer, the term of this patent is extended or adjusted under 35 U.S.C. 154(b) by 240 days.

This patent is subject to a terminal disclaimer.

(21) Appl. No.: 14/343,410

(22) PCT Filed: Sep. 10, 2012

(86) PCT No.: PCT/US2012/054424
§ 371 (c)(1),
(2), (4) Date: Oct. 14, 2014

(87) PCT Pub. No.: WO2013/036912
PCT Pub. Date: Mar. 14, 2013

(65) Prior Publication Data
US 2015/0057278 A1    Feb. 26, 2015

Related U.S. Application Data

(60) Provisional application No. 61/573,635, filed on Sep. 9, 2011.

(51) Int. Cl.
| | | |
|---|---|---|
| C07D 409/06 | (2006.01) | |
| C07D 209/44 | (2006.01) | |
| C07D 211/14 | (2006.01) | |
| C07D 213/58 | (2006.01) | |
| C07D 333/24 | (2006.01) | |
| C07D 401/06 | (2006.01) | |
| C07D 405/14 | (2006.01) | |
| A61K 31/40 | (2006.01) | |
| A61K 31/4025 | (2006.01) | |
| A61K 31/445 | (2006.01) | |
| A61K 31/4709 | (2006.01) | |
| A61K 31/495 | (2006.01) | |
| A61K 31/496 | (2006.01) | |
| A61K 31/5375 | (2006.01) | |
| A61K 31/5377 | (2006.01) | |

(52) U.S. Cl.
CPC ........... *C07D 409/06* (2013.01); *A61K 31/40* (2013.01); *A61K 31/4025* (2013.01); *A61K 31/445* (2013.01); *A61K 31/4709* (2013.01); *A61K 31/495* (2013.01); *A61K 31/496* (2013.01); *A61K 31/5375* (2013.01); *A61K 31/5377* (2013.01); *C07D 209/44* (2013.01); *C07D 211/14* (2013.01); *C07D 213/58* (2013.01); *C07D 333/24* (2013.01); *C07D 401/06* (2013.01); *C07D 405/14* (2013.01)

(58) Field of Classification Search
CPC .. C07D 409/06; C07D 209/44; C07D 211/14; C07D 213/58; C07D 333/24; C07D 401/06; C07D 405/14

See application file for complete search history.

(56) References Cited

U.S. PATENT DOCUMENTS

| 4,086,227 A | 4/1978 | Adelstein et al. |
|---|---|---|
| 2004/0147529 A1 | 7/2004 | Snutch et al. |

FOREIGN PATENT DOCUMENTS

| EP | 2181710 | 5/2010 |
|---|---|---|
| WO | 2008031227 | 3/2008 |
| WO | 2011112263 | 9/2011 |

OTHER PUBLICATIONS

Wang et al., "A second class of nuclear receptors for oxysterols: Regulations of RORalpha and RORgamma activity by 24S-hydroxycholesterol (cerebrosterol)", Biochim Biophys Acta, 2010, 1801, 917-823.

*Primary Examiner* — Rebecca Anderson
(74) *Attorney, Agent, or Firm* — Klauber & Jackson LLC

(57) ABSTRACT

Amido compounds are disclosed that have a formula represented by the following:

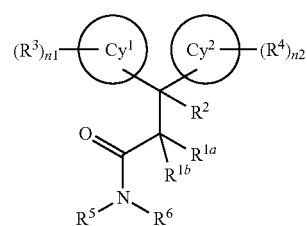

and wherein $Cy^1$, $Cy^2$, n1, n2, $R^{1a}$, $R^{1b}$, $R^2$, $R^3$, $R^4$, $R^5$, and $R^6$ are as described herein. The compounds may be prepared as pharmaceutical compositions, and may be used for the prevention and treatment of a variety of conditions in mammals including humans, including by way of non-limiting example, inflammatory conditions, autoimmune disorders, cancer, and graft-versus-host disease.

13 Claims, 3 Drawing Sheets

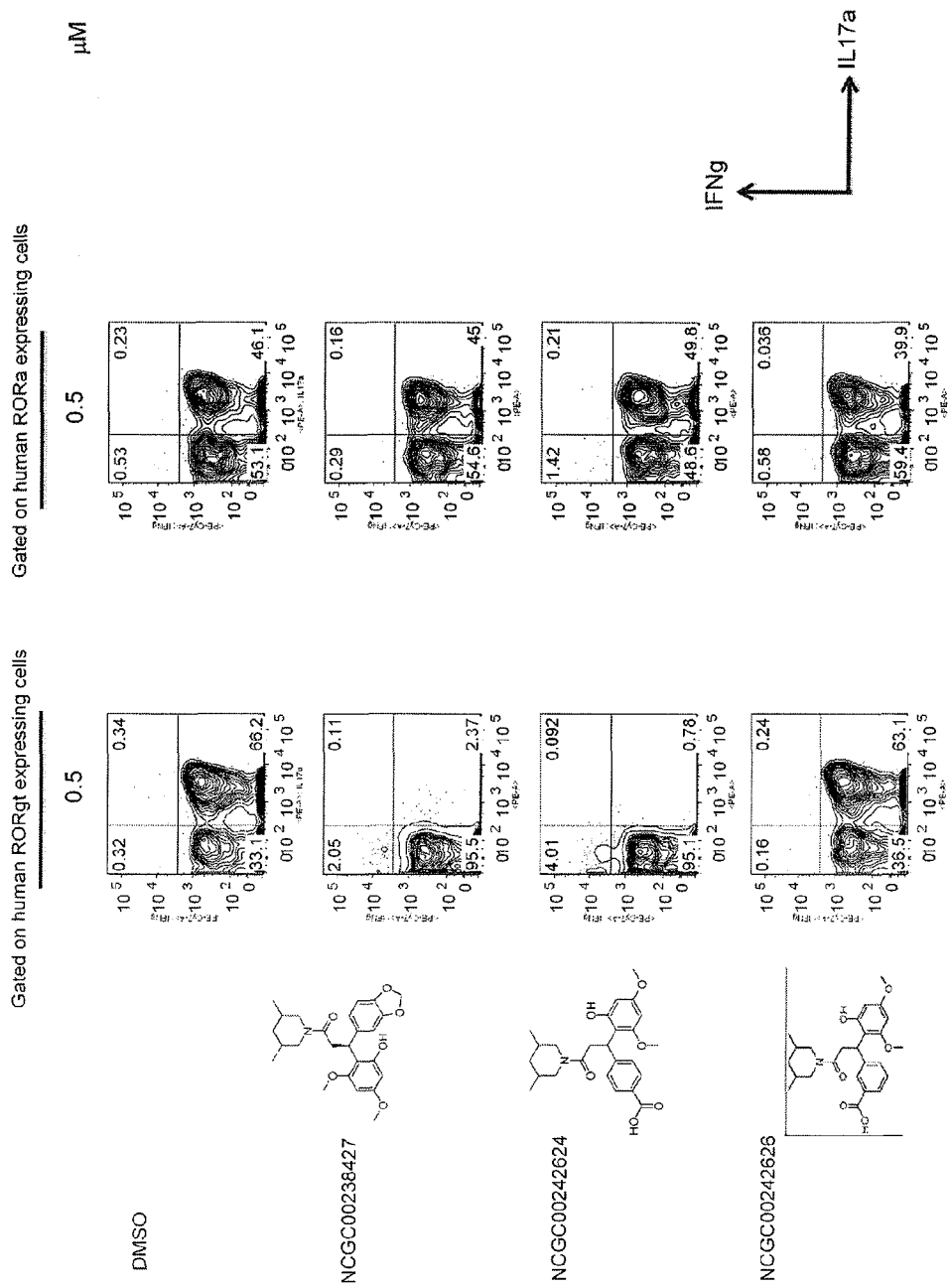

AMIDO COMPOUNDS AS RORγT MODULATORS AND USES THEREOF

CROSS REFERENCE TO RELATED APPLICATIONS

The present application is a National Stage Application which claims priority under 35 U.S.C. §120 from co-pending PCT Application No. PCT/US2012/054424 filed Sep. 10, 2012, which in turn claims priority from 35 U.S.C. §119(e) from U.S. Provisional Application Ser. No. 61/573,635, filed Sep. 9, 2011.

"This invention was made with government support under Grant Number R01A1080885 awarded by the National Institutes of Health. The Government has certain rights in the invention."

FIELD OF THE INVENTION

This invention relates to amido compounds capable of modulating RORγt activity and uses of such compounds to treat diseases or conditions related to RORγt activity. More particularly, the amido compounds may be used to diminish inflammation associated with an inflammatory disease or condition or to reduce symptoms associated with an autoimmune disorder. Also encompassed herein, are compositions of amido compounds, pharmaceutical compositions of amido compounds, assays and methods for using same to identify compounds capable of modulating RORγt activity.

BACKGROUND OF THE INVENTION

The retinoic acid receptor-related orphan nuclear receptor (ROR) RORγ and its isoform RORγt (collectively "RORγ/γt") play a major role in regulation of a variety of biological systems. To illustrate, RORγt has a central role in immune system development, homeostasis, and responses to microbial pathogens. For example, RORγt is required for the differentiation of Th17 cells (Tvanov, I I et al. *Cell*, 2006, 126, 1121-33), a subset of T helper cells that protect the host from infection by secreting inflammatory cytokines such as IL-17, IL-17 (also called IL-17A), TL-17F, TL-22, and TNFα. These cytokines are signaling proteins that have been shown to be essential in regulating numerous immune responses, including inflammatory responses to antigens. Th17 cells have also recently been shown to have important roles in activating and directing immune responses in a variety of autoimmune diseases, such as experimental autoimmune encephalomyelitis (EAE), collagen-induced arthritis (CIA), inflammatory bowel disease (IBD), cancer (Weaver, C. et al. *Ann. Rev. Immunol.*, 2007, 25, 821-52; Krvczek, I. et al. *J. Immunol.*, 2007, 178, 6730-3; Cua, D. J. et al. *Nature.* 2003, 421, 744-8; Langrish, C. L. et al. *J. Exp. Med.*, 2005, 201, 233-40; Yen. D. et al. *J. Clin. Invest.*, 2006, 116, 1310-6), and graft-versus-host disease (Carlson, M. J. et al. *Blood*, 28 Oct. 2008. [Epub ahead of print]; Kappel, L. W. et al. *Blood*, 17 Oct. 2008. [Epub ahead of print]). Th17 cells have also been implicated in asthma, psoriasis, rheumatoid arthritis, multiple sclerosis (Tzartos, J. S., et al. *Am. J. Pathology*, 2008, 172, 146-55; Yu, J. J., and Gaffen, S. L. *Front. Biosci.*, 2008, 13, 170-77; and Zheng, Y. et al. *Nature*, 2007, 445, 648-51), and Crohn's disease (Duerr, R. H., et al. *Science*, 2006, 314, 1461-63). Additionally, it has been shown that mice defective for expression of RORγt lack Th17 cells and are resistant to a variety of autoimmune diseases and that the absence of Th17-producing microbiota in the small intestine of mice alters the Th17: regulatory T (Treg) cell balance with implications for intestinal immunity, tolerance, and susceptibility to inflammatory bowel diseases (Ivanov, I. I. *Cell Host & Microbe*, 2008, 4, 337-49).

The formation of immune cell aggregates, such as cryptopatches (CP) and isolated lymphoid follicles (ILF), which contain RORγt expressing cells, is known to be a vital step in many immune responses. For example, CPs and ILFs are required for mucosal immunity and for production of the intestinal antibody IgA. Such immune responses can result in inflammation in various diseases, such as Crohn's disease. The ability to inhibit such immune responses by inhibiting the formation of immune cell aggregates may offer another way to treat diseases associated with such responses.

T-cells have also been demonstrated to play a role in diseases characterized by bone loss and degradation, such as osteoarthritis. For example, in autoimmune arthritis, activation of T cells results in bone destruction mediated by osteoclasts. Th17, whose differentiation is regulated by RORγt, has been shown to be osteoclastogenic, thus linking T cell activation and bone resorption (Sato, K. et al. *J. Ex. Med.*, 2008, 203, 2673-82). Thus, the ability to regulate Th17 cell differentiation via RORγt modulation may offer a way to treat bone loss and degradation, such as that associated with autoimmune disease. Furthermore, interferon gamma (IFN-γ) suppresses osteoclast formation by rapidly degrading the RANK adaptor protein TRAF6 in the RANK-RANKL signaling pathway, and RORγt has been shown to down-regulate the production of IFN-γ (Ivanov, I. I. et al. *Cell*, 2006, 126, 1121-33). Thus, the ability to regulate osteoclast formation through modulation of RORγt-mediated IFN-γ osteoclast suppression may provide additional methods to treat bone loss and degradation, such as that associated with autoimmune disease (e.g., osteoarthritis).

Circadian rhythm relates to an approximately daily periodicity in the biochemical, physiological or behavioral processes of living beings, including plants, animals, fungi and some bacteria. Members of the ROR family of orphan nuclear receptors have been implicated in regulation of control of circadian clock function by regulation of clock genes (Ueda, H. R. et al. *Nature*, 2002, 418, 534-39; Sato, T. K. et al. *Neuron*, 2004, 43, 527-37), and RORγ/γt has been implicated in the regulation of genes that govern circadian metabolism (Kumaki, Y. et al. *PNAS*, 2008, 105, 14946-51; Liu, C. et al. *Nature*, 2007, 447, 477-81). Moreover, RORγ gene expression is known to oscillate in a circadian manner in metabolically active tissues such as liver and brown adipose tissue (Yang, X. et al., *Cell*, 2006, 126, 801-10), which further confirms that a role exists for RORγ in regulating circadian function. Hence, the ability to modulate RORγ/γt expression may also result in circadian rhythm regulation and treatment of disorders associated with disruption of circadian rhythm. Since circadian rhythm is integral in maintaining metabolic levels, whose imbalance is linked to obesity and diabetes, modulators of RORγ/γt may also be useful in treating obesity and diabetes through regulation of circadian rhythm.

WO2011/112263 discloses diphenyl substituted amino compounds as RORγ/γt modulators. WO2011/112264 discloses a series of compounds as RORγ/γt modulators.

In view of the above, a need exists for therapeutic agents, and corresponding pharmaceutical compositions and related methods of treatment that address conditions causally related to RORγt activity, and it is toward the fulfillment and satisfaction of that need, that the present invention is directed.

SUMMARY OF THE INVENTION

The present invention provides a method for preventing, treating or ameliorating in a mammal a disease or condition that is causally related to RORγ or RORγt activity in vivo, which comprises administering to the mammal an effective disease-treating or condition-treating amount of a compound according to formula I:

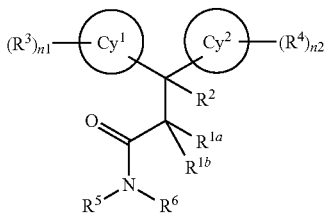

wherein
each $Cy^1$ and $Cy^2$ is independently selected from substituted or unsubstituted aryl and heteroaryl;
each n1 and n2 is independently 1, 2, 3, 4 or 5;
each $R^{1a}$ and $R^{1b}$ is independently H, substituted or unsubstituted $C_1$-$C_6$ alkyl, or CN; or
$R^{1a}$ and $R^{1b}$ joined together to form cycloalkyl ring;
$R^2$ is H, substituted or unsubstituted $C_1$-$C_6$ alkyl, or aryl;
or one of $R^{1a}$ and $R^{1b}$ is joined to the C of $CR^2$ to form a cyclopropyl ring; or $R^2$ is joined to the C of $CR^{1a}R^{1b}$ to form a cyclopropyl ring;
each $R^3$ and $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfonyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol; or any two adjacent $R^3$ groups, or any two adjacent $R^4$ groups may join together to form a substituted or unsubstituted carbocyclic or heterocyclic ring;
each $R^5$ and $R^6$ is independently selected from H, substituted or unsubstituted alkyl, substituted or unsubstituted cycloalkyl, substituted or unsubstituted aryl, substituted or unsubstituted heteroaryl, substituted or unsubstituted aralkyl, and substituted or unsubstituted heteroaryl alkyl; or
$R^5$ and $R^6$, together with the N they are attached to, form a 4-12 membered substituted or unsubstituted heterocycloalkyl;
provided that
i) at least one of $Cy^1$ and $Cy^2$ is heteroaryl; or
ii) when each of $Cy^1$ and $Cy^2$ is phenyl; then at least one $R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl;
and wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;
or a pharmaceutically acceptable salt, solvate or prodrug thereof;
or stereoisomers, isotopic variants and tautomers thereof.

In one embodiment, with respect to the compounds of formula I, $R^5$ and $R^6$ are joined together to form substituted or unsubstituted azetidinyl, pyrrolidinyl, piperidinyl, piperizinyl, morpholinyl, tetrahydroquinolinyl, indolinyl, or azepinyl. In another embodiment. $R^5$ and $R^6$ are joined together to form unsubstituted pyrrolidinyl, piperidinyl, piperizinyl, morpholinyl, or azepinyl. In a particular embodiment, $R^5$ and $R^6$ are joined together to form piperidinyl or piperizinyl.

In a further aspect, the present invention provides a compound according to formula IIIa-IIIc:

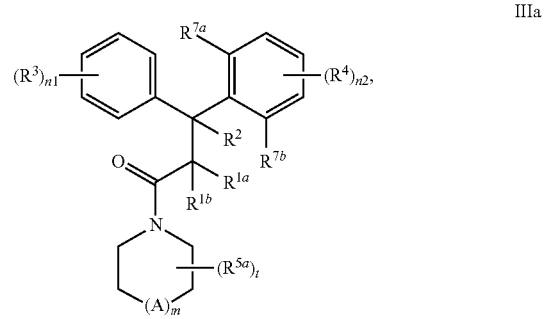

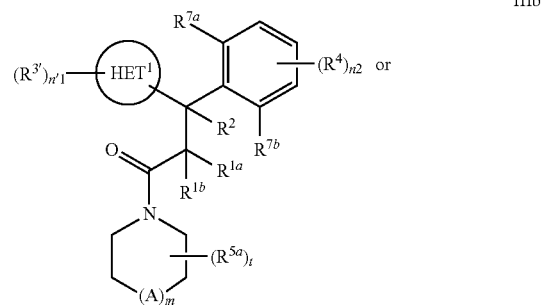

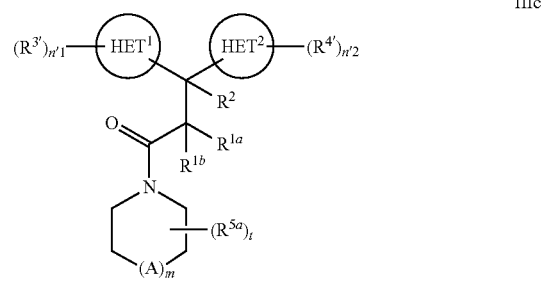

and wherein n1, $R^{1a}$, $R^{1b}$, $R^2$, $R^3$, and $R^4$, are as described for formula I; n2 is 1, 2, or 3;
each $HET^1$ and $HET^2$ is independently selected from heteroaryl;
$R^{3'}$ is $R^3$; $R^{4'}$ is $R^4$; n'1 is n1; n'2 is n2;
A is $CR^{8a}R^{8b}$, $NR^{8a}$, O, or S; m is 0 or 1;

each $R^{5a}$ is alkyl, substituted alkyl, halo, haloalkyl, hydroxyalkyl, aryl, heteroaryl, CN, alkoxyalkyl, amido, hydroxyl, alkoxy or substituted alkoxy; and t is 0, 1, 2, or 3;

$R^{7a}$ is OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thio;

$R^{7b}$ is $R^4$; or any two adjacent $R^4$ and $R^{7b}$ groups may join together to form a substituted or unsubstituted carbocyclic or heterocyclic ring; and each $R^{8a}$ and $R^{8b}$ is independently H, substituted or unsubstituted $C_1$-$C_6$ alkyl, substituted or unsubstituted aryl, or substituted or unsubstituted heteroaryl;

or a pharmaceutically acceptable salt, solvate or prodrug thereof;

or stereoisomers, isotopic variants and tautomers thereof;

provided that
i) when the compound is according to formula IIIa, then at least one $R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl; and wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;
ii) when the compound is according to formula IIIa, $R^3$ is $CONR^{3a}R^{3b}$, $R^{3a}$ and $R^{3b}$ are joined together to form a morpholino ring, m is 1, and A is O; then $R^{7a}$ is other than H;
iii) when the compound is

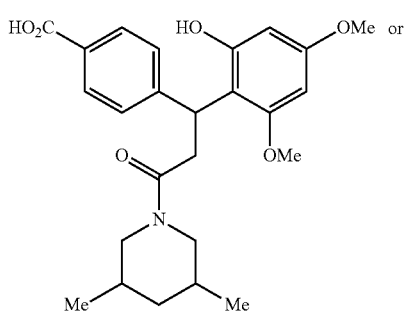

Compound 99

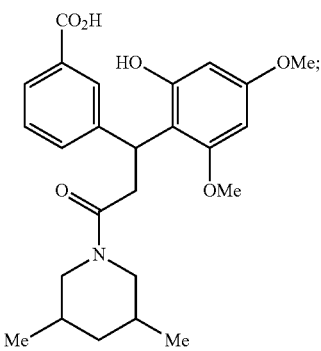

Compound 101 then the compound is in the form of a sodium, potassium, calcium, or ammonium salt;
iv) the compound is other than the compounds listed in Table 1, wherein compound ID is 83, 84, 95, 100, 111, and 139;
v) when the compound is according to formula IIIb; then $R^{7a}$ is other than H;
vi) when the compound is according to formula IIIb, $HET^1$ is furanyl or quinolin-3-yl, and each of $R^{3'}$ and $R^4$ is H; then $R^{7a}$ is other than H or methoxy;
vii) when the compound is according to formula IIIb, and $HET^1$ is pyrrolyl; then $R^{7a}$ is other than H or methyl; and
viii) when the compound is according to formula IIIb; then $HET^1$ is other than benzopyranyl.

In one particular embodiment, with respect to the compound of formula IIIa-IIIb, $R^{7a}$ is other than H. In one particular embodiment, with respect to the compound of formula IIIa-IIIb, $R^{7b}$ is other than H.

In one particular embodiment, with respect to the compound of formula IIIa-IIIc, when m is 1, A is N; then the N can be substituted or unsubstituted. In one embodiment A is NH. In another embodiment, A is N—$R^{5a}$ and $R^{5a}$ is as described herein.

In a further aspect, the present invention provides pharmaceutical compositions comprising a heterocyclic compound of the invention, and a pharmaceutical carrier, excipient or diluent. In this aspect of the invention, the pharmaceutical composition can comprise one or more of the compounds described herein. Moreover, the compounds of the present invention useful in the pharmaceutical compositions and treatment methods disclosed herein, are all pharmaceutically acceptable as prepared and used.

In a further aspect, this invention provides a method of treating a mammal susceptible to or afflicted with a condition from among those listed herein, and particularly, such condition as may be associated with RORγt. Such conditions include, without limitation, multiple sclerosis (and the animal model thereof, EAE), rheumatoid arthritis (and the animal model thereof, CIA), inflammatory bowel disease (IBD), cancer, graft-versus-host disease, asthma, psoriasis, diabetes, uveitis, bronchitis, allergic rhinitis, chronic obstructive pulmonary disease, arteriosclerosis, and *H. pylori* infections and ulcers resulting from such infection.

In a further aspect, an assay for screening to identify modulators of RORγ/γt transcriptional activity is envisioned, the assay comprising a first insect cell line that expresses a fusion protein comprising a RORγ/γt sequence, wherein the RORγ/γt sequence does not comprise the DNA binding domain (DBD) of full length RORγ/γt and a yeast GAL4

DBD, wherein expression of the fusion protein is transcriptionally regulated by an inducible promoter, and wherein the first insect cell line further comprises a reporter, whose expression is upregulated in the presence of the fusion protein. Accordingly, the component of the fusion protein representative of RORγ/γt sequences is a DBD-deleted RORγ/γt sequence. The fusion protein is essentially a chimeric protein wherein the RORγ/γt DBD is deleted from the RORγ/γt sequences and replaced with the yeast GAL4 DNA binding domain DBD. In a particular embodiment, the Gal4 DNA binding domain (G4DBD) corresponds to amino acids 1 through 147 of Gal4 protein and the DBD-deleted RORγ/γt sequence is amino acids 79 to the carboxyl terminal end of mouse RORγt. In a particular embodiment, the inducible promoter is a copper inducible promoter.

In an embodiment of the assay, the reporter is transcriptionally regulated by a plurality of copies of the GAL4 binding site enhancer (UAS) operatively linked to nucleic acid sequences encoding the reporter. In a particular embodiment of the assay, the plurality of copies of the GAL4 binding site enhancer (UAS) is between 1 and 5 copies. In a more particular embodiment, the reporter is the firefly luciferase reporter.

In an aspect of the assay, the first insect cell line is the S2 cell line. In another aspect of the assay, the fusion protein is encoded by nucleic acids that are integrated into the genome of the first insect cell line or encoded by extrachromosomal nucleic acids incorporated into the first insect cell line. Accordingly, the assay may relate to stably transfected cell line or a transiently transfected cell line. The choice of stably or transiently transfected cell line depends, in part, on the number of compounds to be tested and availability and cost of assay reagents required.

As described herein, the assay may further comprise a second insect cell line that expresses a second fusion protein comprising a RORα sequence, wherein the RORα sequence does not comprise the DBD of full length RORα sequence and a yeast GAL4 DBD; a third insect cell line that expresses a third fusion protein comprising a DHR3 sequence, wherein the DHR3 sequence does not comprise the DNA binding domain (DBD) of full length DHR3 sequence and a yeast GAL4 DBD, and a fourth insect cell line that expresses a fourth fusion protein comprising a transcriptionally active domain of general transcriptional activator VP16 and a yeast GAL4 DBD, wherein expression of the second, third and fourth fusion proteins is transcriptionally regulated by inducible promoters. In a particular embodiment, the DBD-deleted mouse RORα sequence is amino acids 142 to the carboxyl terminal end of mouse RORα and the DBD-deleted *Drosophila* DHR3 is amino acids 120 to the carboxyl terminal end of *Drosophila* DHR3. In an embodiment, inducible promoters regulating expression of the first, second, third, and fourth fusion proteins are identical promoters. In yet another embodiment, the inducible promoters regulating expression of the first, second, third, and fourth fusion proteins are copper inducible promoters.

Methods for using the assay of the invention are also encompassed herein. Such methods include those involving use of the cell-based assay systems described herein to screen diverse compound libraries, such as those available from research institutions, federal agencies, and/or commercial vendors, to identify modulators of RORγ/γt transcriptional activity. Modulators of RORγ/γt transcriptional activity may be identified based on results determined using the first insect cell-based assay system described herein alone or in combination with at least one of the second, third, and fourth insect cell-based assay systems described herein to identify compounds that are specific modulators of RORγ/γt transcriptional activity. Modulators identified using assays described herein may be identified as inhibitors or agonists of RORγ/γt transcriptional activity. Compounds identified using the cell based systems described herein may be assessed in secondary screens, also described herein and understood in the art, to validate their identity as bona fide modulators of RORγ/γt transcriptional activity.

Other objects and advantages will become apparent to those skilled in the art from a consideration of the ensuing detailed description.

BRIEF DESCRIPTION OF THE DRAWINGS

FIG. 3 shows FACS plot analyses revealing that NCGC00242624 and NCGC00238427 selectively inhibit RORγt dependent, but not RORα dependent, human Th17 cell differentiation. Compound NCGC00242626 serves as a negative control along with the carrier control DMSO, neither of which exhibits the ability to inhibit RORγt dependent human Th17 cell differentiation.

DETAILED DESCRIPTION OF THE INVENTION

Definitions

Figure 1:
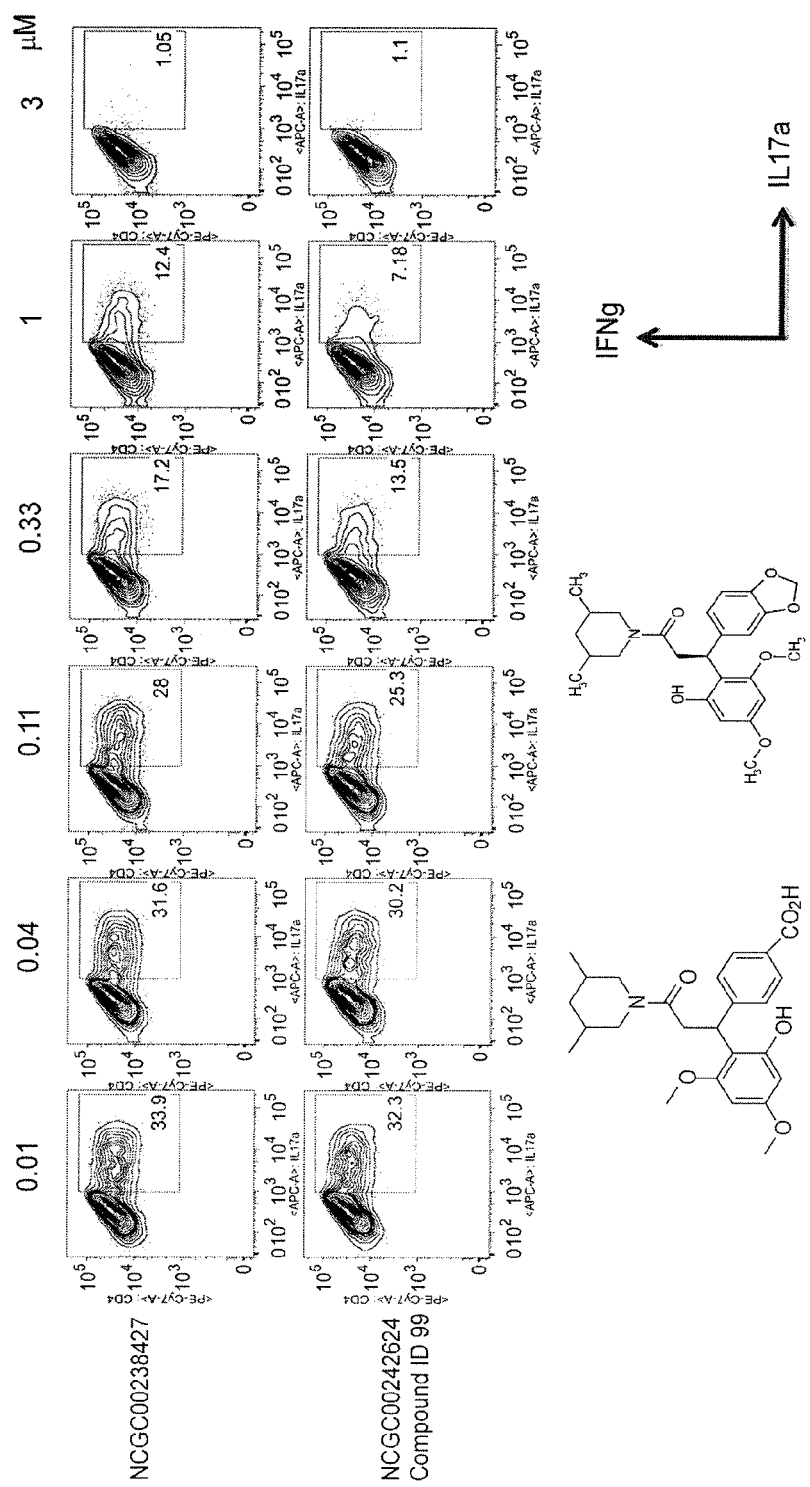
FIG. 1 shows fluorescence activated cell sorter (FACS) plot analyses revealing the effects of NCGC00242624 and NCGC00238427 on mouse Th17 differentiation. NCGC00242624, a more stable compound, suppresses mouse Th17 cell differentiation with similar activity to NCGC00238427.

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope. It should be further understood that the terms "groups" and "radicals" can be considered interchangeable when used herein.

"Acyl" refers to a radical —C(O)$R^{20}$, where $R^{20}$ is hydrogen, alkyl, cycloalkyl, cycloheteroalkyl, aryl, arylalkyl, heteroalkyl, heteroaryl, heteroarylalkyl as defined herein. Representative examples include, but are not limited to, formyl, acetyl, cyclohexylcarbonyl, cyclohexylmethyl-carbonyl, benzoyl, benzylcarbonyl and the like.

"Acylamino" refers to a radical —N$R^{21}$C(O)$R^{22}$, where $R^{21}$ is hydrogen, alkyl, cycloalkyl, cycloheteroalkyl, aryl, arylalkyl, heteroalkyl, heteroaryl, heteroarylalkyl and $R^{22}$ is hydrogen, alkyl, alkoxy, cycloalkyl, cycloheteroalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzyl carbonyl amino and the like.

"Acyloxy" refers to the group —OC(O)$R^{23}$ where $R^{23}$ is hydrogen, alkyl, aryl or cycloalkyl.

"Substituted alkenyl" includes those groups recited in the definition of "substituted" herein, and particularly refers to an alkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)— alkyl-S(O)$_2$— and aryl-S(O)$_2$—.

"Alkoxy" refers to the group —OR$^{24}$ where R$^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Substituted alkoxy" includes those groups recited in the definition of "substituted" herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkoxycarbonylamino" refers to the group —NR$^{25}$C(O)OR$^{26}$, where R$^{25}$ is hydrogen, alkyl, aryl or cycloalkyl, and R$^{26}$ is alkyl or cycloalkyl.

"Alkyl" refers to monovalent saturated alkane radical groups particularly having up to about 11 carbon atoms, more particularly as a lower alkyl, from 1 to 8 carbon atoms and still more particularly, from 1 to 6 carbon atoms. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "lower alkyl" refers to alkyl groups having 1 to 6 carbon atoms. The term "alkyl" also includes "cycloalkyls" as defined below.

"Substituted alkyl" includes those groups recited in the definition of "substituted" herein, and particularly refers to an alkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, heteroaryl, keto, nitro, thioalkoxy, substituted thioalkoxy, thioaryloxy, thioketo, thiol, alkyl-S(O)—, aryl-S(O)—, alkyl-S(O)$_2$—, and aryl-S(O)$_2$—.

"Alkylene" refers to divalent saturated alkene radical groups having 1 to 11 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Substituted alkylene" includes those groups recited in the definition of "substituted" herein, and particularly refers to an alkylene group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, amino-carbonylamino, aminocarbonyloxy, aryl, aryloxy, azido, carboxyl, cyano, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkenyl" refers to monovalent olefinically unsaturated hydrocarbyl groups preferably having 2 to 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkenylene" refers to divalent olefinically unsaturated hydrocarbyl groups particularly having up to about 11 carbon atoms and more particularly 2 to 6 carbon atoms which can be straight-chained or branched and having at least 1 and particularly from 1 to 2 sites of olefinic unsaturation. This term is exemplified by groups such as ethenylene (—CH=CH—), the propenylene isomers (e.g., —CH=CHCH$_2$— and —C(CH$_3$)=CH— and —CH=C(CH$_3$)—) and the like.

"Alkynyl" refers to acetylenically or alkynically unsaturated hydrocarbyl groups particularly having 2 to 11 carbon atoms, and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Substituted alkynyl" includes those groups recited in the definition of "substituted" herein, and particularly refers to an alkynyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Alkanoyl" or "acyl" as used herein refers to the group R$^{27}$—C(O)—, where R$^{27}$ is hydrogen or alkyl as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Substituted Aryl" includes those groups recited in the definition of "substituted" herein, and particularly refers to an aryl group that may optionally be substituted with 1 or more substituents, for instance from 1 to 5 substituents, particularly 1 to 3 substituents, selected from the group consisting of acyl, acylamino, acyloxy, alkenyl, substituted alkenyl, alkoxy, substituted alkoxy, alkoxycarbonyl, alkyl, substituted alkyl, alkynyl, substituted alkynyl, amino, substituted amino, aminocarbonyl, aminocarbonyl amino, aminocarbonyloxy, aryl, aryloxy, azido, carboxyl, cyano, cycloalkyl, substituted cycloalkyl, halogen, hydroxyl, nitro, thioalkoxy, substituted thioalkoxy, thioaryloxy, thiol, alkyl-S(O)—, aryl-S(O)—, alkyl-S(O)$_2$— and aryl-S(O)$_2$—.

"Fused Aryl" refers to an aryl having two of its ring carbon in common with a second aryl ring or with an aliphatic ring.

"Alkaryl" refers to an aryl group, as defined above, substituted with one or more alkyl groups, as defined above.

"Aralkyl" or "arylalkyl" refers to an alkyl group, as defined above, substituted with one or more aryl groups, as defined above.

"Aryloxy" refers to —O-aryl groups wherein "aryl" is as defined above.

"Alkylamino" refers to the group alkyl-NR$^{28}$R$^{29}$, wherein each of R$^{28}$ and R$^{29}$ are independently selected from hydrogen and alkyl.

"Arylamino" refers to the group aryl-NR$^{30}$R$^{31}$, wherein each of R$^{30}$ and R$^{31}$ are independently selected from hydrogen, aryl and heteroaryl.

"Alkoxyamino" refers to a radical —N(H)OR$^{32}$ where R$^{32}$ represents an alkyl or cycloalkyl group as defined herein.

"Alkoxycarbonyl" refers to a radical —C(O)-alkoxy where alkoxy is as defined herein.

"Alkylarylamino" refers to a radical —NR$^{33}$R$^{34}$ where R$^{33}$ represents an alkyl or cycloalkyl group and R$^{34}$ is an aryl as defined herein.

"Alkylsulfonyl" refers to a radical —S(O)$_2$R$^{35}$ where R$^{35}$ is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a radical —S(O)R$^{35}$ where R$^{35}$ is an alkyl or cycloalkyl group as defined herein. Representative examples include, but are not limited to, methylsulfinyl, ethylsulfinyl, propylsulfinyl, butylsulfinyl and the like.

"Alkylthio" refers to a radical —SR$^{35}$ where R$^{35}$ is an alkyl or cycloalkyl group as defined herein that may be optionally substituted as defined herein. Representative examples include, but are not limited to, methylthio, ethylthio, propylthio, butylthio, and the like.

"Amino" refers to the radical —NH$_2$.

"Substituted amino" includes those groups recited in the definition of "substituted" herein, and particularly refers to the group —N(R$^{36}$)$_2$ where each R$^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R$^{36}$)$_2$ is an amino group.

"Aminocarbonyl" refers to the group —C(O)NR$^{37}$R$^{37}$ where each R$^{37}$ is independently hydrogen, alkyl, aryl and cycloalkyl, or where the R$^{37}$ groups are joined to form an alkylene group.

"Aminocarbonylamino" refers to the group —NR$^{38}$C(O)NR$^{38}$R$^{38}$ where each R$^{38}$ is independently hydrogen, alkyl, aryl or cycloalkyl, or where two R groups are joined to form an alkylene group.

"Aminocarbonyloxy" refers to the group —OC(O)NR$^{39}$R$^{39}$ where each R$^{39}$ is independently hydrogen, alkyl, aryl or cycloalkyl, or where the R groups are joined to form an alkylene group.

"Arylalkyloxy" refers to an —O-arylalkyl radical where arylalkyl is as defined herein.

"Arylamino" means a radical —NHR$^{40}$ where R$^{40}$ represents an aryl group as defined herein.

"Aryloxycarbonyl" refers to a radical —C(O)—O-aryl where aryl is as defined herein.

"Arylsulfonyl" refers to a radical —S(O)$_2$R$^{41}$ where R$^{41}$ is an aryl or heteroaryl group as defined herein.

"Azido" refers to the radical —N$_3$.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, iso benzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R$^{42}$)$_2$ where each R$^{42}$ group is independently hydrogen, alkyl, cycloalkyl or aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Substituted cycloalkyl" includes those groups recited in the definition of "substituted" herein, and particularly refers to a cycloalkyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Cycloalkoxy" refers to the group —OR$^{43}$ where R$^{43}$ is cycloalkyl. Such cycloalkoxy groups include, by way of example, cyclopentoxy, cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Substituted cycloalkenyl" includes those groups recited in the definition of "substituted" herein, and particularly refers to a cycloalkenyl group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Fused Cycloalkenyl" refers to a cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR$^{44}$R$^{45}$ where R$^{44}$ and R$^{45}$ independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

"Ethenyl" refers to substituted or unsubstituted —(C═C)—.

"Ethylene" refers to substituted or unsubstituted —(C—C)—.

"Ethynyl" refers to —(C≡C)—.

"Halo" or "halogen" refers to fluoro, chloro, bromo and iodo. Preferred halo groups are either fluoro or chloro.

"Hydroxy" refers to the radical —OH.

"Nitro" refers to the radical —NO$_2$.

"Substituted" refers to a group in which one or more hydrogen atoms are each independently replaced with the same or different substituent(s). Typical substituents include, but are not limited to, —X, —R$^{46}$, —O$^{31}$, ═O, —OR$^{46}$, —SR$^{46}$, —S$^-$, ═S, —NR$^{46}$R$^{47}$, ═NR$^{46}$, —CX$_3$, —CF$_3$, —CN, —OCN, —SCN, —NO, —NO$_2$, ═N$_2$, —N$_3$, —S(O)$_2$O$^-$, —S(O)$_2$OH, —S(O)$_2$R$^{46}$, —OS(O$_2$)O$^-$, —OS(O)$_2$R$^{46}$—P(O)(O$^-$)$_2$, —P(O)(OR$^{46}$)(O$^-$), —OP(O)(OR$^{46}$)(OR$^{47}$), —C(O)R$^{46}$, —C(S)R$^{46}$, —C(O)OR$^{46}$, —C(O)NR$^{46}$R$^{47}$, —C(O)O$^-$, —C(S)OR$^{46}$, —NR$^{48}$C(O)NR$^{46}$R$^{47}$, —NR$^{48}$C(S)NR$^{46}$R$^{47}$, —NR$^{49}$C(NR$^{48}$)NR$^{46}$R$^{47}$ and —C(NR$^{48}$)NR$^{46}$R$^{47}$, where each X is independently a halogen; each R$^{46}$, R$^{47}$, R$^{48}$ and R$^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{50}$R$^{51}$, —C(O)R$^{50}$ or —S(O)$_2$R$^{50}$ or optionally R$^{50}$ and R$^{51}$ together with the atom to which they are both attached form a cycloheteroalkyl or substituted cycloheteroalkyl ring; and R$^{50}$ and R$^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

Examples of representative substituted aryls include the following

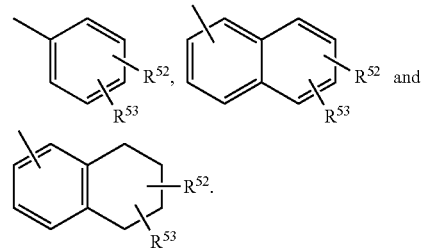

In these formulae one of R$^{52}$ and R$^{53}$ may be hydrogen and at least one of R$^{52}$ and R$^{53}$ is each independently selected from alkyl, alkenyl, alkynyl, cycloheteroalkyl, alkanoyl, alkoxy, aryloxy, heteroaryloxy, alkylamino, arylamino, heteroarylamino, NR$^{54}$COR$^{55}$, N$^{54}$SOR$^{55}$, NR$^{54}$SO$_2$R$^{57}$, COOalkyl, COOaryl, CONR$^{54}$R$^{55}$, CONR$^{54}$OR$^{55}$, NR$^{54}$R$^{55}$, SO$_2$NR$^{54}$R$^{55}$, S-alkyl, S-alkyl, SOalkyl, SO$_2$alkyl, Saryl, SOaryl, SO$_2$aryl; or R$^{52}$ and R$^{53}$ may be joined to form a cyclic ring (saturated or unsaturated) from 5 to 8 atoms, optionally containing one or more heteroatoms selected from the group N, O or S. R$^{54}$, R$^{55}$, and R$^{56}$ are independently hydrogen, alkyl, alkenyl, alkynyl, perfluoroalkyl, cycloalkyl, cycloheteroalkyl, aryl, substituted aryl, heteroaryl, substituted or hetero alkyl or the like.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

Examples of representative heteroaryls include the following:

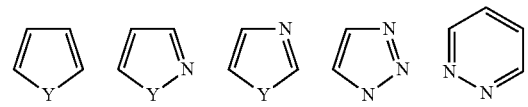

-continued

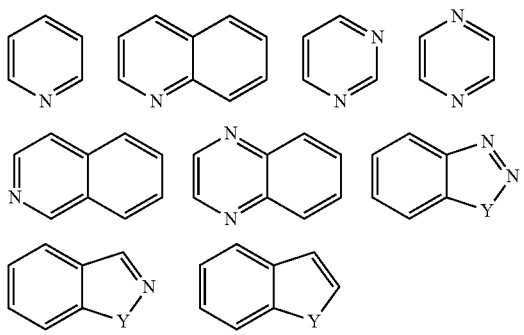

wherein each Y is selected from carbonyl, N, NR$^{58}$, O, and S; and R$^{58}$ is independently hydrogen, alkyl, cycloalkyl, cycloheteroalkyl, aryl, heteroaryl, heteroalkyl or the like.

As used herein, the term "cycloheteroalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl, and are shown in the following illustrative examples:

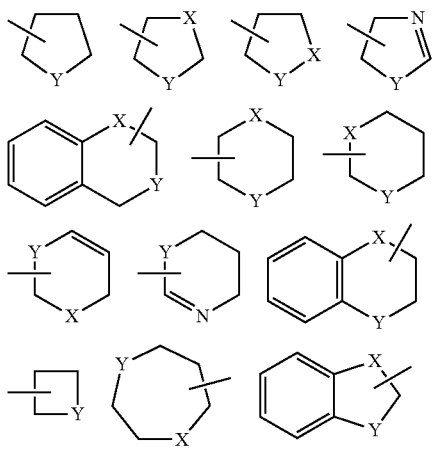

wherein each X is selected from CR$^{58}{}_2$, NR$^{58}$, O and S; and each Y is selected from NR$^{58}$, O and S; and R$^{58}$ is independently hydrogen, alkyl, cycloalkyl, cycloheteroalkyl, aryl, heteroaryl, heteroalkyl or the like. These cycloheteroalkyl rings may be optionally substituted with one or more groups selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—. Substituting groups include carbonyl or thiocarbonyl which provide, for example, lactam and urea derivatives.

Examples of representative cycloheteroalkenyls include the following:

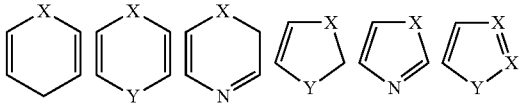

wherein each X is selected from CR$^{58}{}_2$, NR$^{58}$, O and S; and each Y is selected from carbonyl, N, NR$^{58}$, O and S; and R$^{58}$ is independently hydrogen, alkyl, cycloalkyl, cycloheteroalkyl, aryl, heteroaryl, heteroalkyl or the like.

Examples of representative aryl having hetero atoms containing substitution include the following:

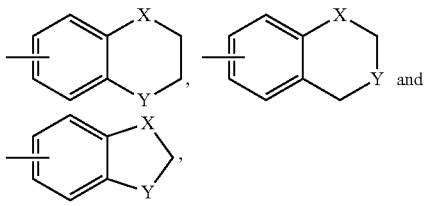

wherein each X is selected from C—R$^{58}{}_2$NR$^{58}$, O and S; and each Y is selected from carbonyl, NR$^{58}$, O and S; and R$^{58}$ is independently hydrogen, alkyl, cycloalkyl, cycloheteroalkyl, aryl, heteroaryl, heteroalkyl or the like.

"Hetero substituent" refers to a halo, O, S or N atom-containing functionality that may be present as an R$^4$ in a R$^4$C group present as substituents directly on A, B, W, Y or Z of the compounds of this invention or may be present as a substituent in the "substituted" aryl and aliphatic groups present in the compounds.

Examples of hetero substituents include:
- halo,
- —NO$_2$, —NH$_2$, —NHR$^{59}$, —N(R$^{59}$)$_2$,
- —NRCOR, —NR$^{59}$SOR$^{59}$, —NR$^{59}$SO$_2$R$^{59}$, OH, CN,
- —CO$_2$H,
- —R$^{59}$—OH, —O—R$^{59}$, —COOR$^{59}$,
- —CON(R$^{19}$)$_2$, —CONROR$^{59}$,
- —SO$_3$H, —R$^{59}$—S, —SO$_2$N(R$^{59}$)$_2$,
- —S(O)R$^{59}$, —S(O)$_2$R$^{59}$ wherein each R$^{59}$ is independently an aryl or aliphatic, optionally with substitution. Among hetero substituents containing R$^{59}$ groups, preference is given to those materials having aryl and alkyl R$^{59}$ groups as defined herein. Preferred hetero substituents are those listed above.

"Hydrogen bond donor" group refers to a group containing O—H, or N—H functionality. Examples of "hydrogen bond donor" groups include —OH, —NH$_2$, and —NH—R$^{59a}$ and wherein R$^{59a}$ is alkyl, cycloalkyl, aryl, or heteroaryl.

"Dihydroxyphosphoryl" refers to the radical —PO(OH)$_2$.

"Substituted dihydroxyphosphoryl" includes those groups recited in the definition of "substituted" herein, and particularly refers to a dihydroxyphosphoryl radical wherein one or both of the hydroxyl groups are substituted. Suitable substituents are described in detail below.

"Aminohydroxyphosphoryl" refers to the radical —PO(OH)NH$_2$.

"Substituted aminohydroxyphosphoryl" includes those groups recited in the definition of "substituted" herein, and particularly refers to an aminohydroxyphosphoryl wherein the amino group is substituted with one or two substituents. Suitable substituents are described in detail below. In certain embodiments, the hydroxyl group can also be substituted.

"Thioalkoxy" refers to the group —$SR^{60}$ where $R^{60}$ is alkyl.

"Substituted thioalkoxy" includes those groups recited in the definition of "substituted" herein, and particularly refers to a thioalkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

"Sulfanyl" refers to the radical HS—. "Substituted sulfanyl" refers to a radical such as RS— wherein R is any substituent described herein.

"Sulfonyl" refers to the divalent radical —S(O$_2$)—. "Substituted sulfonyl" refers to a radical such as $R^{61}$—(O$_2$)S— wherein $R^{61}$ is any substituent described herein. "Aminosulfonyl" or "Sulfonamide" refers to the radical H$_2$N(O$_2$)S—, and "substituted aminosulfonyl" "substituted sulfonamide" refers to a radical such as $R^{62}{}_2$N(O$_2$)S— wherein each $R^{62}$ is independently any substituent described herein.

"Sulfone" refers to the group —SO$_2R^{63}$. In particular embodiments, $R^{63}$ is selected from H, lower alkyl, alkyl, aryl and heteroaryl.

"Thioaryloxy" refers to the group —$SR^{64}$ where $R^{64}$ is aryl.

"Thioketo" refers to the group =S.

"Thiol" refers to the group —SH.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like.

"Pharmaceutically acceptable vehicle" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both.

As used herein, the term "operably linked" refers to a regulatory sequence capable of mediating the expression of a coding sequence and which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", or "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. In other applications, the introduced nucleic acid may exist in the recipient cell or host organism only transiently.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the basic and novel characteristics of the sequence.

Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy) alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Calm and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of m electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

The Compounds

The present invention provides a method for preventing, treating or ameliorating in a mammal a disease or condition that is causally related to the activity of the RORγ or RORγt in vivo, which comprises administering to the mammal an effective disease-treating or condition-treating amount of a compound according to formula I:

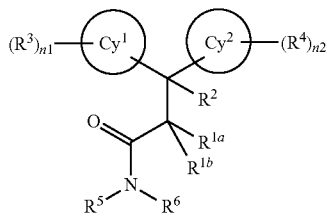

or a pharmaceutically acceptable salt, solvate or prodrug thereof;

or stereoisomers, isotopic variants and tautomers thereof; wherein each $Cy^1$ and $Cy^2$ is independently selected from substituted or unsubstituted aryl and heteroaryl;

each n1 and n2 is independently 1, 2, 3, 4 or 5;

each $R^{1a}$ and $R^{1b}$ is independently H, substituted or unsubstituted $C_1$-$C_6$ alkyl, or CN; or $R^{1a}$ and $R^{1b}$ joined together to form cycloalkyl ring;

$R^2$ is H, substituted or unsubstituted $C_1$-$C_6$ alkyl, or aryl;

or one of $R^{1a}$ and $R^{1b}$ is joined to the C of $CR^2$ to form a cyclopropyl ring; or $R^2$ is joined to the C of $CR^{1a}R^{1b}$ to form a cyclopropyl ring;

each $R^3$ and $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol; or any two adjacent $R^3$ groups, or any two adjacent $R^4$ groups may join together to form a substituted or unsubstituted carbocyclic or heterocyclic ring;

each $R^5$ and $R^6$ is independently selected from H, substituted or unsubstituted alkyl, substituted or unsubstituted cycloalkyl, substituted or unsubstituted aryl, substituted or unsubstituted heteroaryl, substituted or unsubstituted aralkyl, and substituted or unsubstituted heteroarylalkyl; or $R^5$ and $R^6$, together with the N they are attached to, form a 4-12 membered substituted or unsubstituted heterocycloalkyl;

provided that i) at least one of $Cy^1$ and $Cy^2$ is heteroaryl; and ii) when the compound is

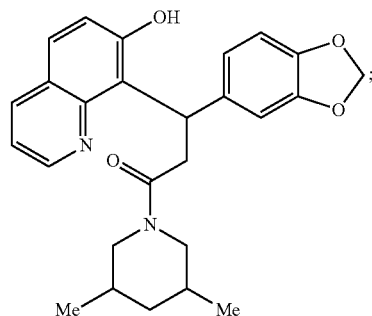

Compound 146 then the compound is in the form of an acid addition salt;

or provided that i) when each of $Cy^1$ and $Cy^2$ is phenyl; then at least one $R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl; and wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;

ii) when the compound is

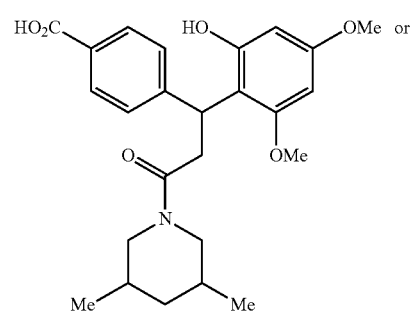

Compound 99

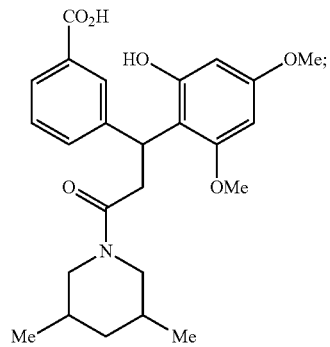

Compound 101 then the compound is in the form of a sodium, potassium, calcium, or ammonium salt; and iii) the compound is other than the compounds listed in Table 1, wherein compound ID is 83, 84, 95, 100, 111, and 139.

In certain aspects, the present invention provides a method for preventing, treating or ameliorating in a mammal a disease or condition that is causally related to the activity of the RORγ or RORγt in vivo, which comprises administering to the mammal an effective disease-treating or condition-treating amount of a compound according to formula I; or a pharmaceutically acceptable salt, solvate or prodrug thereof; or stereoisomers, isotopic variants and tautomers thereof; wherein
- one of $Cy^1$ and $Cy^2$ is substituted or unsubstituted heteroaryl; and the other is selected from substituted or unsubstituted aryl and heteroaryl;
- each n1 and n2 is independently 1, 2, 3, 4 or 5;
- each $R^{1a}$ and $R^{1b}$ is independently H, substituted or unsubstituted $C_1$-$C_6$ alkyl, or CN; or
- $R^{1a}$ and $R^{1b}$ joined together to form cycloalkyl ring;
- $R^2$ is H, substituted or unsubstituted $C_1$-$C_6$ alkyl, or aryl; or one of $R^{1a}$ and $R^{1b}$ is joined to the C of $CR^2$ to form a cyclopropyl ring; or $R^2$ is joined to the C of $CR^{1a}R^{1b}$ to form a cyclopropyl ring;
- each $R^3$ and $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol; or any two adjacent $R^3$ groups, or any two adjacent $R^4$ groups may join together to form a substituted or unsubstituted carbocyclic or heterocyclic ring;
- each $R^5$ and $R^6$ is independently selected from H, substituted or unsubstituted alkyl, substituted or unsubstituted cycloalkyl, substituted or unsubstituted aryl, substituted or unsubstituted heteroaryl, substituted or unsubstituted aralkyl, and substituted or unsubstituted heteroarylalkyl; or
- $R^5$ and $R^6$, together with the N they are attached to, form a 4-12 membered substituted or unsubstituted heterocycloalkyl;
- provided that
  - i) when the compound is Compound 146; then the compound is in the form of an acid addition salt.

In certain aspects, the present invention provides a method for preventing, treating or ameliorating in a mammal a disease or condition that is causally related to the activity of the RORγ or RORγt in vivo, which comprises administering to the mammal an effective disease-treating or condition-treating amount of a compound according to formula I; or a pharmaceutically acceptable salt, solvate or prodrug thereof; or stereoisomers, isotopic variants and tautomers thereof; wherein
- each Cy1 and Cy2 is independently selected from substituted or unsubstituted phenyl;
- each n1 and n2 is independently 1, 2, 3, 4 or 5;
- each $R^{1a}$ and $R^{1b}$ is independently H, substituted or unsubstituted $C_1$-$C_6$ alkyl, or CN; or
- $R^{1a}$ and $R^{1b}$ joined together to form cycloalkyl ring;
- $R^2$ is H, substituted or unsubstituted $C_1$-$C_6$ alkyl, or aryl; or one of $R^{1a}$ and $R^{1b}$ is joined to the C of $CR^2$ to form a cyclopropyl ring; or $R^2$ is joined to the C of $CR^{1a}R^{1b}$ to form a cyclopropyl ring;
- each $R^3$ and $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfonyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol; or any two adjacent $R^3$ groups, or any two adjacent $R^4$ groups may join together to form a substituted or unsubstituted carbocyclic or heterocyclic ring;
- each $R^5$ and $R^6$ is independently selected from H, substituted or unsubstituted alkyl, substituted or unsubstituted cycloalkyl, substituted or unsubstituted aryl, substituted or unsubstituted heteroaryl, substituted or unsubstituted aralkyl, and substituted or unsubstituted heteroarylalkyl; or
- $R^5$ and $R^6$, together with the N they are attached to, form a 4-12 membered substituted or unsubstituted heterocycloalkyl;
- provided that at least one $R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl; and wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring; provided that
  - i) when the compound is Compound 99 or Compound 101; then the compound is in the form of a sodium, potassium, calcium, or ammonium salt; and
  - ii) the compound is other than the compounds listed in Table 1, wherein compound ID is 83, 84, 95, 100, 111, and 139.

In certain aspects, the invention provides composition of matter and pharmaceutical composition for Compound 99 or Compound 101.

In one particular embodiment, with respect to the compounds of formula I, the compound is Compound 99 or Compound 101 and the compound is in the form of a sodium, potassium, calcium, or ammonium salt.

In another embodiment, with respect to the compounds of formula I, the compound is a sodium, potassium, calcium, or ammonium salt of any one of compounds of formula I, wherein $R^3$ is $CO_2H$, $CH_2CO_2H$. In one particular embodiment, the compound is Compound 99. In another particular embodiment, the compound is Compound 101. In another particular embodiment, the compound is Compound 201 (as depicted in Table 1). In another particular embodiment, the compound is Compound 202 (as depicted in Table 1A).

In certain aspects, the invention provides composition of matter and pharmaceutical composition for the compound is a sodium, potassium, calcium, or ammonium salt of any one of compounds of formula I, wherein $R^3$ is $CO_2H$, $CH_2CO_2H$. In one particular embodiment, the compound is Compound 99. In another particular embodiment, the compound is Compound 101. In another particular embodiment, the compound is Compound 201 (as depicted in Table 1). In another particular embodiment, the compound is Compound 202 (as depicted in Table 1A).

In one embodiment, with respect to the compounds of formula I, the compound is a compound listed in Table 1; and wherein the Compound ID is 83, 84, 95, 100, 111, or 139.

In one embodiment, the present invention does not include the compounds with Compound IDs 83, 84, 95, 100, 111, or 139.

In one embodiment, with respect to the compounds of formula I, each $R^5$ and $R^6$ is independently selected from H, substituted or unsubstituted alkyl, substituted and unsubstituted cycloalkyl, and substituted and unsubstituted phenyl.

In another embodiment, with respect to the compounds of formula I, one of $R^5$ and $R^6$ is H or Me; and the other is independently selected from H, substituted or unsubstituted alkyl, substituted and unsubstituted cycloalkyl, and substituted and unsubstituted phenyl.

In another embodiment, with respect to the compounds of formula I, each $R^5$ and $R^6$ is independently selected from substituted or unsubstituted alkyl.

In another embodiment, with respect to the compounds of formula I, each $R^5$ and $R^6$ is independently selected from unsubstituted alkyl.

In one particular embodiment, with respect to the compounds of formula I, each $R^5$ and $R^6$ is independently selected from H, Me, Et, n-Pr, i-Pr, n-Bu, and t-Bu.

In another embodiment, with respect to the compounds of formula I, each $R^5$ and $R^6$ is independently selected from H, and alkyl substituted with hydroxyl, amino, alkylamino, dialkylamino, cycloalkyl, heterocycloalkyl, aryl, and heteroaryl.

In another particular embodiment, with respect to the compounds of formula I, each $R^5$ and $R^6$ is independently selected from H, Me, Et, hydroxyethyl, hydroxypropyl, aminoethyl, aminopropyl, dimethylaminoethyl, dimethylaminopropyl, piperidinoethyl, morpholinoethyl, cyclopropylmethyl, benzyl, phenethyl, and furanylmethyl.

In one embodiment, with respect to the compounds of formula I, each $R^5$ and $R^6$ is independently selected from H, and cycloalkyl.

In another embodiment, with respect to the compounds of formula I, each $R^5$ and $R^6$ is independently selected from H, cyclopropyl, cyclobutyl, cyclopentyl, and cyclohexyl.

In another particular embodiment, with respect to the compounds of formula I, $R^5$ is H; and $R^6$ is selected from hydroxyethyl, hydroxypropyl, aminoethyl, aminopropyl, dimethylaminoethyl, dimethylaminopropyl, piperidinoethyl, morpholinoethyl, cyclopropylmethyl, cyclohexyl, benzyl, phenethyl, and furanylmethyl.

In yet another particular embodiment, with respect to the compounds of formula I, $R^5$ and $R^6$ are joined together to form a 4-12 membered substituted or unsubstituted heterocycloalkyl.

In yet another particular embodiment, with respect to the compounds of formula I, $R^5$ and $R^6$ are joined together to form azetidinyl, pyrrolidinyl, piperidinyl, piperizinyl, morpholinyl, tetrahydroquinolinyl, indolinyl, or azepinyl, unsubstituted or substituted with one or more alkyl, substituted alkyl, haloalkyl, alkoxyalkyl, hydroxyalkyl, alkoxy, hydroxyl, CN, substituted or unsubstituted aryl, substituted or unsubstituted heteroaryl, amido, acyl, aroyl, or —CO-alkoxy.

In yet another particular embodiment, with respect to the compounds of formula I, $R^5$ and $R^6$ are joined together to form substituted or unsubstituted azetidinyl, substituted or unsubstituted pyrrolidinyl, piperidinyl, piperizinyl, morpholinyl, or azepinyl. In another embodiment, $R^5$ and $R^6$ are joined together to form unsubstituted pyrrolidinyl, piperidinyl, piperizinyl, morpholinyl, or azepinyl. In a particular embodiment. $R^5$ and $R^6$ are joined together to form piperidinyl or piperizinyl.

In one embodiment, with respect to the compounds of formula I, the compound is according to formula IIa, IIb, IIc, IId, IIe, or IIf:

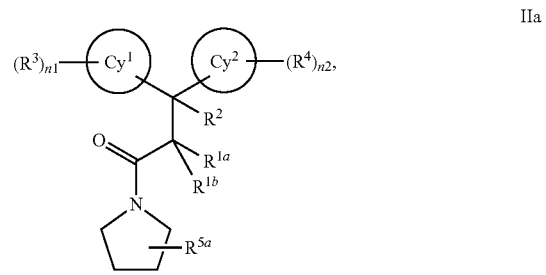

IIa

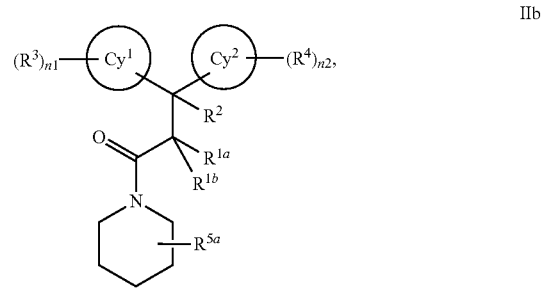

IIb

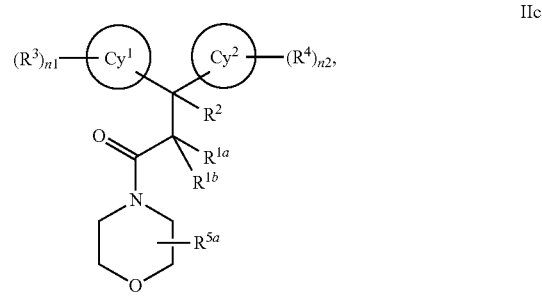

IIc

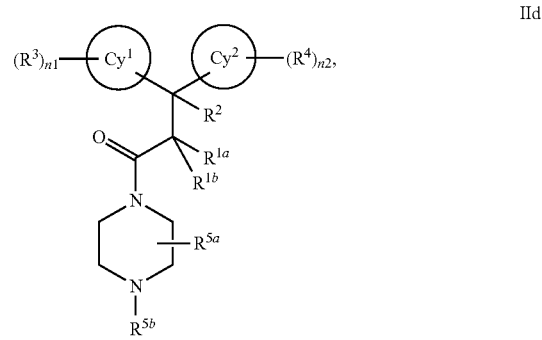

IId

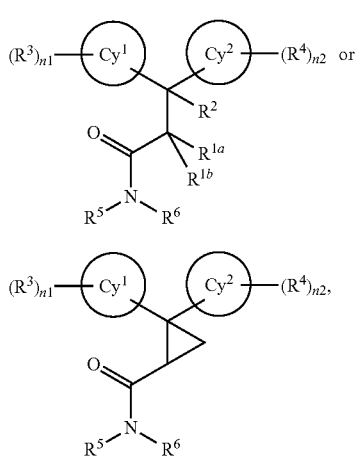

and wherein Cy1, Cy2, n1, n2, $R^1$, $R^2$, $R^3$, $R^4$, $R^5$, and $R^6$ are as described for formula I; and each $R^{5a}$ and $R^{5b}$ is independently H, alkyl, substituted alkyl, haloalkyl, alkoxyalkyl, hydroxyalkyl, alkoxy, hydroxyl, CN, substituted or unsubstituted aryl, substituted or unsubstituted heteroaryl, amido, acyl, aroyl, or —CO-alkoxy.

In one embodiment, with respect to the compounds of formula I-IIf, each of $Cy^1$ and $Cy^2$ is phenyl.

In one embodiment, with respect to the compounds of formula I-IId, each of pyrrolidinyl, piperidinyl, morpholinyl, and piperazinyl can be substituted with more than one $R^{5a}$ group. In one embodiment, with respect to the compounds of formula I-IId, each of pyrrolidinyl, piperidinyl, morpholinyl, and piperazinyl is substituted with one $R^{5a}$ group. In another embodiment, each of pyrrolidinyl, piperidinyl, morpholinyl, and piperazinyl is substituted with two, three or four $R^{5a}$ groups. In a particular embodiment, each of pyrrolidinyl, piperidinyl, morpholinyl, and piperazinyl is substituted with two $R^{5a}$ groups. In one embodiment, each $R^{5a}$ is unsubstituted alkyl. In another embodiment, each $R^{5a}$ is independently Me, Et, i-Pr, n-Pr, i-Bu, n-Bu, or t-Bu.

In one embodiment, with respect to the compounds of formula I-IIf, one of $Cy^1$ and $Cy^2$ is heteroaryl; and the other is phenyl.

In one embodiment, with respect to the compounds of formula I-IIf, each of $Cy^1$ and $Cy^2$ is heteroaryl.

In one embodiment, with respect to the compounds of formula I-IIf, n2 is 1, 2, or 3.

In one embodiment, with respect to the compounds of formula I-IIf, n2 is 1, 2, or 3; and each $R^4$ is independently selected from halo, $C_1$-$C_6$ alkyl, CN, OH, and $C_1$-$C_6$ alkoxy.

In one embodiment, with respect to the compounds of formulae I-IIf, n2 is 1, 2, or 3; and each $R^4$ is independently selected from Cl, Me, OH, and $C_1$-$C_6$ alkoxy. In a particular embodiment, n2 is 3.

In one embodiment, with respect to the compounds of formula I-IIf, $R^4$ is H, alkyl, substituted alkyl, halo, haloalkyl, hydroxyalkyl, alkoxyalkyl, amido, hydroxyl, cyano, or alkoxy.

In one embodiment, with respect to the compounds of formula I-IIf, $R^4$ is H, halo, $C_1$-$C_6$ alkyl, CN, OH, or $C_1$-$C_6$ alkoxy.

In one embodiment, with respect to the compounds of formula I-IIf, $R^4$ is H, Cl, F, Me, $CF_3$, CN, OH, or OMe.

In another particular embodiment, with respect to the compounds of formulae I-IIf, n2 is 1; and $R^4$ is Cl, F, Me, Et, i-Pr, OMe, $CF_3$, CN or OH. In one embodiment $R^4$ is at 4- or para-position of the phenyl ring. In another embodiment, $R^4$ is 4-Cl, 4-F, 4-Me, 4-Et, 4-i-Pr, 4-OMe, 4-$CF_3$, 4-CN or 4-OH. In yet another embodiment, $R^4$ is 3-Cl, 3-F, 3-Me, 3-Et, 3-i-Pr, 3-OMe, 3-$CF_3$, 3-CN or 3-OH.

In one particular embodiment, with respect to the compounds of formulae I-IIf, n1 is 1; $R^4$ is 4-$NMe_2$. In another particular embodiment. $R^4$ is 4-Me. In another particular embodiment, $R^4$ is 2-Me. In another particular embodiment, $R^4$ is 4-OMe. In another particular embodiment, $R^4$ is 4-OEt.

In one particular embodiment, with respect to the compounds of formulae two adjacent $R^4$ groups joined together to form —O—$CH_2$—O—, —O—$CF_2$—O—, —O—$CH_2$—$CH_2$—O—, —O—$CH_2$—$CH_2$—$CH_2$—O—, or —CH=CH—CH=CH—.

In one particular embodiment, with respect to the compounds of formulae the group

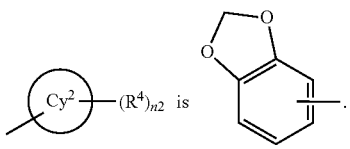

In another particular embodiment, with respect to the compounds of formulae I-IIf, the group

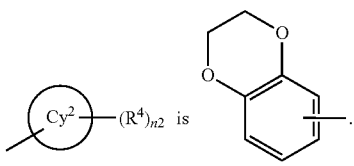

In another particular embodiment, with respect to the compounds of formulae I-IIf, the group

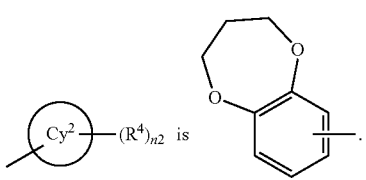

In another particular embodiment, with respect to the compounds of formulae I-IIf, the group

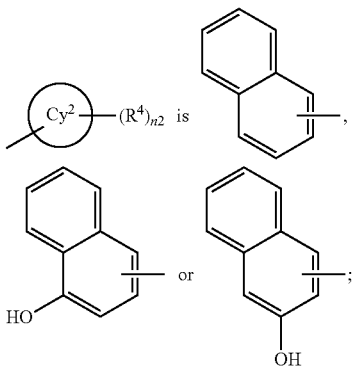

wherein the naphthyl is unsubstituted or substituted with one or more $R^4$ groups.

In one embodiment, with respect to the compounds of formula I, the compound is according to formula IIIa, IIIb, or IIIc:

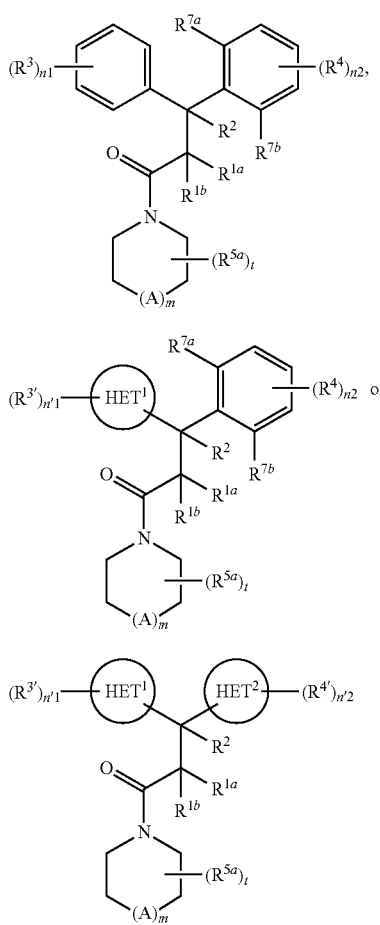

or a pharmaceutically acceptable salt, solvate or prodrug thereof;
or stereoisomers, isotopic variants and tautomers thereof;
and wherein n1, $R^{1a}$, $R^{1b}$, $R^2$, $R^3$, and $R^4$ are as described for formula I; n2 is 1, 2, or 3;
each $HET^1$ and $HET^2$ is independently selected from heteroaryl;
$R^{3'}$ is $R^3$; $R^{4'}$ is $R^4$; n'1 is n1; n'2 is n2;
A is $CR^{8a}R^{8b}$, $NR^{8a}$, O, or S; m is 0 or 1;
each $R^{5a}$ is alkyl, substituted alkyl, halo, haloalkyl, hydroxyalkyl, aryl, heteroaryl, CN, alkoxyalkyl, amido, hydroxyl, alkoxy or substituted alkoxy; and t is 0, 1, 2, or 3;
$R^{7a}$ is H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thio;
$R^{7b}$ is $R^4$; or any two adjacent $R^4$ and $R^{7b}$ groups may join together to form a substituted or unsubstituted carbocyclic or heterocyclic ring; and
each $R^{8a}$ and $R^{8b}$ is independently H, substituted or unsubstituted $C_1$-$C_6$ alkyl, substituted or unsubstituted aryl, or substituted or unsubstituted heteroaryl;
provided that
i) when the compound is according to formula IIIa, then at least one $R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl; and wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;
ii) when the compound is Compound 99 or Compound 101, then the compound is in the form of a sodium, potassium, calcium, or ammonium salt; and
iii) the compound is other than the compounds listed in Table 1, wherein compound ID is 83, 84, 95, 100, 111, and 139.

In a further aspect, the present invention provides composition of a compound according to formula IIIa, IIIb, or IIIc; or a pharmaceutically acceptable salt, solvate or prodrug thereof, or stereoisomers, isotopic variants and tautomers thereof; and wherein
n1, $R^{1a}$, $R^{1b}$, $R^2$, $R^3$, and $R^4$, are as described for formula I; n2 is 1, 2, or 3;
each $HET^1$ and $HET^2$ is independently selected from heteroaryl;
$R^{3'}$ is $R^3$; $R^{4'}$ is $R^4$; n'1 is n1; n'2 is n2;
A is $CR^{8a}R^{8b}$, $NR^{8a}$, O, or S; m is 0 or 1;
each $R^{5a}$ is alkyl, substituted alkyl, halo, haloalkyl, hydroxyalkyl, aryl, heteroaryl, CN, alkoxyalkyl, amido, hydroxyl, alkoxy or substituted alkoxy; and t is 0, 1, 2, or 3;
$R^{7a}$ is OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thio;
$R^{7b}$ is $R^4$; or any two adjacent $R^4$ and $R^{7b}$ groups may join together to form a substituted or unsubstituted carbocyclic or heterocyclic ring; and each $R^{8a}$ and $R^{8b}$ is independently H, substituted or unsubstituted $C_1$-$C_6$ alkyl, substituted or unsubstituted aryl, or substituted or unsubstituted heteroaryl;

provided that
i) when the compound is according to formula IIIa, at least one $R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl; and each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;
ii) when the compound is according to formula IIIa, $R^3$ is $CONR^{3a}R^{3b}$, $R^{3a}$ and $R^{3b}$ are joined together to form a morpholino ring, m is 1, and A is O; then $R^{7a}$ is other than H;
iii) when the compound is Compound 99 or Compound 101, then the compound is in the form of a sodium, potassium, calcium, or ammonium salt;
iv) the compound is other than the compounds listed in Table 1, wherein compound ID is 83, 84, 95, 100, 111, and 139;
v) when the compound is according to formula IIIb; then $R^{7a}$ is other than H;
vi) when the compound is according to formula IIIb, $HET^1$ is furanyl or quinolin-3-yl, and each of $R^{3'}$ and $R^4$ is H; then $R^{7a}$ is other than H or methoxy;
vii) when the compound is according to formula IIIb, and $HET^1$ is pyrrolyl; then $R^{7a}$ is other than H or methyl; and
viii) when the compound is according to formula IIIb; then $HET^1$ is other than benzopyranyl.

For the sake of clarity, the present invention does not include composition of matter for the compounds according to formulae IIIa; wherein one of $R^3$s is not $CO_2H$, $CH_2CO_2H$, $COR^{3a}$, $CONR^{3a}R^{3b}$, $SO_3H$, $SOR^{3a}$, $SO_2R^{3a}$, and heteroaryl; and wherein $R^{3a}$ and $R^{3b}$ are as described herein.

For the sake of clarity, the present invention includes composition of matter for the compounds according to formula IIIa; wherein one of $R^3$s is $CO_2H$, $CH_2CO_2H$, $COR^{3a}$, $CONR^{3a}R^{3b}$, $SO_3H$, $SOR^{3a}$, $SO_2R^{3a}$, and heteroaryl; and wherein $R^{3a}$ and $R^{3b}$ are as described herein.

For the sake of clarity, the present invention does not include composition of matter for the compounds according to formula IIIa; wherein one of $R^3$s is $CONR^{3a}R^{3b}$, $R^{3a}$ and $R^{3b}$ are joined together to form a morpholino ring, m is 1, A is O and $R^{7a}$ is H.

For the sake of clarity, the present invention does not include composition of matter for the compounds according to formula IIIb; wherein $R^{7a}$ is H.

For the sake of clarity, the present invention does not include composition of matter for the compounds according to formula IIIb; wherein $HET^1$ is furanyl or quinolin-3-yl, and each of $R^{3'}$ and $R^4$ is H; and $R^{7a}$ is H or methoxy.

For the sake of clarity, the present invention does not include composition of matter for the compounds according to formulae IIIb; $HET^1$ is pyrrolyl and $R^{7a}$ is H or methyl.

For the sake of clarity, the present invention does not include composition of matter for the compounds according to formula IIIb; $HET^1$ is benzopyranyl.

In one embodiment, with respect to the compounds of formula IIIa-IIIc, t is 0. In another embodiment, t is 1 or 2.

In one embodiment, with respect to the compounds of formula IIIa-IIIb, $R^{7a}$ is other than H. In another embodiment, with respect to the compounds of formula IIIa-IIIb, $R^{7b}$ is other than H.

In one embodiment, with respect to the compounds of formula each of $R^{7a}$ and $R^{7b}$ is independently OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thio.

In one embodiment, with respect to the compounds of formula IIIa-IIIb, each of $R^{7a}$ and $R^{7b}$ is independently OH, substituted or unsubstituted alkyl, substituted or unsubstituted alkoxy, CN, halo, amino, or haloalkyl.

In one embodiment, with respect to the compounds of formula IIIa-IIIb, each of $R^{7a}$ and $R^{7b}$ is independently halo, $C_1$-$C_6$ alkyl, CN, OH, or $C_1$-$C_6$ alkoxy.

In one embodiment, with respect to the compounds of formula each of $R^{7a}$ and $R^{7b}$ is independently Cl, F, Me, $CF_3$, CN, OH, or OMe.

In one embodiment, with respect to the compounds of formula IIIa-IIIb, one of $R^{7a}$ and $R^{7b}$ is OH; and the other is alkoxy.

In one embodiment, with respect to the compounds of formula IIIa-IIIb, each of $R^{7a}$ and $R^{7b}$ is OH or alkoxy.

In one embodiment, with respect to the compounds of formula IIIa-IIIb, one of $R^{7a}$ and $R^{7b}$ is OH; and the other is OMe.

In one embodiment, with respect to the compounds of formula I-IIIb, $R^{1a}$ and $R^{1b}$ is independently H, CN, or Me.

In one embodiment, with respect to the compounds of formula each of $R^{1a}$ and $R^{1b}$ is H. In another embodiment each of $R^{1a}$ and $R^{1b}$ is Me.

In one embodiment, with respect to the compounds of formula one of $R^{1a}$ and $R^{1b}$ is H; and the other is CN.

In one embodiment, with respect to the compounds of formula IIIa-IIIc, m is 0.

In one embodiment, with respect to the compounds of formula IIIa-IIIc, m is 1; and A is C or N. In one embodiment, A is $CH_2$, $CHR^{5a}$, or $CR^{5a}R^{5a}$. In another embodiment A is NH or $NR^{5a}$. In a yet another embodiment, A is O. In a further embodiment, A is S.

In one embodiment, with respect to the compounds of formula IIIb-IIIc, $HET^1$ is selected from pyrrolyl, furanyl, thienyl, imidazolyl, oxazolyl, thiazolyl, pyrazolyl, isoxazolyl, triazolyl, oxadiazolyl, and thiadiazolyl.

In one embodiment, with respect to the compounds of formula IIIb-IIIc, $HET^1$ is selected from pyridyl, pyrimidyl, and pyrazinyl. In one particular embodiment, $HET^1$ is pyridyl.

In one embodiment, with respect to the compounds of formula IIIb-IIIc, $HET^1$ is selected from indolyl, benzimidazolyl, 2-oxobenzimidazolyl, benzofuranyl, benzothiazolyl, and benzthiophenyl. In another embodiment, $HET^1$ is benzothiazol-1-yl.

In one embodiment, with respect to the compounds of formula IIIb-IIIc, the group

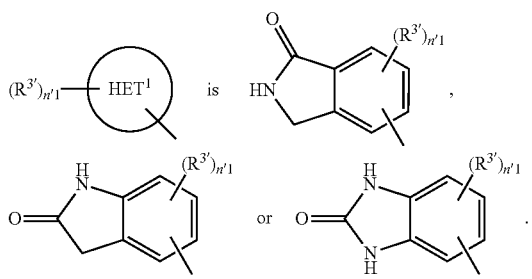

In one embodiment, with respect to the compounds of formula IIIb-IIIc, HET² is selected from pyrrolyl, furanyl, thienyl, imidazolyl, oxazolyl, thiazolyl, pyrazolyl, isoxazolyl, triazolyl, oxadiazolyl, and thiadiazolyl.

In one embodiment, with respect to the compounds of formula IIIb-IIIc, HET² is selected from pyridyl, pyrimidyl, and pyrazinyl.

In one embodiment, with respect to the compounds of formula IIIb-IIIc, HET² is selected from indolyl, benzimidazolyl, 2-oxobenzimidazolyl, benzofuranyl, benzothiazolyl, and benzthiophenyl.

In one embodiment, with respect to the compounds of formula IIIb-IIIc, the group

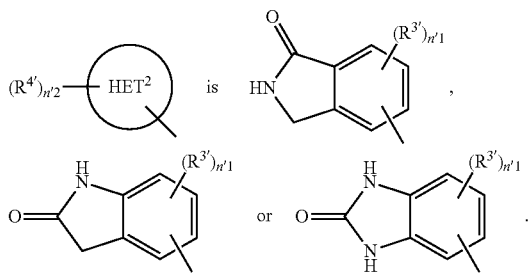

In one embodiment, with respect to the compounds of formula IIIa-IIIc, the group

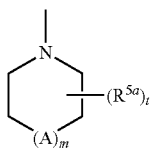

is substituted or unsubstituted

In one embodiment, with respect to the compounds of formula IIIa-IIIc, when m is 1 and A is N, the N is substituted with H or $R^{5a}$ and the $R^{5a}$ is as described herein. In one particular embodiment, A is N—$R^{5a}$, and $R^{5a}$ is alkyl, substituted alkyl, acyl, haloalkyl, hydroxyalkyl, or alkoxyalkyl. In one embodiment, $R^{5a}$ is methoxyalkyl.

In one embodiment, with respect to the compounds of formula IIIa-IIIc, the group

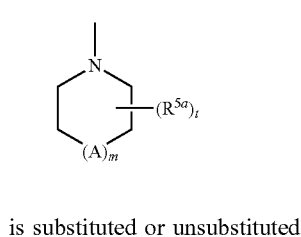

is substituted or unsubstituted

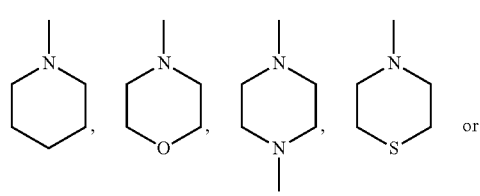

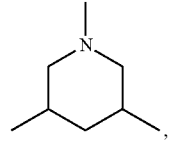

In one particular embodiment, with respect to the compounds of formulae IIIa-IIIb, the group

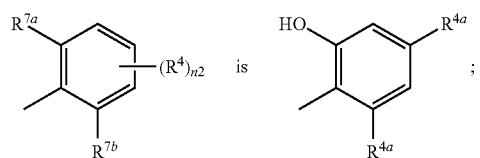

and wherein each $R^{4a}$ is independently selected from alkoxy.

In another particular embodiment, with respect to the compounds of formulae IIIa-IIIb, the group

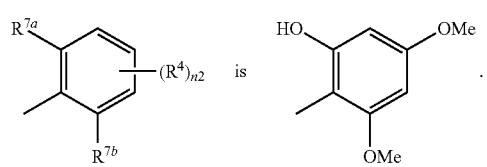

In one embodiment, with respect to the compounds of formula I, the compound is according to formula IVa, IVb, IVc, IVd, IVe, or IVf:

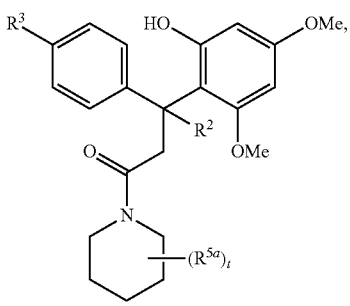

IVa

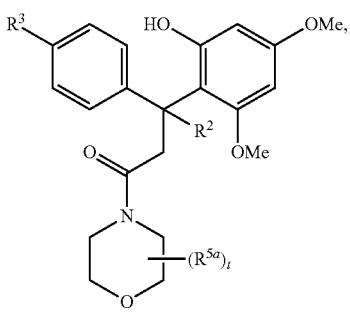

IVb

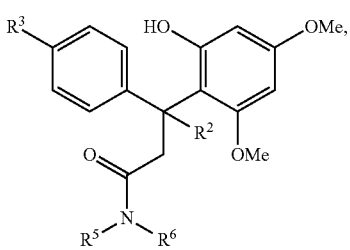

IVc

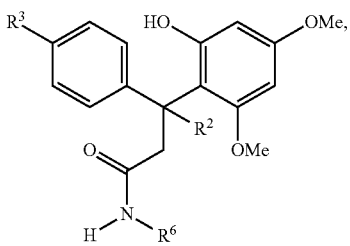

IVd

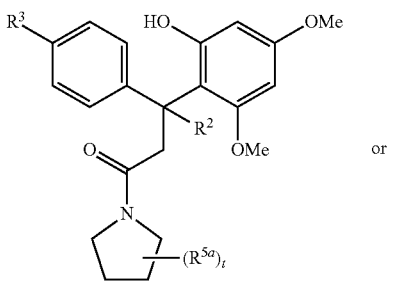

IVe or

IVf or a pharmaceutically acceptable salt, solvate or prodrug thereof;

or stereoisomers, isotopic variants and tautomers thereof;

and wherein n1, $R^2$, $R^4$, $R^5$, and $R^6$ are as described for formula I;

$R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl; wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;

each $R^{5a}$ is alkyl, substituted alkyl, halo, haloalkyl, hydroxyalkyl, aryl, heteroaryl, CN, alkoxyalkyl, amido, hydroxyl, alkoxy or substituted alkoxy; t is 0, 1, 2, or 3;

provided that i) when the compound is Compound 99 or Compound 101 then the compound is in the form of a sodium, potassium, calcium, or ammonium salt; and ii) the compound is other than Compound 95, 100, 111, or 139 (as depicted in Table 1).

In one embodiment, with respect to the formula I-IIIa, and IVa-IVf, $R^3$ is $CO_2H$.

In one embodiment, with respect to the formula I-IIIa, and IVa-IVf, $R^3$ is $SO_3H$.

In one embodiment, with respect to the formula I-IIIa, and IVa-IVf, $R^3$ is $CH_2CO_2H$.

In one embodiment, with respect to the formula I-IIIa, and IVa-IVf, $R^3$ is heteroaryl.

In one embodiment, with respect to the formula I-IIIa, and IVa-IVf, $R^3$ is pyrrolyl, furanyl, thienyl, imidazolyl, oxazolyl, thiazolyl, pyrazolyl, isoxazolyl, triazolyl, oxadiazolyl, thiadiazolyl, and tetrazolyl.

In one embodiment, with respect to the formula I-IIIa, and IVa-IVf, $R^3$ is 1,3,4-triazolyl or tetrazol-5-yl.

In one embodiment, with respect to the formula I-IIIa, and IVa-IVf, $R^3$ is $CONR^{3a}R^{3b}$; wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl. In another embodiment, with respect to the formula I-IIIa, and IVa-IVf, $R^3$ is $CONR^{3a}R^{3b}$; and $R^{3a}$ and $R^{3b}$ joined together to form a substituted or unsubstituted heterocyclic ring.

In one embodiment, with respect to the formula I-IIIa, and IVa-IVf, $R^{3b}$ is H.

In one embodiment, with respect to the formula I-III, and IVa-IVf, $R^{3b}$ is alkyl.

In one embodiment, with respect to the formula I-IIIc, and IVa-IVf, $R^{3b}$ is Me, Et, or i-Pr.

In one embodiment, with respect to the formula I-IIIa, and IVa-IVf, $R^3$ is selected from $COR^{3a}$, $SOR^{3a}$, and $SO_2R^{3a}$; wherein $R^{3a}$ is selected from substituted or unsubstituted alkyl, substituted or unsubstituted cycloalkyl, substituted or unsubstituted aryl, and substituted or unsubstituted heteroaryl.

In one embodiment, $R^{3a}$ is alkyl.

In one embodiment, $R^{3a}$ is Me, Et, or i-Pr.

In one embodiment, with respect to the formula I-IIIa, and IVa-IVf, NH is N—$R^{5a}$, and $R^{5a}$ is alkyl, substituted alkyl, acyl, haloalkyl, hydroxyalkyl, or alkoxyalkyl. In one embodiment, $R^{5a}$ is methoxyalkyl.

In one particular embodiment, with respect to the compounds of formulae I-IIIa, and IVa-IVf, the group

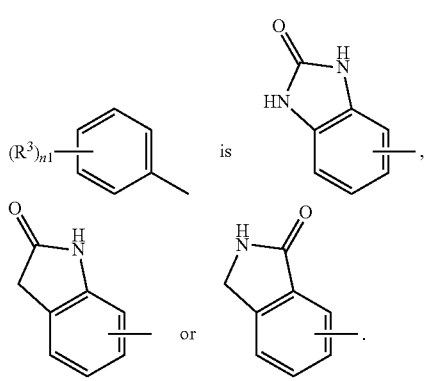

In another particular embodiment, with respect to the compounds of formulae I-IIIa, and IVa-IVf, the group

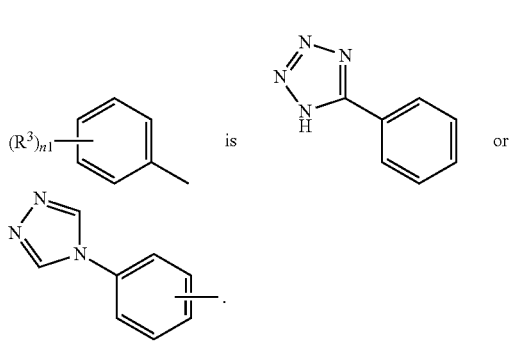

In another particular embodiment, with respect to the compounds of formulae I-IIIa, and IVa-IVf, the group

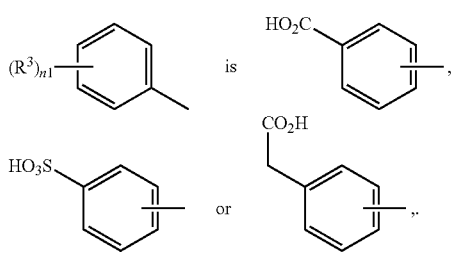

In another particular embodiment, with respect to the compounds of formulae I-IIIa, and IVa-IVf, the group

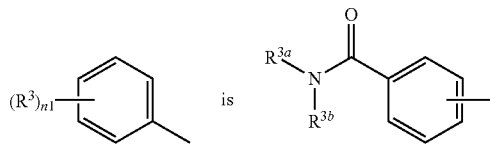

wherein the $R^{3a}$ and $R^{3b}$ are as described herein.

In one particular embodiment, with respect to the compounds of formulae IIIb-IIIc, the group

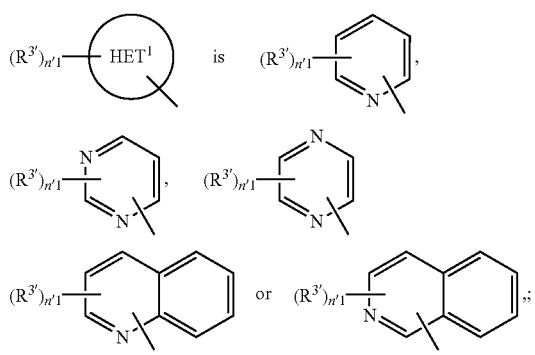

and wherein $R^{3'}$ and n' are as described herein.

In one particular embodiment, with respect to the compounds of formulae III-IIIc, the group

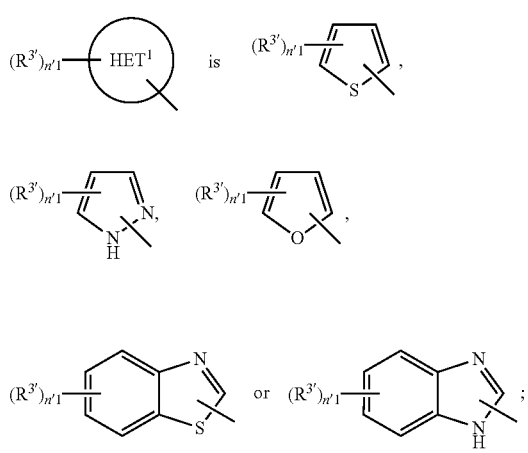

and wherein $R^{3'}$ and n' are as described herein.

In one embodiment, each $R^{3'}$ is H.

In one embodiment, each $R^{3'}$ is independently selected from halo, alkyl, amino, dialkylamino, carboxy, trifluoromethyl, and alkoxy. In another embodiment, each $R^{3'}$ is independently selected from Cl, Me, $CF_3$, OMe, $CO_2H$, $NH_2$, and $NMe_2$.

In one embodiment, with respect to the compounds of formula I, the compound is according to formula Va, Vb, Vc, Vd, Ve, or Vf:

Va 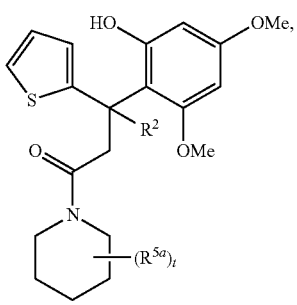

Vb 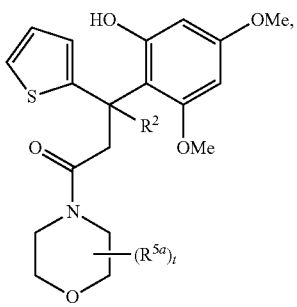

Vc 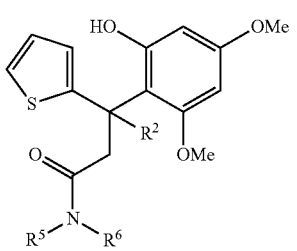

Vd 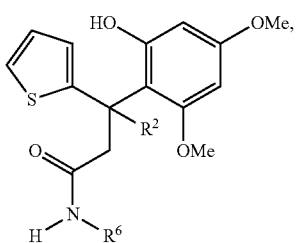

Ve 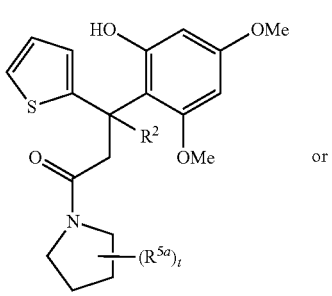 or

Vf 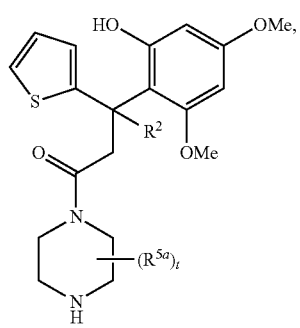

or a pharmaceutically acceptable salt, solvate or prodrug thereof;

or stereoisomers, isotopic variants and tautomers thereof;

and wherein $R^2$, $R^5$, and $R^6$ are as described for formula I; each $R^{5a}$ is alkyl, substituted alkyl, halo, haloalkyl, hydroxyalkyl, aryl, heteroaryl, CN, alkoxyalkyl, amido, hydroxyl, alkoxy or substituted alkoxy; t is 0, 1, 2, or 3.

In one embodiment, with respect to the compounds of formula Va, Vb, Vc, Vd, Ve, or Vf, the 2-thienyl group,

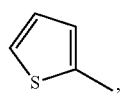

is replaced with 2-benzothiazolyl

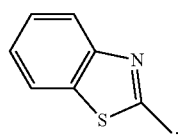

In another embodiment, with respect to the compounds of formula Va, Vb, Vc, Vd, Ve, or Vf, the 2-thienyl group,

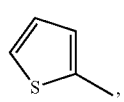

is replaced with

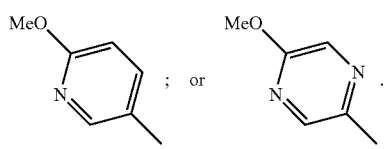

In one embodiment, with respect to the compounds of formula I-III, the compound is according to formula VIa, VIb, VIc, VId, VIe, or VIf:

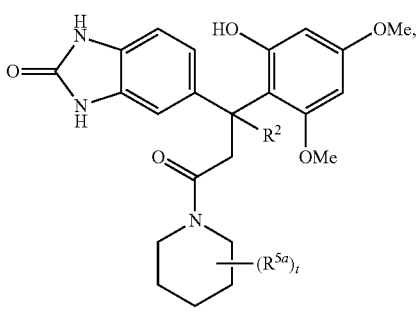
VIa

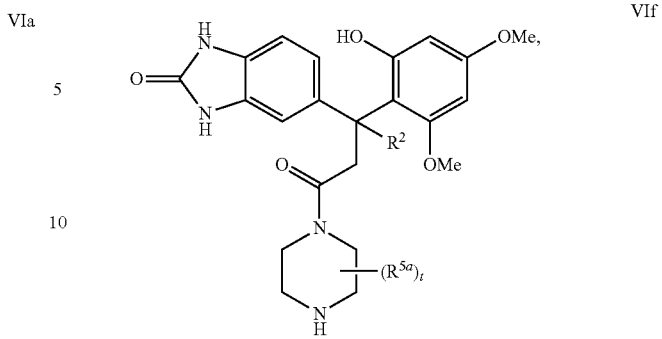
VIf

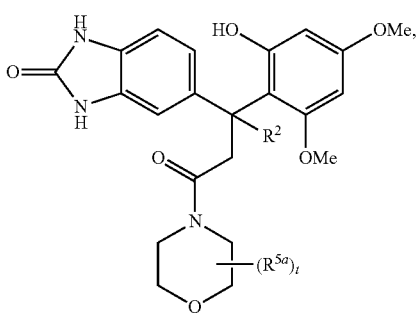
VIb

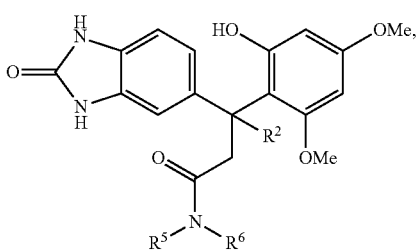
VIc

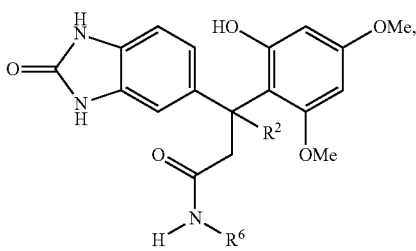
VId

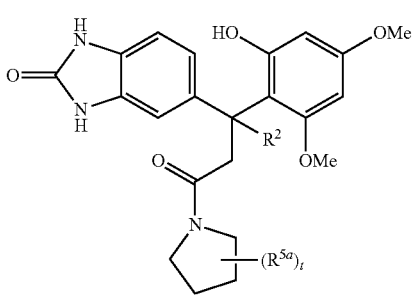
VIe or a pharmaceutically acceptable salt, solvate or prodrug thereof;

or stereoisomers, isotopic variants and tautomers thereof; and wherein $R^2$, $R^5$, and $R^6$ are as described for formula I; each $R^{5a}$ is alkyl, substituted alkyl, halo, haloalkyl, hydroxyalkyl, aryl, heteroaryl, CN, alkoxyalkyl, amido, hydroxyl, alkoxy or substituted alkoxy; and t is 0, 1, 2, or 3.

In one embodiment, with respect to the formula Va-VIf, NH is N—$R^{5a}$, and $R^{5a}$ is alkyl, substituted alkyl, haloalkyl, hydroxyalkyl, or methoxyalkyl.

In one embodiment, with respect to the compounds of formulae I-Vf, $R^2$ is OH.

In one embodiment, with respect to the compounds of formulae I-VIf, $R^2$ is H, substituted or unsubstituted $C_1$-$C_6$ alkyl, or substituted or unsubstituted phenyl.

In another embodiment, with respect to the compounds of formulae I-VIf, $R^2$ is H, Me, OH, or Ph.

In one particular embodiment, with respect to the compounds of formulae I-VIf, $R^2$ is H.

In another particular embodiment, with respect to the compounds of formulae IIIa-VIf, t is 0. In another embodiment t is 1 or 2.

In one embodiment, with respect to the compounds of formulae IIIa-VIf, t is 1; and $R^{5a}$ is OH, Ph, benzyl, or Me. In another embodiment, t is 1; and $R^{5a}$ is Me, Et, n-Pr, or n-Bu. In one particular embodiment, t is 1; and $R^{5a}$ is 3-Me, 3-Et, 3-n-Pr, or 3-n-Bu.

In one embodiment, with respect to the compounds of formulae IIIa-VIf, t is 2; and each $R^{5a}$ is independently OH, Ph, benzyl, or Me. In another embodiment, t is 2; and one $R^{5a}$ is 3-Me and the other is 5-Me. In another embodiment, t is 2; and one $R^{5a}$ is 3-Me and the other is 5-Me.

In one embodiment, with respect to the compounds of formulae IIa-IId, IIIa-VIf, $R^{5a}$ is OH, or Me.

In one particular embodiment, with respect to the compounds of formulae IIa-IId, IIIa-VIf, $R^{5a}$ is Me.

In one particular embodiment, with respect to the compounds of formulae IIa-IId, IIIa-VIf, $R^{5a}$ is Ph.

In one particular embodiment, with respect to the compounds of formulae IIa-IId, IIIa-VIf, $R^{5a}$ is benzyl.

In another particular embodiment, with respect to the compounds of formulae IIa-IId, IIIa-VIf, $R^{5a}$ is 3-Me.

In one particular embodiment, with respect to the compounds of formulae I-VIf, $R^5$, when present, is H. In another embodiment, $R^5$, when present, is Me or Et.

In one particular embodiment, with respect to the compounds of formulae I-VIf, $R^5$, when present, is H. In another embodiment, $R^5$, when present, is Me, Et, n-Pr, or n-Bu. In yet another embodiment, $R^5$, when present, is n-pentyl, n-hexyl, or n-heptyl.

In one particular embodiment, with respect to the compounds of formula I, the compound is according to formula VIIIa, VIIb, VIIc, VIId, VIIe, or VIIf:

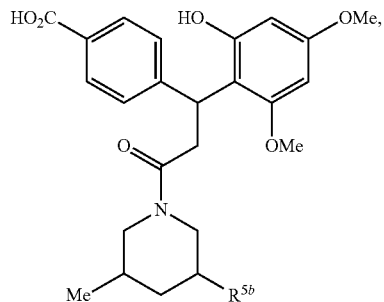
VIIa

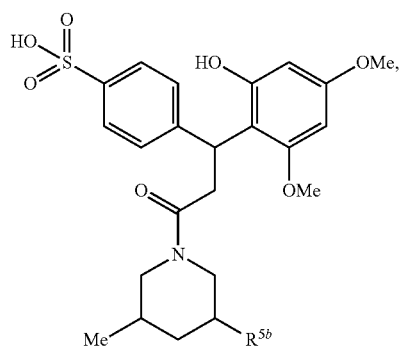
VIIb

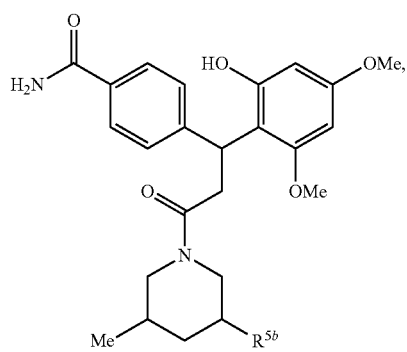
VIIc

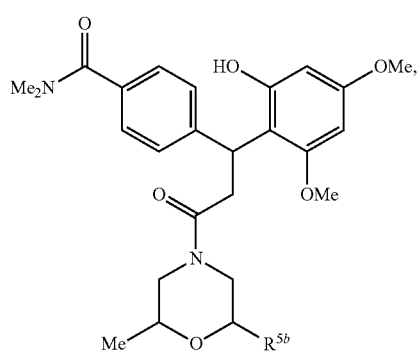
VIId

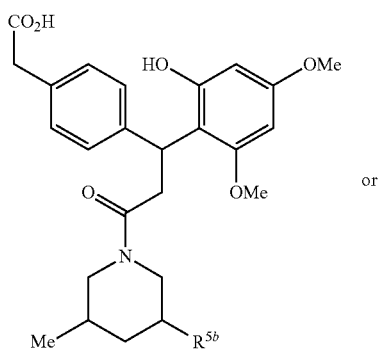
VIIe

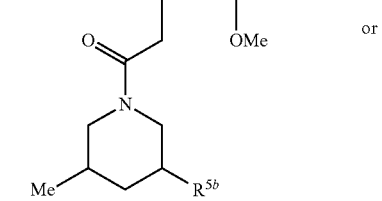
or

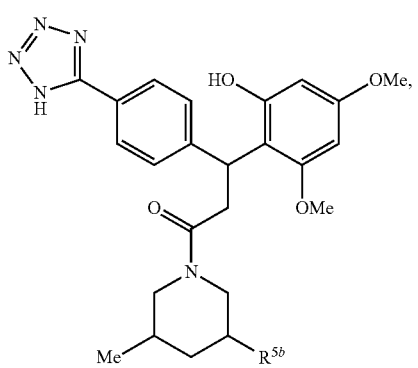
VIIf and wherein $R^{5b}$ is H or Me;

or a pharmaceutically acceptable salt, solvate or prodrug thereof;

or stereoisomers, isotopic variants and tautomers thereof.

In one particular embodiment, with respect to the compounds of formulae VIIa-VIIf, $R^{5b}$ is H, in another embodiment, $R^{5b}$ is Me.

In another particular embodiment, with respect to the compounds of formula I, the compound is according to formula VIIIa, VIIIb, or VIIIc:

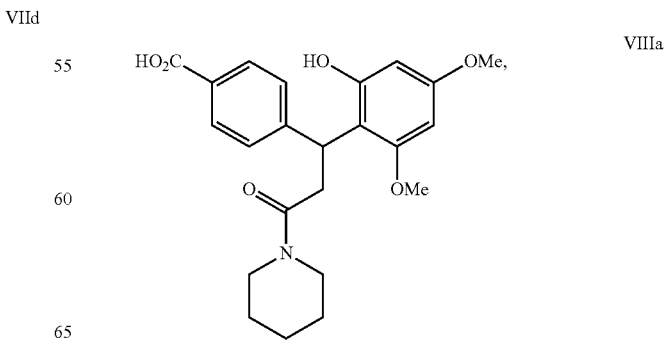
VIIIa

VIIIb

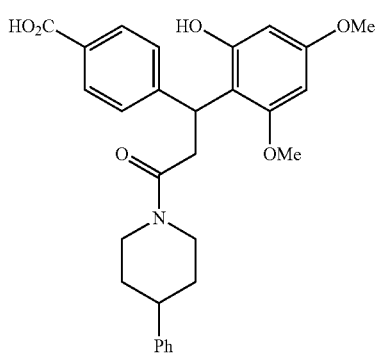

or

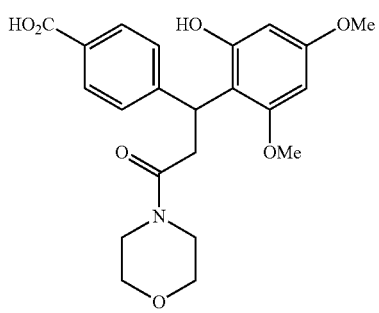

VIIIc or a pharmaceutically acceptable salt, solvate or prodrug thereof;

or stereoisomers, isotopic variants and tautomers thereof.

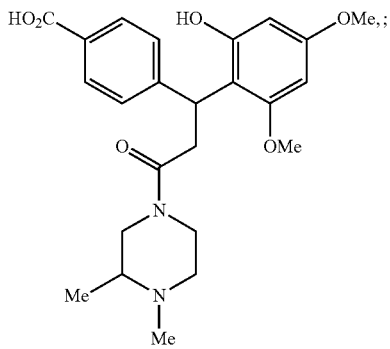

IXc

In one particular embodiment, with respect to the compounds of formula IXa, the compound is a sodium salt.

In one particular embodiment, with respect to the compounds of formula I-III, the compound is according to formula Xa, Xb, or Xc:

or a pharmaceutically acceptable salt, solvate or prodrug thereof;

or stereoisomers, isotopic variants and tautomers thereof.

In one particular embodiment, with respect to the compounds of formula I, the compound is according to formula IXa IXb, or IXC:

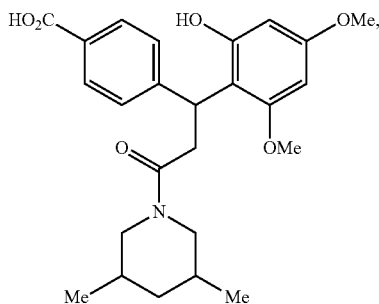

IXa

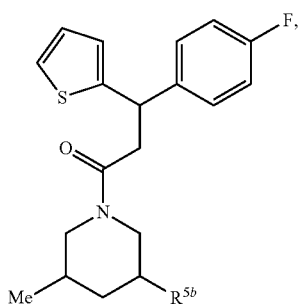

Xa

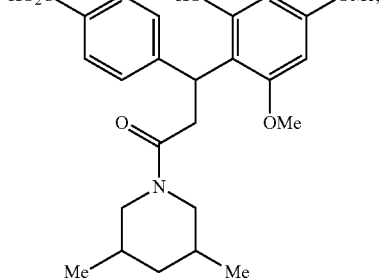

IXb

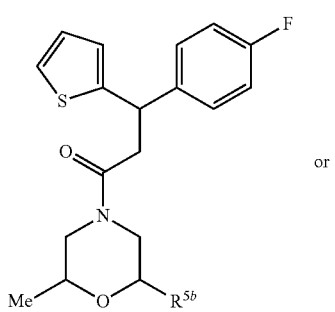

Xb or

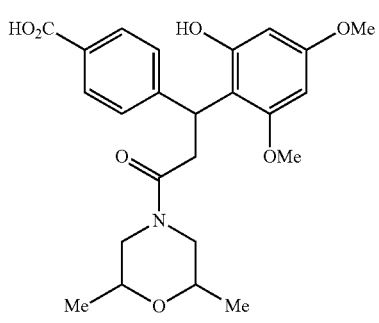

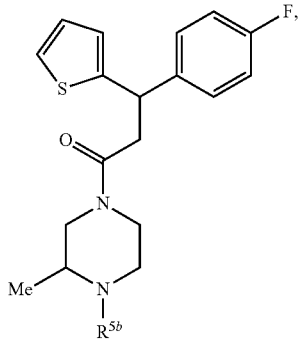

Xc and wherein $R^{5b}$ is H or Me;
or a pharmaceutically acceptable salt, solvate or prodrug thereof;
or stereoisomers, isotopic variants and tautomers thereof.

In one particular embodiment, with respect to the compounds of formula I-III, the compound is according to formula XIa, XIb, or XIc:

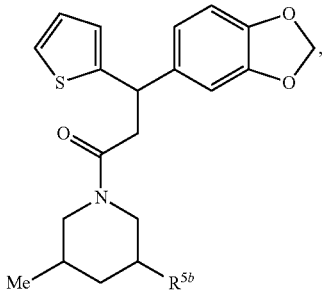

XIa

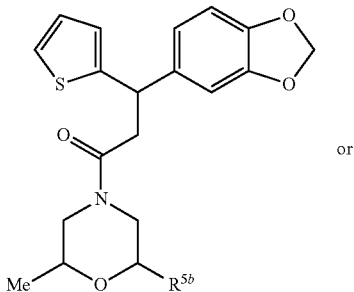

XIb or

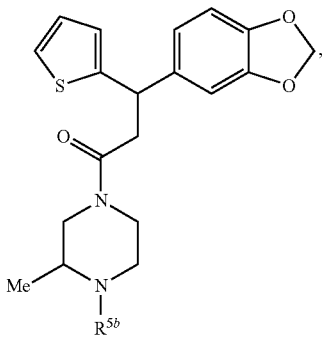

XIc and wherein $R^{5b}$ is H or Me;
or a pharmaceutically acceptable salt, solvate or prodrug thereof;
or stereoisomers, isotopic variants and tautomers thereof.

In one particular embodiment, with respect to the compounds of formula I-III, the compound is according to formula XIIa, XIb, or XIIc:

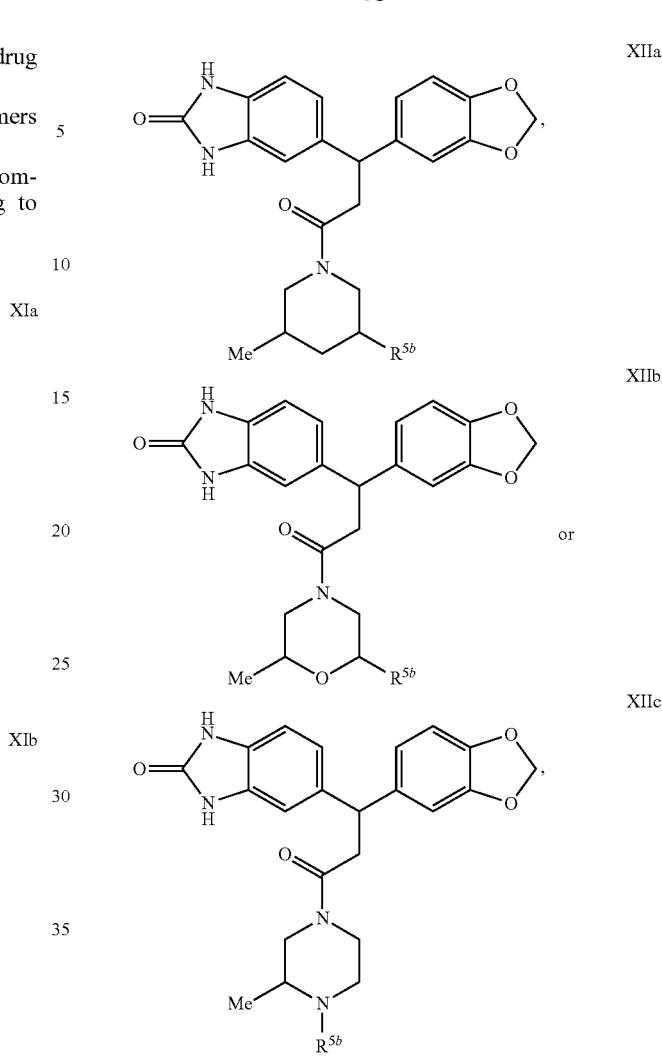

and wherein $R^{5b}$ is H or Me;
or a pharmaceutically acceptable salt, solvate or prodrug thereof;
or stereoisomers, isotopic variants and tautomers thereof.

In certain embodiments, the invention provides compounds according to formula Xa, Xb, Xc, XIa, XIb, XIc, XIIa, XIIb, or XIIc.

In certain embodiments, with respect to the method of the invention, the compound is according to formula I; and the compound is Compound 99, or 101 (Table 1).

In certain embodiments, with respect to the method of the invention, the compound is according to formula I; and the compound is Compound 95, 100, 111, or 139 (Table 1).

In certain embodiments, the invention provides composition of matter for compounds Compound 95, 99, 100, 101, 111, or 139 (Table 1).

In one particular embodiment, with respect to the compounds of formula I, the compound is any one of the compounds listed in Table 1.

In one particular embodiment, with respect to the compounds of formula I, the compound is any one of the compounds listed in Table 1, Table 1A, and Table 1B; and wherein the Compound ID is 70, 79 106-108, 142, 202-206, 301-349 or 350.

In one particular embodiment, with respect to the compounds of formula I, the compound is any one of the compounds listed in Table 1A; and wherein the Compound ID is 202.

In one particular embodiment, with respect to the compounds of formula I, the compound is a sodium salt of Compound 201 or 202.

In one particular embodiment, with respect to the compounds of formula I, the compound is any one of the compounds listed in Table 1C.

In another aspect, the present invention provides pharmaceutical composition of a compound according to formulae I-XIIc.

In one particular aspect, the present invention provides composition of matter and pharmaceutical composition of the compounds according to formula IIIa.

In one particular aspect, the present invention provides composition of matter and pharmaceutical composition of the compounds according to formula IIIb.

In one particular aspect, the present invention provides composition of matter and pharmaceutical composition of the compounds according to formula IIIc.

In one particular aspect, the present invention provides composition of matter and pharmaceutical composition of the compounds according to formula IVa-IVf.

In one particular aspect, the present invention provides composition of matter and pharmaceutical composition of the compounds according to formula Va-Vf.

In one particular aspect, the present invention provides composition of matter and pharmaceutical composition of the compounds according to formula VIa-VIf.

In one particular aspect, the present invention provides composition of matter and pharmaceutical composition of the compounds according to formula VIIa-VIIf.

In one particular aspect, the present invention provides composition of matter and pharmaceutical composition of the compounds according to formula VIIIa-VIIIc.

In one particular aspect, the present invention provides composition of matter and pharmaceutical composition of the compounds according to formula IXa-IXc.

In one particular aspect, the present invention provides composition of matter and pharmaceutical composition of the compounds according to formula Xa-Xc.

In one particular aspect, the present invention provides composition of matter and pharmaceutical composition of the compounds according to formula XIa-XIc.

In one particular aspect, the present invention provides composition of matter and pharmaceutical composition of the compounds according to formula XIIa-XIIc.

In one particular aspect, the present invention provides composition of matter and pharmaceutical composition of the compounds listed in Table 1A, 1B, or 1C; or a pharmaceutically acceptable salt, solvate or prodrug thereof; or stereoisomers, isotopic variants and tautomers thereof.

In one embodiment, with respect to the method of treatment, the disease or condition is autoimmune disease.

In one embodiment, with respect to the method of treatment, the disease or condition is inflammatory disease.

In one embodiment, with respect to the method of treatment, the disease or condition is selected from arthritis, diabetes, multiple sclerosis (and the animal model thereof, EAE), uveitis, rheumatoid arthritis (and the animal model thereof, CIA), psoriasis, asthma, bronchitis, allergic rhinitis, chronic obstructive pulmonary disease, atherosclerosis, cancer, graft-versus-host disease, H. pylori infections and ulcers resulting from such infection, and inflammatory bowel diseases.

In one embodiment, with respect to the method of treatment, the disease or condition is selected from Crohn's disease, ulcerative colitis, sprue and food allergies.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Pharmaceutical Compositions

When employed as pharmaceuticals, the compounds of this invention are typically administered in the form of a pharmaceutical composition. Such compositions can be prepared in a manner well known in the pharmaceutical art and comprise at least one active compound.

Generally, the compounds of this invention are administered in a pharmaceutically effective amount. The amount of the compound actually administered will typically be determined by a physician, in the light of the relevant circumstances, including the condition to be treated, the chosen route of administration, the actual compound-administered, the age, weight, and response of the individual patient, the severity of the patient's symptoms, and the like.

The pharmaceutical compositions of this invention can be administered by a variety of routes including oral, rectal, transdermal, subcutaneous, intravenous, intramuscular, and intranasal. Depending on the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences*, 17th edition, 1985, Mack Publishing Company. Easton, Pa., which is incorporated herein by reference.

The compounds of this invention can also be administered in sustained release forms or from sustained release drug delivery systems. A description of representative sustained release materials can be found in *Remington's Pharmaceutical Sciences*.

The following formulation examples illustrate representative pharmaceutical compositions of this invention. The present invention, however, is not limited to the following pharmaceutical compositions.

Formulation 1—Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active amide compound per tablet) in a tablet press.

Formulation 2—Capsules

A compound of the invention is admixed as a dry powder with a starch diluent in an approximate 1:1 weight ratio. The mixture is filled into 250 mg capsules (125 mg of active amide compound per capsule).

Formulation 3—Liquid

A compound of the invention (125 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of the invention is admixed as a dry powder with a dry gelatin binder in an approximate 1:2 weight ratio. A minor amount of magnesium stearate is added as a lubricant. The mixture is formed into 450-900 mg tablets (150-300 mg of active amide compound) in a tablet press.

Formulation 5—Injection

A compound of the invention is dissolved or suspended in a buffered sterile saline injectable aqueous medium to a concentration of approximately 5 mg/ml.

Formulation 6—Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present compounds are used as therapeutic agents for the treatment of conditions in mammals that are causally related or attributable to RORγt activity. Accordingly, the compounds and pharmaceutical compositions of this invention find use as therapeutics for preventing and/or treating a variety of inflammatory conditions and autoimmune disorders in mammals, including humans.

In a method of treatment aspect, this invention provides a method of treating a mammal susceptible to or afflicted with a condition associated with an inflammatory condition and/ or an autoimmune disorder, which method comprises administering an effective amount of one or more of the pharmaceutical compositions just described.

In additional method of treatment aspects, this invention provides methods of treating a mammal susceptible to or afflicted with an inflammatory condition or autoimmune disorder causally related or attributable to RORγt activity. Such condition and disorders include, without limitation, arthritis, diabetes, multiple sclerosis (and the animal model thereof, EAE), uveitis, rheumatoid arthritis (and the animal model thereof, CIA), psoriasis, asthma, bronchitis, allergic rhinitis, chronic obstructive pulmonary disease, atherosclerosis, cancer, graft-versus-host disease, *H. pylori* infections and ulcers resulting from such infection, and inflammatory bowel diseases. Such methods comprise administering an effective condition-treating or condition-preventing amount of one or more of the pharmaceutical compositions just described.

The present inventors have shown that treatment of wild-type cells with RORγt inhibitor digoxin resulted in changes in gene expression that were very similar to those observed in RORγt-deficient cells. See Huh et al. (2011) Digoxin and its derivatives suppress Th17 cell differentiation by antagonizing RORγt activity; *Nature* 472, 486-490 (28 Apr. 2011), the entire contents of which is incorporated herein by reference. That being the case, RORγt inhibitors can be used to treat any diseases caused by RORγ or RORγt expressing cells, including Th17, NK22, and other innate lymphoid cells. The pro-atherogenic contribution of IL-17 to atherosclerotic lesions, for example, suggests that atherosclerosis can be treated efficaciously with the compounds and compositions described herein. See Chen et al. J Innate Immun. 2010; 2(4):325-33. Epub 2010 May 7, the entire contents of which is incorporated herein by reference.

As a further aspect of the invention there is provided the present compounds for use as a pharmaceutical especially in the treatment or prevention of the aforementioned conditions and diseases. Also provided herein is the use of the present compounds in the manufacture of a medicament for the treatment or prevention of one of the aforementioned conditions and diseases.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as, e.g., arthritis, diabetes, multiple sclerosis (and the animal model thereof, EAE), rheumatoid arthritis (and the animal model thereof, CIA), psoriasis, or asthma, the regimen for treatment usually stretches over many months or years, so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound of the invention, with preferred doses each providing from about 0.1 to about 10 mg/kg and especially about 1 to about 5 mg/kg.

Transdermal doses are generally selected to provide similar or lower blood levels than are achieved using injection doses. Modes of administration suitable for mucosal sites are also envisioned herein and include without limitation: intra-anal swabs, enemas, intranasal sprays, and aerosolized or vaporized compounds and/or compositions for delivery to the lung mucosa. One of skill in the art would choose an appropriate delivery models based on a variety of parameters, including the organ or tissue site in a patient with a disease or condition that is most severely affected by the disease or condition. A skilled practitioner could, for example, treat a patient afflicted with an inflammatory bowel disease (IBD) with a therapeutic regimen that included delivery of the compounds or compositions of the invention using an enema for direct delivery to the bowel.

When used to prevent the onset of an inflammatory condition or autoimmune disorder, the compounds of this invention will be administered to a patient at risk for developing the condition or disorder, typically on the advice and under the supervision of a physician, at the dosage levels described above. Patients at risk for developing a particular condition generally include those that have a family history of the condition, or those who have been identified by genetic testing or screening to be particularly susceptible to developing the condition.

The compounds of this invention can be administered as the sole active agent or they can be administered in combination with other agents, including other compounds that demonstrate the same or a similar therapeutic activity and are determined to safe and efficacious for such combined administration.

General Synthetic Procedures

The amido compounds of this invention may be purchased from various commercial sources or can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds of the invention may be prepared from known or commercially available starting materials and reagents by one skilled in the art of organic synthesis.

General Materials and Methods:

All commercially available reagents and solvents were purchased and used without further purification. All microwave reactions were carried out in a sealed microwave vial equipped with a magnetic stir bar and heated in a Biotage Initiator Microwave Synthesizer. HPLC purification was performed using a Waters semi-preparative HPLC equipped with a Phenomenex Luna® C18 reverse phase (5 micron, 30×75 mm) column (unless state otherwise) having a flow rate of 45 mL/min. The mobile phase was a mixture of acetonitrile and $H_2O$ each containing 0.1% trifluoroacetic acid. $^1H$ spectra were recorded using either an Inova 400 MHz spectrometer (Varian) or an Inova 300 MHz spectrometer (Varian). Two LCMS methods were used to analyze samples' purity. Method 1: Agilent 1200 series LC/MS equipped with a Zorbax™ Eclipse XDB-C18 reverse phase (5 micron, 4.6×150 mm) column having a flow rate of 1.1 mL/min. The mobile phase was a mixture of acetonitrile and $H_2O$ each containing 0.05% trifluoroacetic acid. A gradient of 5% to 100% acetonitrile over 8 minutes was used during analytical analysis. Method 2: Acquity HPLC equipped with a Waters BEH C18, 1.7 micron, 2.1×50 mm column; Column Temperature: 45 degrees C.; Flow: 0.5 mL/min; Solvent A: 0.05% TFA in Water; Solvent B: 0.025% TFA in Acetonitrile; Gradient: 2% to 100% Solvent B over 1.3 minutes; Run Time-3 min. High-resolution mass spectroscopy measurements were performed on a Agilent 6210 Electrospray TOF mass spectrometer.

The following general procedures were used to synthesize compounds having different but analogous structures. One skilled in the art of synthesis will recognize how to modify these general procedures if necessary to accomplish the desired transformations.

Representative Synthetic Methods

Method A

The representative hydroxy compounds of the invention can be prepared using the general synthetic pathway depicted in Scheme 1.

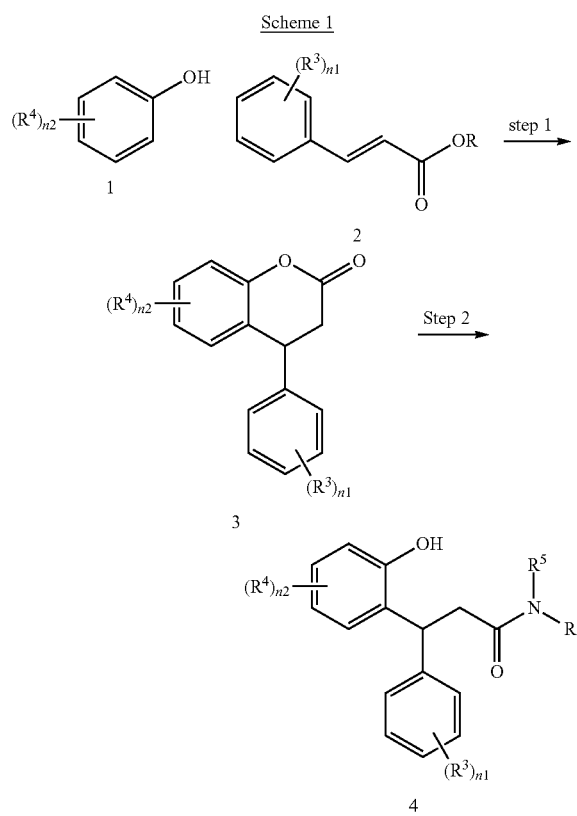

The following reaction conditions were used for step 1:
(1) TFA, 60-100° C., 2-16 h
or (2) p-toluenesulfonic acid, 125° C., 2 h The following reaction conditions were used for step 2:
(1) $R^5R^6NH$, 60-80° C., DMA or THF, 2-16 h
or (2) $R^5R^6NH$, $Me_3Al$, Toluene/DCE, 50° C., 4-12 h and wherein $R^3$, $R^4$, $R^5$, $R^6$, $n1$ and $n2$ are as described herein.

Step 1:

A mixture of phenol (1, 0.2 mmol) and cinnamic acid (2, 0.2 mmol) in TFA (2 mL) was heated at 60-100° C. for 2-16 h. Upon completion. TFA was removed using a Genevac evaporator and the residue was dissolved in DCM (2 mL), washed with saturated $NaHCO_3$ (2 mL). After removing solvent, the intermediate compound 3 was obtained. The intermediate compound 3 may be prepared using the following procedure.

A mixture of (1, 0.2 mmol), cinnamic acid (2, 0.2 mmol) and p-toluenesulfonic acid (0.2 mmol) was heated at 125° C. for 2 h. The reaction mixture was cooled to room temperature and dissolved in DCM (2 mL), washed with NaOH (1 M, 1 mL). After removing solvent, the intermediate compound 3 was obtained and used for next step without further purification.

Step 2:

A mixture of 3 (0.2 mmol) and amine ($R^5R^6NH$, 0.3 mmol) in DMA or THF (2 mL) was heated at 60-80° C. for 2-16 h. Upon completion, the mixture was cooled to room temperature. The desired product 4 was obtained by HPLC purification. The compound 4 may be prepared using the following procedure.

To an 8 mL-vial, amine (R5R6NH, 0.3 mmol) was added. The vial was capped with a Teflon cap, and then $Me_3Al$ (0.4 mL, 1M in heptane) was added. The resulting mixture was shaken at room temperature for 1 h. This was followed by addition of 3 (0.2 mmol, dissolved in 1 mL dry toluene/or DCE). The resulting mixture was heated at 50° C. for 12 h. The reaction mixture was cooled to room temperature and concentrated in a GeneVac. The residue was dissolved in DCM (2 mL), and then $Na_2SO_4.10H_2O$ (0.2 mmol, 32 mg) was added. The suspension was vortexed and centrifuged, the clean solution was separated and concentrated. The crude product was purified by HPLC to afford 4.

Method B

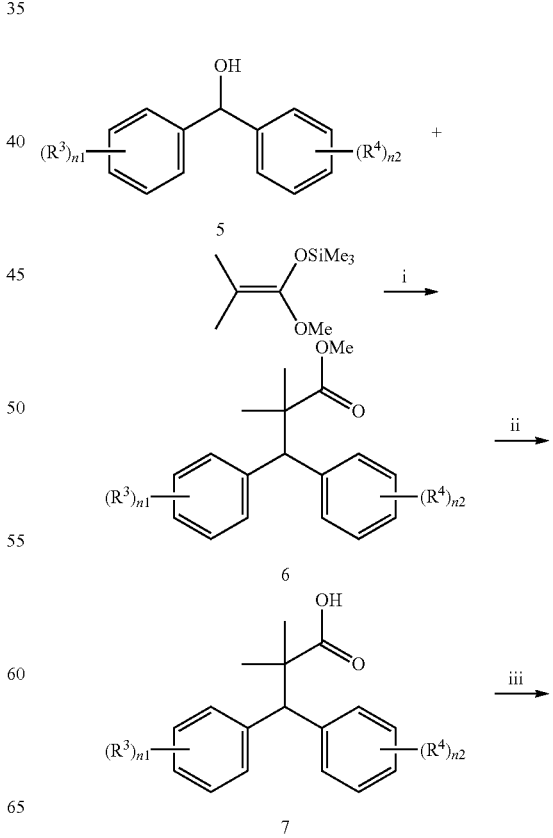

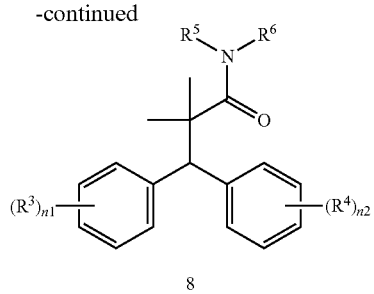

8

Reaction conditions: (i) BF₃Et₂O, 0° C.-r.t. 1-2 h; (ii) LiOH, THF/H₂O/MeOH, MW, 150° C., 1 h; (iii) DMC, R⁵R⁶NH, Hunig base, CH₂Cl₂ and wherein R³, R⁴, R⁵, R⁶, n1 and n2 are as described herein.

General Procedure

To a solution of 5 (1 mmol) and (1-methoxy-2-methyl-prop-1-enyloxy)trimethylsilane (1.5 mmol) in 10 mL of DCM at 0° C. was added BF₃Et₂O (1.5 mmol) with stirring. The mixture was warmed to r.t. and stirring was continued for 1-2 h. Upon completion, 20 mL DCM was added and the organic layer was washed with sat Na₂CO₃ solution (10 mL) and water (10 mL), dried over MgSO₄ and concentrated. The residue was purified by column chromatography over silica-gel to give 6. A solution of 6 (0.5 mmol) and LiOH (5 mmol) in a mixture of solvents (10 mL THF, 5 mL MeOH and 5 mL water) was heated in a microwave at 150° C. for 1 h. Upon completion, the solvent was removed. The residue was dissolved in 10 mL of water and the solution was acidified by 1 M HCl to pH=2. The resulting mixture was extracted with DCM (3×30 mL). The combined organic layers was dried over MgSO₄, filtered and concentrated to give acid 7. To a solution of acid 7 (0.3 mmol) and Hunig base (1 mmol) in DCM (10 mL) was added 2-chloro-1,3-dimethylimidazo-linium chloride (1.5 mmol) at room temperature. After stirring for 10 min, a solution of amine (0.6 mmol R₃R₄NH in DCM or DMA) was added. The resulted mixture was stirred for 4-12 h. After concentrated, the residue was purified by HPLC to yield the desired 8.

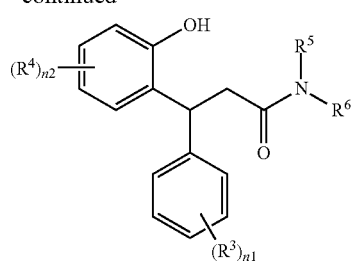

4

Reaction conditions: (i) TFA, CH₂Cl₂Pd(OAc)₂, 40° C., 8 h; (ii) R⁵R⁶NH, MeOH, HCO₂NH₄, 10% Pd/C, 50° C., 8 h and wherein R³, R⁴, R⁵, R⁶, n1 and n2 are as described herein.

General Procedure:

Compound 2 was either used without purification from commercial sources or synthesized following the literature procedure (Xie, L. et al., *J. Med. Chem.* 1999, 42, 2662.)

A solution of 2 (1 mmol) in CH₂Cl₂ (0.9 mL) was treated with phenol 1 (1 mmol), TFA (2.7 mL) and Pd(OAc)₂ (15 mg, 0.069 mmol), and stirred at 40° C. for 8 h. The reaction mixture was concentrated to dryness using the Genevac evaporator and used crude in the next step.* Crude 9 was dissolved in MeOH (1 mL), treated with R5R6NH (2 mmol), 10% Pd/C (8 mg, 0.1 mmol) and ammonium formate (67 mg, 1 mmol) and heated to 50° C. for 8 h. The reaction mixture was diluted with MeOH, filtered through a solid supported thiol column, and concentrated under reduced pressure. The material was purified by HPLC to yield compound 4.

*The degree of oxidation to 9 was substrate dependent and sometimes the primary product was lactone 3 as determined by LCMS. If the level of oxidation was <20%, amide 4 was synthesized following the same conditions described in Method A.

Method D

Method C

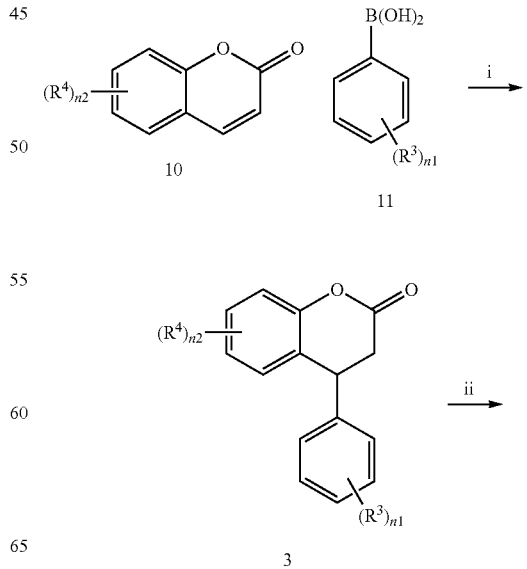

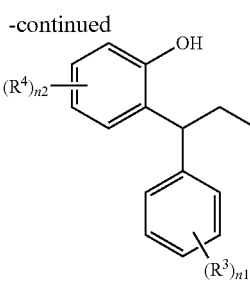

4

Reaction conditions: (i) Pd(OAc)₂, BIPY, AcOH, H₂O, THF, 60° C., 8 h; (ii) R⁵R⁶NH, DMA, 80° C., 8 h and wherein R³, R⁴, R⁵, R⁶, n1 and n2 are as described herein.

General Procedure

A suspension of coumarin 10 (0.15 mmol), boronic acid 11 (0.4 mmol) BIPY (10 mg, 0.064 mmol), and Pd(OAc)₂ (7 mg, 0.03 mmol) in AcOH (0.6 mL), THF (0.2 mL) and H₂O (0.1 mL) was heated to 60° C. for 8 h and concentrated to dryness in the Genevac evaporator to afford 3 which was used without purification in the following step. Crude lactone 3 was converted to amide 4 following the same protocol as Method A (NHR5R6, DMA, 80° C.) and purified with HPLC to afford product 4.

Method E

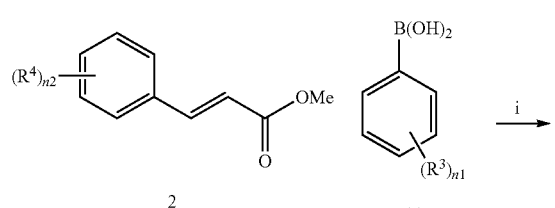

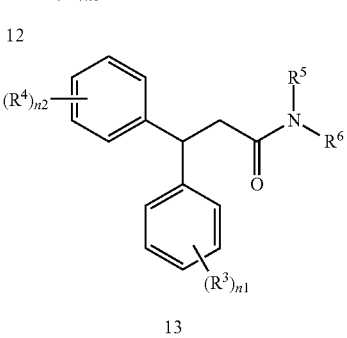

13

Reaction conditions: (i) Pd(OAc)₂, BIPY, AcOH, H₂O, THF, 60° C., 8 h; (ii) R⁵R⁶NH, 2,3,4,6,7,8-hexahydro-1H-pyrimido[1,2-a]pyrimidine, 70° C., 8 h and wherein R³, R⁴, R⁵, R⁶, n1 and n2 are as described herein.

General Procedure:

A suspension of cinnamic ester 2 (0.15 mmol), boronic acid 11 (0.4 mmol) BIPY (10 mg, 0.064 mmol), and Pd(OAc)₂ (7 mg, 0.03 mmol) in AcOH (0.6 mL), THF (0.2 mL) and H₂O (0.1 mL) was heated to 60° C. for 8 h and concentrated to dryness in the Genevac evaporator to afford 12 which was used without purification in the following step. Crude 12 was treated with 2,3,4,6,7,8-hexahydro-1H-pyrimido[1,2-a]pyrimidine (0.18 mmol) and R5R6NH and heated to 70° C. for 8 h. The reaction mixture was purified by HPLC to afford 13.

Method F

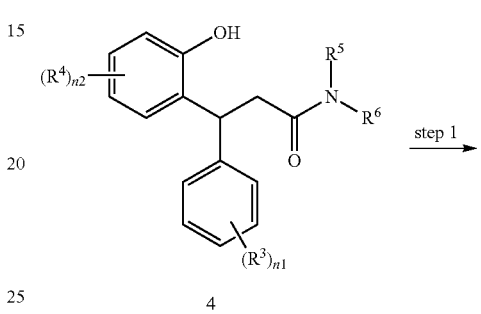

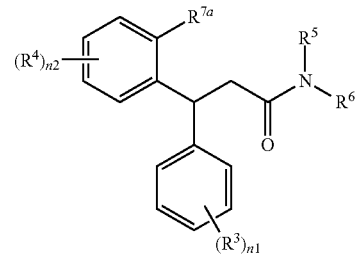

14 and wherein R³, R⁴, R⁵, R⁶, n1 and n2 are as described herein.

General Procedure:

A mixture of 4 (0.1 mmol) and NaH (0.2 mmol) was dissolved in dry THF (2 mL). After stirring at room temperature for 0.5 h, alkyl halide (0.4 mmol) was added. The resulting mixture was heated at 60° C. for 2-8 h. The solution was cooled to room temperature. A couple drops of water were added and the mixture was purified by HPLC to give compound 14.

Method G

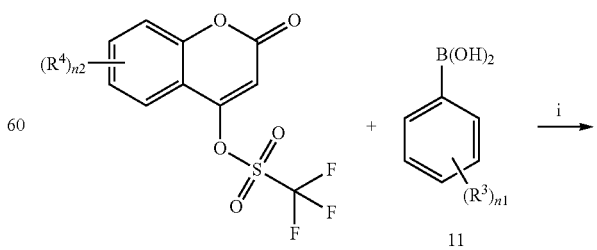

Z01

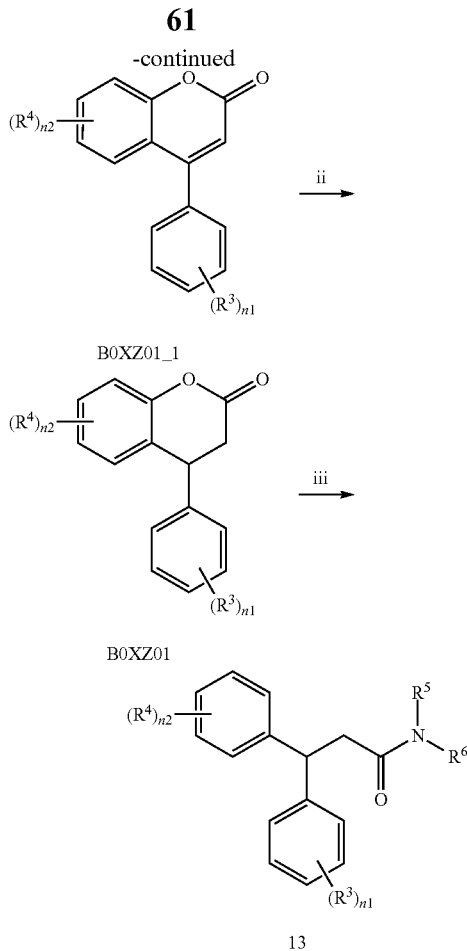

Reaction Conditions: (i) TBAB, K$_3$PO$_4$, PD(dppf)$_2$Cl$_2$ (ii) Pd/H$_2$; (iii) R$^5$R$^6$NH, 60° C., THF and wherein R$^3$, R$^4$, R$^5$, R$^6$, R$^{7a}$, $n1$ and $n2$ are as described herein.

General Procedure:
Step 1

A suspension of 4-trifluoromethylsulfonyloxy coumarin Z01 (0.3 mmol, 1.0 eq.), boronic acid 11 (0.33 mmol, 1.1 eq.), potassium phosphate (3.0 eq.), tetrabutylamoniumbromid (0.1 eq.), and 1,1'-bis(diphenylphosphino)ferocene-palladium(II)dichloride dichloromethane complex (0.1 eq.) in acetonitrile/H$_2$O (3.5 mL:0.5 mL), was refluxed under nitrogen until the substrate was completely consumed (12 h, monitored by LCMS or TLC). The reaction mixture was diluted with water and extracted with dichloromethane. The combined organic layers were dried over anhydrous Na$_2$SO$_4$, and the solvent was removed under reduced pressure. The residue was purified by TLC (EtOAc/petroleum=3:2) or by prep-HPLC, to afford the intermediate B0XZ01-1.

Step 2

The intermediate B0XZ01-1 (1.0 eq.) was dissolved in 5 mL EtOAc, Pd/C (ca. 7-10 mg, 20%) was added and the mixture was stirred at rt. for 12 hours under H$_2$ balloon. The reaction was monitored by LCMS. The stirring is continued until the double bond was reduced completely. The catalyst Pd/C was filtered off, and the solvent was removed under reduced pressure to afford the crude B0XZ01 which was used as such for the next step.

Step 3

The intermediate B0XZ01 (1.0 eq.) and amine (R$^5$R$^6$NH, 1.1 eq.) were dissolved in 2.5 mL of THF, the reaction mixture was stirred at 60° C. for 5 hours. The solvent was removed under reduced pressure to afford the crude product 13. The crude product was then purified by prep-HPLC, to afford the desired product 13.

Synthesis of the Heteroaryl Compounds of the Invention

The representative heteroaryl compounds of the invention can be prepared following the general synthetic pathways and synthetic methods described above; and replacing the group

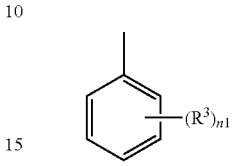

with the appropriate HET$^1$ group.

REPRESENTATIVE EXAMPLES

Compound 83 Method D 1-(3,5-Dimethylpiperidin-1-yl)-3-(2-hydroxy-4,6-dimethoxyphenyl)-3-(3-(methylsulfonyl)phenyl)propan-1-one (Compound 83, Table 1)

Prepared by method D: $^1$H NMR (400 MHz, DMSO-d$_6$) δ ppm 9.54 (d, J=9.19 Hz, 1 H) 7.77 (s, 1 H) 7.64-7.68 (m, 1 H) 7.51-7.56 (m, 1 H) 7.47 (t, J=7.73 Hz, 1 H) 5.99-6.06 (m, 2 H) 5.02-5.10 (m, 1 H) 4.31 (d, J=13.11 Hz, 1 H) 3.74-3.82 (m, 1 H) 3.67 (d, J=1.76 Hz, 3 H) 3.65 (s, 3 H) 3.35-3.47 (m, 1 H) 3.19-3.26 (m, 1 H) 3.12-3.15 (m, 3 H) 2.99-3.10 (m, 1 H) 2.83-2.95 (m, 1 H) 1.84-1.93 (m, 1 H) 1.63-1.75 (m, 1 H) 1.13-1.35 (m, 2 H) 0.69-0.90 (m, 6 H); LCMS: (electrospray+ve), m/z 476.2 (MH)$^+$; HPLC: t$_R$=5.63 min, UV$_{254}$=99%.

Compound 99 Method D 4-(3-(3,5-Dimethylpiperidin-1-yl)-1-(2-hydroxy-4,6-dimethoxyphenyl)-3-oxopropyl)benzoic acid (Compound 99, Table 1)

$^1$H NMR (400 MHz, DMSO-d$_6$) δ ppm 0.57-0.74 (m, 1 H) 0.73-0.92 (m, 6 H) 1.06-1.48 (m, 2 H) 1.57-1.77 (m, 1 H) 1.88 (t, J=12.0 Hz, 1 H) 2.85-3.37 (m, 2 H) 3.65 (s, 6 H) 3.70-3.86 (m, 1 H) 4.30 (d, J=12.5 Hz, 1 H) 5.00 (t, J=7.1 Hz, 1 H) 5.98-6.04 (m, 2 H) 7.31 (dd, J=7.6, 5.3 Hz, 2 H) 7.76 (d, J=8.2 Hz, 2 H) 9.44 (br. s., 1 H); LC-MS: LCMS: (electrospray +ve), m/z 442.3 (MH)$^+$; t$_R$=4.49 min, UV$_{254}$=95%.

Compound 100 Method D 3-(4-Acetylphenyl)-1-(3,5-dimethylpiperidin-1-yl)-3-(2-hydroxy-4,6-dimethoxyphenyl)propan-1-one (Compound 100, Table 1)

Prepared by method D: $^1$H NMR (400 MHz, DMSO-d$_6$) δ ppm 9.42-9.47 (m, 1H) 7.78 (d, J=8.22 Hz, 2 H) 7.33 (d, J=8.22 Hz, 2 H) 5.98-6.05 (m, 2 H) 4.99-5.04 (m, 1 H) 4.31 (d, J=15.06 Hz, 1 H) 3.74-3.80 (m, 1 H) 3.62-3.70 (m, 6 H) 3.14-3.25 (m, 1 H) 3.09 (d, J=9.59 Hz, 1 H) 2.96 (d, J=9.00 Hz, 1 H) 2.55 (d, J=3.91 Hz, 1 H) 2.52 (s, 3 H) 1.85-1.94 (m, 1 H) 1.63-1.76 (m, 1 H) 1.20-1.28 (m, 2 H) 0.64-0.90 (m, 6 H); LCMS: (electrospray +ve), m/z 440.2 (MH)$^+$; HPLC: $t_R$=5.92 min, UV$_{254}$=90%.

Compound 101 Method D 3-(3-(3,5-Dimethylpiperidin-1-yl)-1-(2-hydroxy-4,6-dimethoxyphenyl)-3-oxopropyl)benzoic acid (Compound 101, Table 1)

Prepared by method D: $^1$H NMR (400 MHz, DMSO-d$_6$) δ ppm 12.73 (br. s., 1 H) 9.44-9.48 (m, 1 H) 7.82-7.89 (m, 1 H) 7.65 (d, J=7.63 Hz, 1 H) 7.46 (t, J=9.68 Hz, 1 H) 7.27-7.33 (m, 1 H) 6.00-6.04 (m, 2 H) 4.97-5.03 (m, 1 H) 4.31 (d, J=15.45 Hz, 1 H) 3.73-3.81 (m, 1 H) 3.67 (d, J=4.69 Hz, 3 H) 3.65 (s, 3 H) 3.12-3.24 (m, 1 H) 2.98 (dd, J=13.79, 7.92 Hz, 1 H) 2.76-2.89 (m, 1 H) 2.37-2.47 (m, $_{1H}$) 1.84-1.92 (m, 1 H) 1.62-1.74 (m, 1 H) 1.24 (s, 2 H) 0.71-0.91 (m, 6 H); LCMS: (electrospray +ve), m/z 442.2 (MH)$^+$; HPLC: $t_R$=5.51 min, UV$_{254}$=98%.

Compound 106 Method D 1-(3,5-Dimethylpiperidin-1-yl)-3-(2-hydroxy-4,6-dimethoxyphenyl)-3-(pyridin-3-yl)propan-1-one (Compound 106, Table 1)

$^1$H NMR (400 MHz, DMSO-d$_6$) δ ppm 9.46-9.49 (m, 1 H) 7.15 (d, J=5.09 Hz, 1 H) 6.79-6.83 (m, 1 H) 6.74-6.78 (m, 1 H) 6.03 (dq, J=4.35, 2.20 Hz, 2 H) 5.13-5.24 (m, 1 H) 4.33 (d, J=12.13 Hz, 1 H) 3.72-3.79 (m, 1 H) 3.70 (d, J=5.48 Hz, 3 H) 3.66 (s, 3 H) 3.12 (d, J=7.04 Hz, 1 H) 2.82-3.02 (m, 1 H) 2.41 (td, J=12.33, 7.04 Hz, 1 H) 1.84-1.92 (m, 1 H) 1.62-1.72 (m, 1 H) 1.11-1.37 (m, 3 H) 0.63-0.84 (m, 6 H); LC-MS: (electrospray +ve), m/z 399.2 (MH)$^+$ $t_R$=4.31 min, UV$_{254}$=90%.

Compound 107 Method A 1-(3,5-Dimethylpiperidin-1-yl)-3-(2-hydroxy-4,6-dimethoxyphenyl)-3-(thiophen-2-yl)propan-1-one (Compound 107, Table 1)

$^1$H NMR (400 MHz, DMSO-d$_6$) δ ppm 9.46-9.49 (m, 1 H) 7.15 (d, J=5.09 Hz, 1 H) 6.79-6.83 (m, 1 H) 6.74-6.78 (m, 1 H) 6.03 (dq, J=4.35, 2.20 Hz, 2 H) 5.13-5.24 (m, 1 H) 4.33 (d, J=12.13 Hz, 1 H) 3.72-3.79 (m, 1 H) 3.70 (d, J=5.48 Hz, 3 H) 3.66 (s, 3 H) 3.12 (d, J=7.04 Hz, 1 H) 2.82-3.02 (m, 1 H) 2.41 (td, J=12.33, 7.04 Hz, 1 H) 1.84-1.92 (m, 1 H) 1.62-1.72 (m, 1 H) 1.11-1.37 (m, 3 H) 0.63-0.84 (m, 6 H); LC-MS: (electrospray +ve), m/z 404.2 (MH)$^+$ $t_R$=6.13 min, UV$_{254}$=98%.

Compound 108 Method D 1-(3,5-Dimethylpiperidin-1-yl)-3-(2-hydroxy-4,6-dimethoxyphenyl)-3-(pyridin-4-yl)propan-1-one (Compound 108, Table 1)

$^1$H NMR (400 MHz, DMSO-d$_6$) δ 9.49 (d, J=5.87 Hz, 1 H) 8.34 (d, J=6.26 Hz, 2 H) 7.14 (d, J=5.09 Hz, 2 H) 5.97-6.06 (m, 2 H) 4.91-4.98 (m, 1 H) 4.32 (d, J=16.82 Hz, 1 H) 3.73-3.84 (m, 1 H) 3.66 (s, 6 H) 3.17-3.27 (m, 1 H) 2.91-3.07 (m, 2 H) 2.36-2.46 (m, 1 H) 1.86-1.94 (m, 1 H) 1.62-1.77 (m, 1 H) 1.42-1.51 (m, 2 H) 0.77-0.90 (m, 6 H); LC-MS: LCMS: (electrospray +ve), m/z 399.2 (MH)$^+$; $t_R$=4.35 min. UV$_{254}$=99%.

Compound 141 Method E 3-(4-(1H-1,2,4-Triazol-1-yl)phenyl)-3-(benzo[d][1,3]dioxol-5-yl)-1-(3,5-dimethylpiperidin-1-yl)propan-1-one 13m (NCGC00242637, 141)

Reaction Conditions: (i) Pd(OAc)$_2$, BIPY, AcOH, H$_2$O, THF, 60° C., 8 h; (ii) 3,5-dimethylpiperidine, 2,3,4,6,7,8-hexahydro-1H-pyrimido[1,2-a]pyrimidine, 70° C., 8 h Prepared by method E: A suspension of cinnamic methyl ester (2m, 224 mg, 0.97 mmol), boronic acid 11a (315 mg, 1.89 mmol) BIPY (30 mg, 0.192 mmol), and Pd(OAc)$_2$ (30 mg, 0.134 mmol) in AcOH (1.5 mL), THF (0.5 mL) and H$_2$O (0.25 mL) was heated to 60° C. for 8 h and concentrated to dryness in the Genevac evaporator to afford 12m which was used without purification in the following step. The crude methyl ester was treated with 3,5-dimethylpiperidine (1.34 mL, 9.88 mmol) and 2,3,4,6,7,8-hexahydro-1H-pyrimido[1,2-a]pyrimidine (0.134 g, 0.96 mmol) and heated to 70° C. for 8 h, the reaction mixture was purified by HPLC to afford the amide 13m. LCMS: (electrospray +ve), m/z 433.2 (MH)$^+$; HPLC: $t_R$=5.87 min, $UV_{254}$=99%.

Compound 201 Method D 4-(3-(3,5-cis-Dimethylpiperidin-1-yl)-3-oxo-1-(2,4,6-trimethoxyphenyl)-propyl)benzoic acid (NCGC00249676)

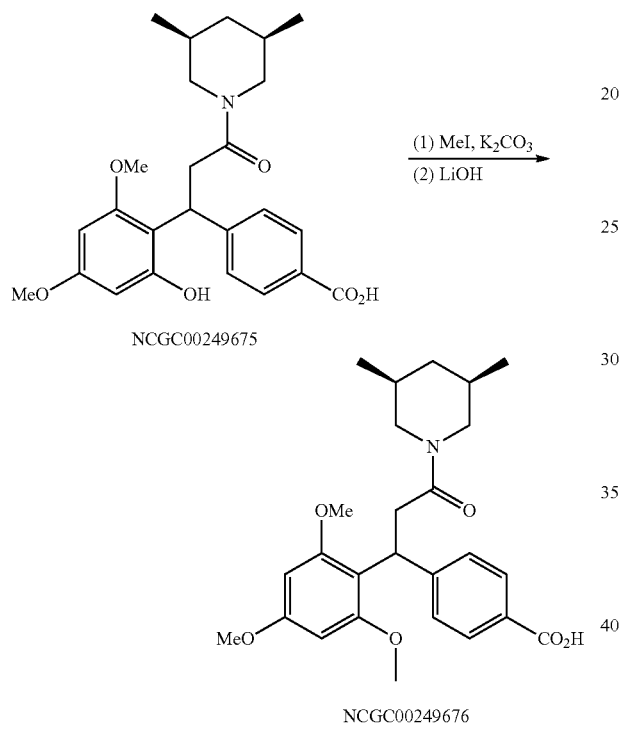

To a solution of Compound 202 (20 mg, 0.046 mmol) in 2 mL of DMF was added potassium carbonate (500 mg) and iodomethane (64 mg, 0.452 mmol). The mixture was heated at 60° C. for 8 h. The solvent was removed and the residue was dissolved in a mixed solvent (2 ml THF, 1 ml MeOH and 1 mL water). To this solution was added 4 equiv of LiOH and the mixture was stirred overnight. After removed solvent, 2 mL of water was added and the solution was acidified to pH 2 using 1.0 M HCl. The aqueous layer was extracted with 2×15 mL DCM. Combined organic layer and dried over MgSO$_4$, filtered and concentrated. The crude product was purified via column chromatography on SiO$_2$ (ethyl acetate (contain 1% acetic acid)/hexane 30%-80%) to give Compound 201 (15 mg, 73%) as a white solid.

$^1$H NMR (400 MHz, DMSO-d$_6$) δ ppm 0.62-0.78 (m, 1 H), 0.78-0.90 (m, 6 H), 1.10-1.55 (m, 2 H), 1.60-1.70 (m, 1 H), 1.82-1.95 (m, 1 H), 2.45-2.49 (m, 1H), 2.90-3.25 (m, 2 H), 3.71 (s, 3 H), 3.72 (s, 3 H), 3.76 (s, 3 H), 3.67-3.84 (m, 1 H), 4.31-4.34 (m, 1 H), 5.08 (t, J=7.4 Hz, 1 H), 6.22 (s, 1 H), 6.23 (s, 1 H), 7.27-7.33 (m, 2 H), 7.79 (d, J=8.6 Hz, 2 H), 12.64 (br. s., 1H); LC/MS: (electrospray +ve), m/z 456.2 (MH)$^+$, $t_R$=5.98 min, $UV_{254}$=100%.

Compound 202 Method D 4-(3-(3,5-cis-Dimethylpiperidin-1-yl)-1-(2-hydroxy-4,6-dimethoxyphenyl)-3-oxopropyl)benzoic acid (NCGC00249675)

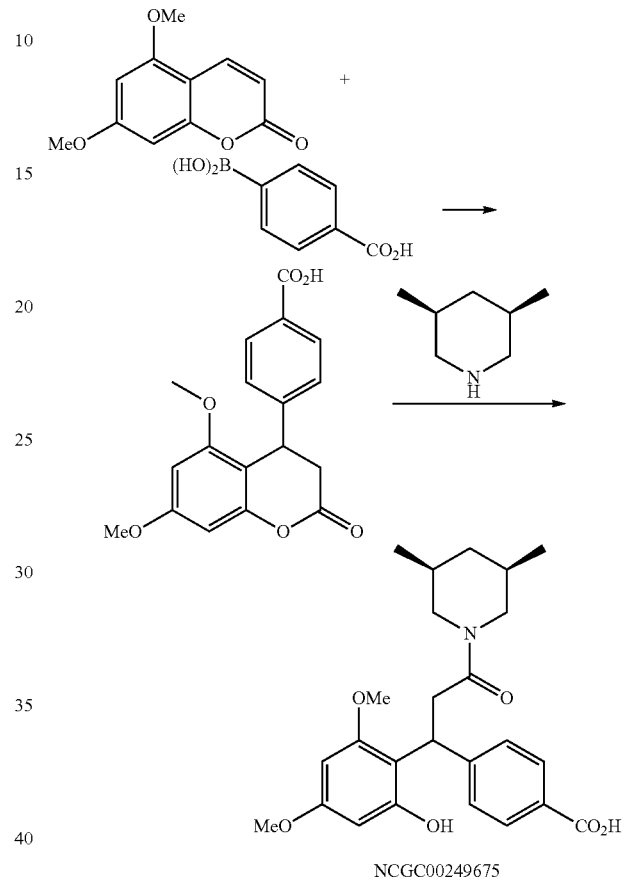

A suspension of 5,7-dimethoxy-2H-chromen-2-one (155 mg, 0.75 mmol), 4-boronobenzoic acid (622 mg, 3.75 mmol), 2,2'-bipyridine (93 mg, 0.60 mmol), and Pd(OAc)$_2$ (33 mg, 0.15 mmol) in dimethylacetamide (4.0 mL) and acetic acid (1.0 mL) was heated at 110° C. for 24 h. The reaction was concentrated under reduced pressure and the residue was dissolved in a mixture of ethyl acetate/dichloromethane (1 to 1, 20 mL). The solution was filtered through a plug of silica gel followed by flushing with ethyl acetate (contain 0.5% acetic acid). After evaporation of the solvent in vacuo, the crude product was dissolved in 4 mL of DMA followed by addition of cis-dimethylpiperidine (170 mg, 1.5 mmol). The mixture was heated at 80° C. for 6 h. The crude product was purified via column chromatography on SiO$_2$ (ethyl acetate (contain 1% acetic acid)/hexane 30%-80%) to give the pure Compound 202 as a white solid (28 mg, 8%).

$^1$H NMR (400 MHz, DMSO-d$_6$) δ ppm 0.56-0.72 (m, 1 H), 0.78 (br. S., 6 H), 1.17 (br. s., 2 H) 1.65 (br. s., 1 H), 1.86 (t, J=11.74 Hz, 1 H), 2.31-2.48 (m, 1H), 2.86-3.20 (m, 2 H), 3.63 (s, 6 H), 3.68-3.83 (m, 1 H), 4.24-4.34 (m, 1 H), 4.98 (t, J=6.26 Hz, 1 H), 6.00 (s, 2 H), 7.23-7.33 (m, 2 H), 7.74 (d, J=7.04 Hz, 2 H), 9.43 (br. s., 1H), 12.55 (br. s., 1H); LC/MS: (electrospray +ve), m/z 442.3 (MH)$^+$, $t_R$=5.60 min, $UV_{254}$=>95%.

Compound 203 Method A 1-(3,5-Dimethylpiperidin-1-yl)-3-(4,6-dimethoxy-2-hydroxy-phenyl)-3-(4-methylimidazol-4-yl)propan-1-one (A03Y01C01)

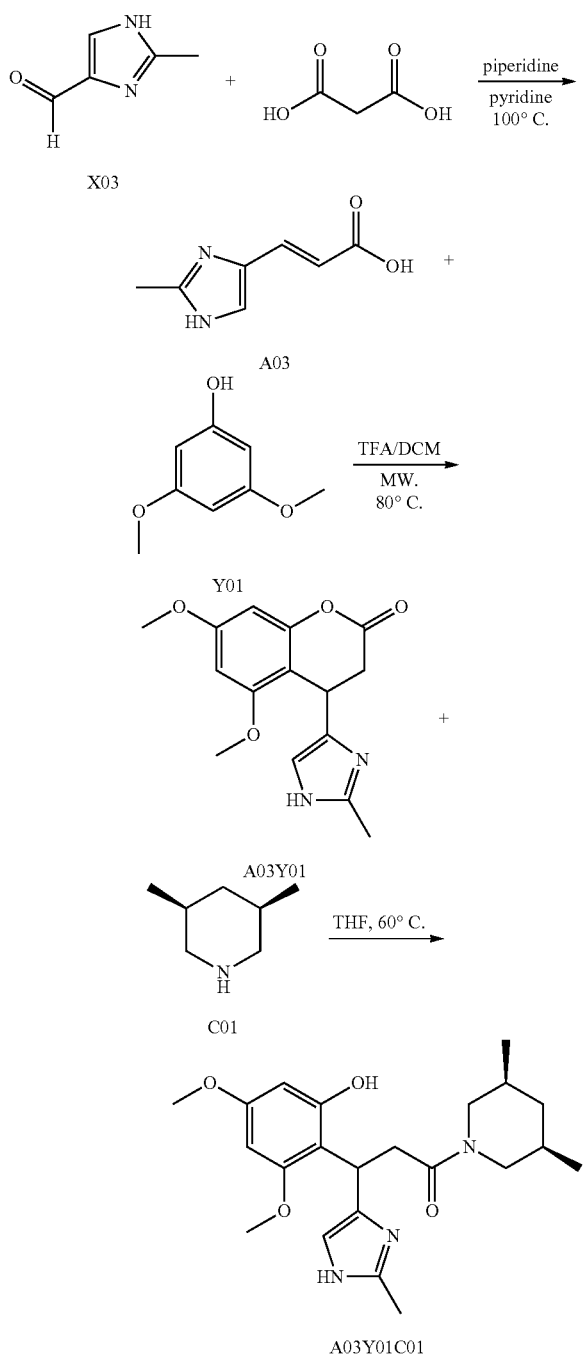

Step 1:

The starting imidazole derivative (X03, 500 mg, 1.0 eq.) and malonic acid (472.5 mg, 1.0 eq.) were dissolved in 3.5 mL of pyridine. 3 Drops of piperidine were added and the mixture was heated at 100° C. under nitrogen for 5 hours. The reaction was monitored by LCMS and TLC. The reaction solution was diluted with water, the pH was adjusted to 5 with 1M HCl, and then extracted twice with ethyl acetate (2×10 mL). The organic layers were combined, dried with anhydrous sodium sulfate, filtered and concentrated to obtain the crude product A03, which was purified by column chromatography (EtOAc:Petroleum=2:1) to get pure A03 (400 mg).

Step 2:

The intermediate A03 (300 mg, 1.0 eq.) and 3,5-dimethoxyphenol (Y01,304 mg, 1.0 eq.) were dissolved in 3 mL of TFA/DCE, and the mixture was stirred at 80° C. under microwave irradiation for 45 minutes. The reaction mixture was neutralized with aqueous $NaHCO_3$ and extracted with $CH_2Cl_2$. The organic layer was dried with anhydrous sodium sulfate, filtered and concentrated to obtain the crude product A03Y01 (300 mg), which was used as such for the next step.

Step 3:

The intermediate A03Y01 (300 mg, 1.0 eq.) and 3,5-dimethylpiperidine (C01, 130 mg, 1.1 eq.) were dissolved in 3 mL of THF, the reaction mixture was stirred at 60° C. for 12 hours, and the solvent was evaporated under reduced pressure to get the crude product A03Y01C01. The crude product was then dissolved in 2.5 mL MeOH, and purified by pre-HPLC to get pure 1-(3,5-dimethylpiperidin-1-yl)-3-(4,6-dimethoxy-2-hydroxy-phenyl)-3-(4-methylimidazol-4-yl)propan-1-one (A03Y01C01, 57.6 mg), QC: 95.87%.

$^1$H NMR (400 MHz, $CDCl_3$) δ 6.53 (s, 1H), 6.20 (dd, J=5.1, 2.4 Hz, 1H), 6.03 (d, J=2.3 Hz, 1H), 5.07-4.96 (m, 1H), 4.49 (d, J=12.8 Hz, 1H), 3.75 (d, J=3.1 Hz, 6H), 3.43 (dd, J=14.6, 10.0 Hz, 1H), 3.24 (dd, J=14.6, 9.1 Hz, 1H), 3.01-2.66 (m, 1H), 2.30 (d, J=6.4 Hz, 3H), 1.89 (dd, J=23.3, 11.6 Hz, 1H), 1.74 (d, J=10.3 Hz, 1H), 1.36 (ddd, J=47.7, 28.9, 15.8 Hz, 3H), 0.88-0.82 (m, 6H), 0.68 (d, J=24.5, 12.1 Hz, 1H).

MS (MeOH): [M+1]$^+$ 402.1, 384.1, 289.0, 212.2, 114.0.

Compound 204 Method A 1-(3,5-Dimethylpiperidin-1-yl)-3-(4,6-dimethoxy-2-hydroxy-phenyl)-3-(pyrazin-2-yl)propan-1-one (A04Y01C01)

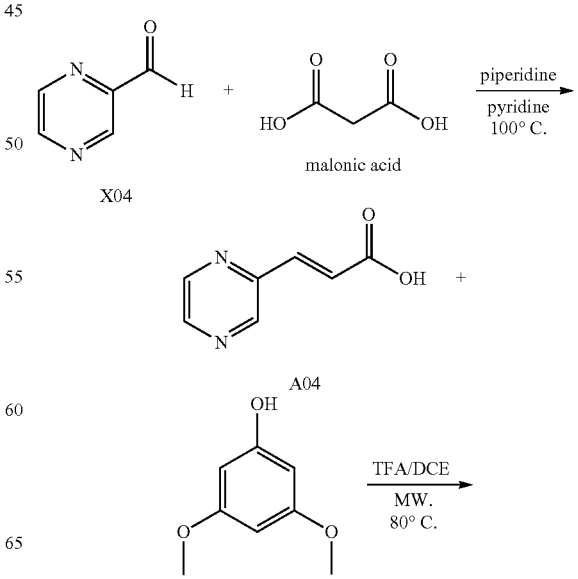

-continued

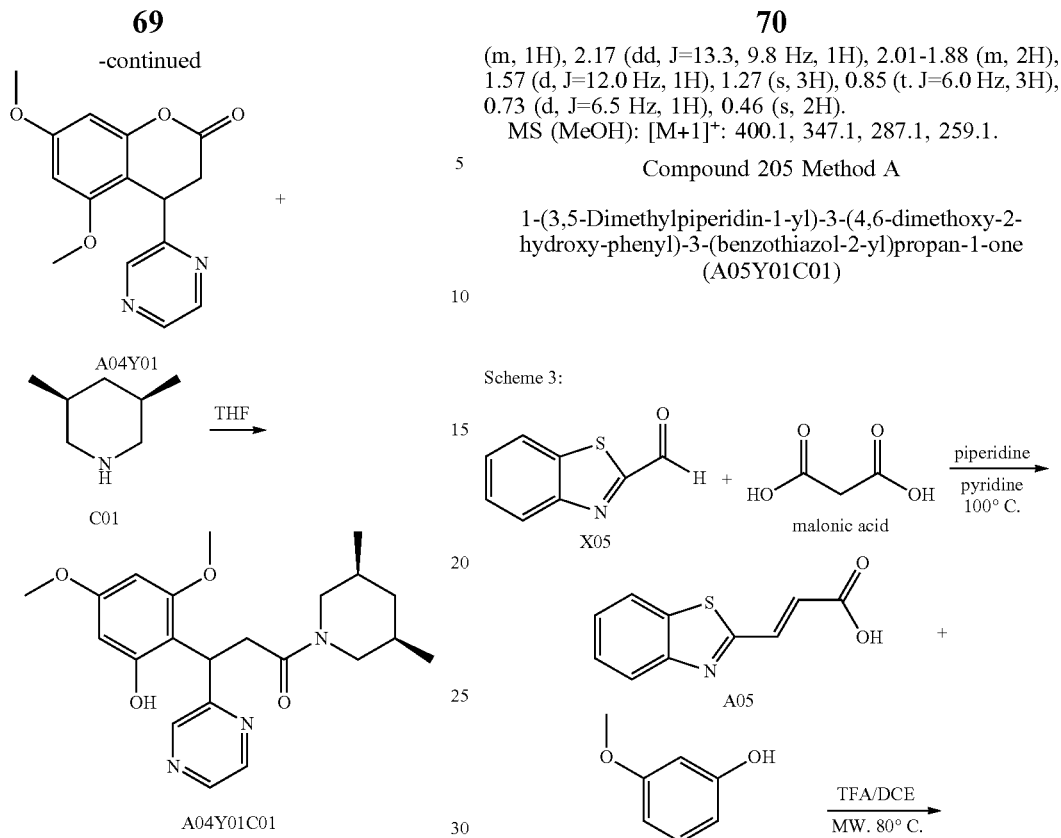

Step 1:
The starting pyrazine derivative (X04, 500 mg, 1.0 eq.) and malonic acid (481.3 mg, 1.0 eq.) were dissolved in 3.5 mL of pyridine, 3 drops of piperidine were added, and the mixture was heated at 100° C. under nitrogen for 5 hours. The reaction was monitored by LCMS and TLC. The reaction solution was diluted with water, the pH was adjusted to 5 with 1M HCl, and then extracted twice with ethyl acetate (2×10 mL). The organic layers were combined, dried with anhydrous sodium sulfate, filtered and concentrated to obtain the crude product A04, which was then purified by column chromatography (EtOAc:Petroleum=1:1) to get pure A04 (200 mg).

Step 2:
The intermediate A04 (200 mg, 1.0 eq.) and 3,5-dimethoxyphenol (205.37 mg, 1.0 eq.) were dissolved in 3 mL of TFA/DCE, and the mixture was stirred at 80° C. under microwave irradiation for 45 minutes. The reaction mixture was neutralized with aqueous NaHCO$_3$ and extracted with CH$_2$Cl$_2$. The organic layer was dried with anhydrous sodium sulfate, filtered and concentrated to obtain the crude product A04Y01 (100 mg)), which was used as such for the next step.

Step 3:
The intermediate A03Y01 (100 mg, 1.0 eq.) and 3,5-dimethylpiperidine (C01, 43.5 mg, 1.1 eq.) were dissolved in 3 mL of THF, the reaction mixture was stirred at 60° C. for 12 hours, and the solvent was evaporated under reduced pressure to get the crude product A04Y01C01, which was purified by pre-HPLC to yield pure 1-(3,5-dimethylpiperidin-1-yl)-3-(4,6-dimethoxy-2-hydroxy-phenyl)-3-(pyrazin-2-yl)propan-1-one (A04Y01C01, 6.4 mg), QC: 92.12%.

$^1$H NMR (400 MHz, CDCl$_3$) δ 8.43 (s, 1H), 8.30 (d, J=2.1 Hz, 1H), 8.21 (d, J=26.9 Hz, 1H), 7.28 (s, 1H), 6.02 (s, 2H), 4.56 (dd, J=15.2, 9.5 Hz, 2H), 3.64-3.57 (m, 6H), 3.22-3.08 (m, 1H), 2.17 (dd, J=13.3, 9.8 Hz, 1H), 2.01-1.88 (m, 2H), 1.57 (d, J=12.0 Hz, 1H), 1.27 (s, 3H), 0.85 (t. J=6.0 Hz, 3H), 0.73 (d, J=6.5 Hz, 1H), 0.46 (s, 2H).

MS (MeOH): [M+1]$^+$: 400.1, 347.1, 287.1, 259.1.

Compound 205 Method A 1-(3,5-Dimethylpiperidin-1-yl)-3-(4,6-dimethoxy-2-hydroxy-phenyl)-3-(benzothiazol-2-yl)propan-1-one (A05Y01C01)

Step 1:

The benzothiazole derivative (X05, 300 mg, 1.0 eq.) and malonic acid (191.3 mg, 1.0 eq.) were dissolved in 3.5 mL pyridine, 3 drops of piperidine were added and the mixture was heated at 100° C. under nitrogen for 5 hours, The reaction was monitored by LCMS and TLC. The reaction solution was diluted with water, the pH was adjusted to 5 with 1M HCl, and extracted twice with ethyl acetate (2×10 mL). The organic layers were combined, dried with anhydrous sodium sulfate, filtered and concentrated to obtain the crude product A05, which was purified by column chromatography (EtOAc:Petroleum=1:1) to get pure A05 (100 mg).

Step 2:

The intermediate A05 (100 mg, 1.0 eq.) and 3,5-dimethoxyphenol (Y01, 75.12 mg, 1.0 eq.) were dissolved in 3 mL of TFA/DCE, and the mixture was stirred at 80° C. under microwave irradiation for 45 minutes. The reaction mixture was then neutralized with aqueous NaHCO$_3$ and extracted with CH$_2$Cl$_2$. The organic layer was dried with anhydrous sodium sulfate, filtered and concentrated to obtain the crude product A05Y01 (65 mg)), which was used as such for the next step.

Step 3:

The intermediate A05Y01 (65 mg, 1.0 eq.) and 3,5-dimethylpiperidine (C01, 23.7 mg, 1.1 eq.) were dissolved in 3 mL THF, the reaction mixture was stirred at 60° C. for 12 hours, and the solvent was evaporated under reduced pressure to get crude product A05Y01C01, which was purified by pre-HPLC to give the pure titled compound, A05Y01C01 (6.5 mg), QC: 100%.

$^1$H NMR (400 MHz, CDCl$_3$) δ 7.91 (d, J=8.0 Hz, 1H), 7.80 (d, J=7.8 Hz, 1H), 7.35 (dt, J=29.0, 7.4 Hz, 2H), 5.94 (d, J=11.2 Hz, 2H), 4.68-4.54 (m, 2H), 3.95 (dd, J=14.2, 6.3 Hz, 1H), 3.49 (t, J=5.7 Hz, 6H), 2.19 (dd, J=13.2, 9.6 Hz, 1H), 2.04-1.89 (m, 2H), 1.77 (d, J=13.2 Hz, 1H), 1.59 (d, J=10.9 Hz, 1H), 1.36-1.24 (m, 3H), 0.87 (dd, J=15.7, 7.9 Hz, 3H), 0.75 (d, J=6.6 Hz, 1H), 0.49 (s, 2H).

MS (MeOH): [M+1]$^+$: 455.1, 342.0.

Compound 206 Method G 1-(3,5-Dimethylpiperidin-1-yl)-3-(4,6-dimethoxy-2-hydroxy-phenyl)-3-(2-methoxypyrid-5-yl)propan-1-one (B03X01C01)

A. Synthesis of the Starting Material—Z01

Scheme 4:

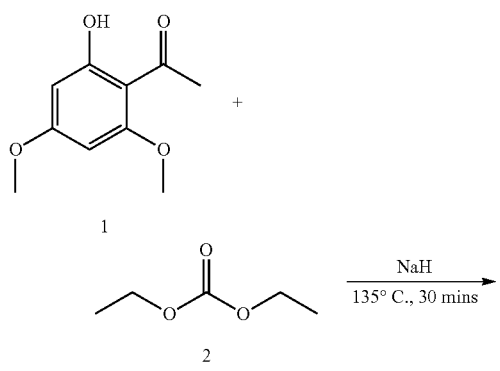

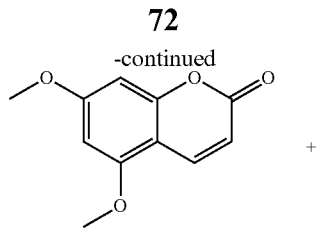

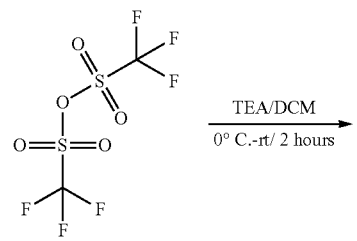

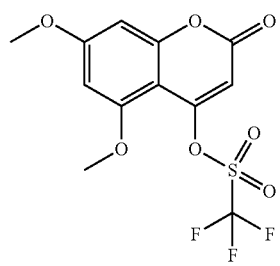

Step 1

2,4-Dimethoxy-6-hydroxybenzaldehyde (1, 5 g, 1.0 eq.) was dissolved in 5 mL of dimethyl carbonate, and NaH (1.2 g, 1.2 eq.) was added. The reaction mixture was refluxed at 135° C. for 30 mins, and then filtered to afford filter cake. The filter cake was dissolved in water, the pH was adjusted to 5-6 with aqueous 2M HCl to get a precipitate. The precipitated solid was collected by filteration, and was redissolved in EtOAc. The solution was dried over anhydrous Na$_2$SO$_4$, and filtered and the solvent was removed under reduced pressure to get the crude product 3, which was used as such for the next step.

Step 2

To a solution of the intermediate compound 3 (4.8 g, 1.0 eq.) and triethylamine (4.8 mL, 1.5 eq.) in 60 mL of dry dichloromethane at 0° C. under nitrogen was added trifluoromethanesulfonic anhydride (15 mL, 1.1 eq.) slowly. The reaction solution was allowed to warm to room temperature and stirred for 1 h. The reaction mixture was washed with 10 percent aqueous potassium carbonate (2×50 mL) and then aqueous 2M HCl (2×50 mL), and the organic layer was dried and the solvent was removed in vacuo to give the intermediate compound Z01 as a yellow solid. It was then purified by column chromatography (petroleum/EtOAc=30:1) to afford pure Z01 as white solid (3 g).

B. Preparation of Compound 206 (B03X01C01)

Scheme 5:

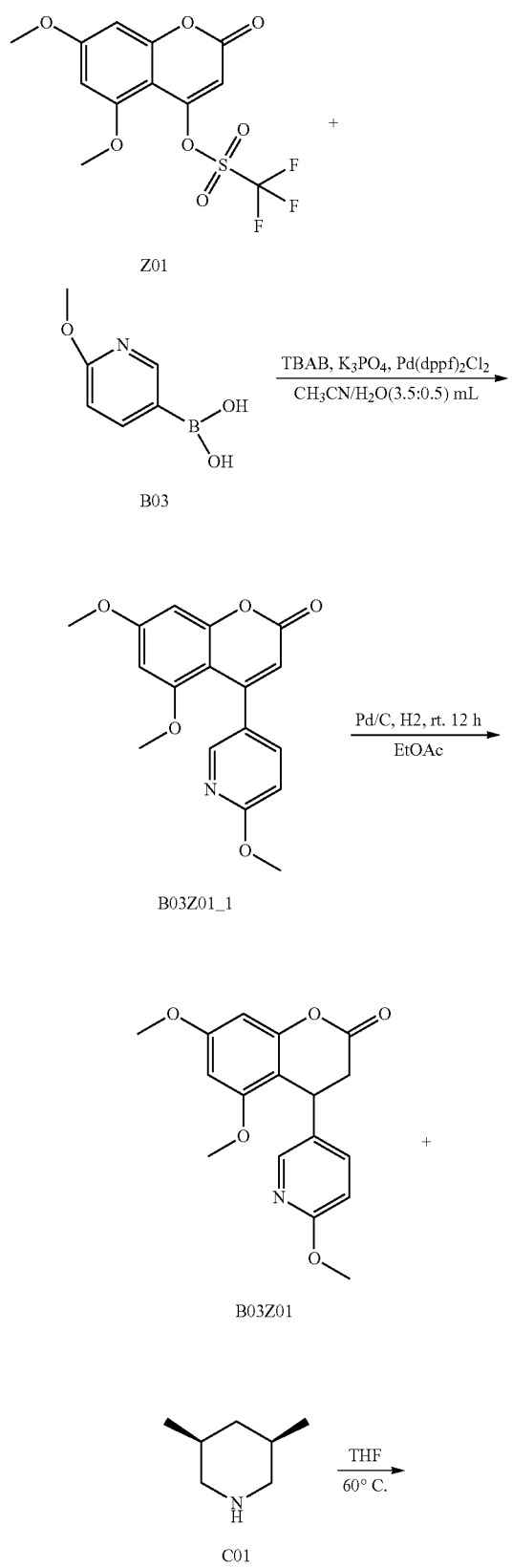

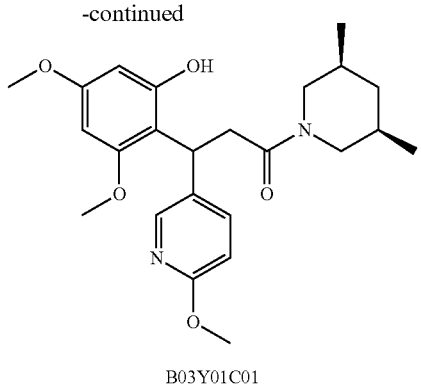

Step 1

A suspension of 4-trifluoromethylsulfonyloxy coumarin (100 mg, 1.0 eq.), boronic acid derivative B03 (43.17 mg, 1.1 eq.), potassium phosphate (179.6 mg, 3.0 eq.), tetrabutylamoniumbromid (9 mg, 0.1 eq.), and 1,1'-bis(diphenylphosphino)ferocene-palladium(II)dichloride dichloromethane complex (2.06 mg, 0.1 eq.) in acetonitrile/$H_2O$ (3.5 mL:0.5 mL), was refluxed under nitrogen until the substrate was completely consumed (12 h, monitored by LCMS or TLC). The reaction mixture was diluted with water and extracted with dichloromethane. The combined organic layers were dried over anhydrous $Na_2SO_4$, and the solvent was distilled under reduced pressure. The residue was purified by TLC (EtOAc/petroleum=3:2) or by prep-HPLC, to afford the intermediate B03Z01-1 (35 mg).

Step 2

The intermediate B03Z01-1 (35 mg, 1.0 eq.) was dissolved in 5 mL EtOAc, Pd/C (7 mg, 20%) was added and the mixture was stirred at rt. for 12 hours under $H_2$ balloon. The reaction was monitored by LCMS the stirring is continued until the double bond was reduced completely. The catalyst Pd/C was filtered off, and the solvent was removed under reduced pressure to afford the crude B03Z01 (20 mg) which was used as such for the next step.

Step 3

The intermediate B03Z01 (20 mg, 1.0 eq.) and 3,5-dimethylpiperidine (C01, 7.9 mg, 1.1 eq.) were dissolved in 2.5 mL of THF, the reaction mixture was stirred at 60° C. for 5 hours. The solvent was removed under reduced pressure to afford the crude product B03Z01C01. The crude product was then purified by prep-HPLC, to afford the target compound, 1-(3,5-dimethylpiperidin-1-yl)-3-(4,6-dimethoxy-2-hydroxy-phenyl)-3-(2-methoxypyrid-5-yl)propan-1-one (B03Z01C01, 11.8 mg), QC: 95.31%.

$^1$H NMR (400 MHz, $CDCl_3$) δ 8.53 (s, 1H), 8.02 (dd, J=21.7, 8.6 Hz, 1H), 6.96 (dd, J=8.9, 5.6 Hz, 1H), 6.32 (dd, J=16.1, 2.2 Hz, 1H), 6.21 (d, J=3.1 Hz, 1H), 5.99 (dd, J=8.7, 2.0 Hz, 1H), 5.02 (d, J=17.2 Hz, 1H), 3.97 (s, 3H), 3.79 (s, 3H), 3.75 (s, 3H), 3.45-3.34 (m, 2H), 3.03 (qd, J=15.9, 4.4 Hz, 2H), 2.52-2.38 (m, 2H), 2.03-1.95 (m, 2H), 1.27 (s, 2H), 1.03-0.93 (m, 6H).

MS (MeOH):[M+1]$^+$: 429.1, 362.1, 348.0, 316.3, 275.8, 186.1, 136.0.

Synthesis of Salts of Compounds of the Invention

The representative salts of the compounds of the invention can be prepared following the general synthetic methods described below.

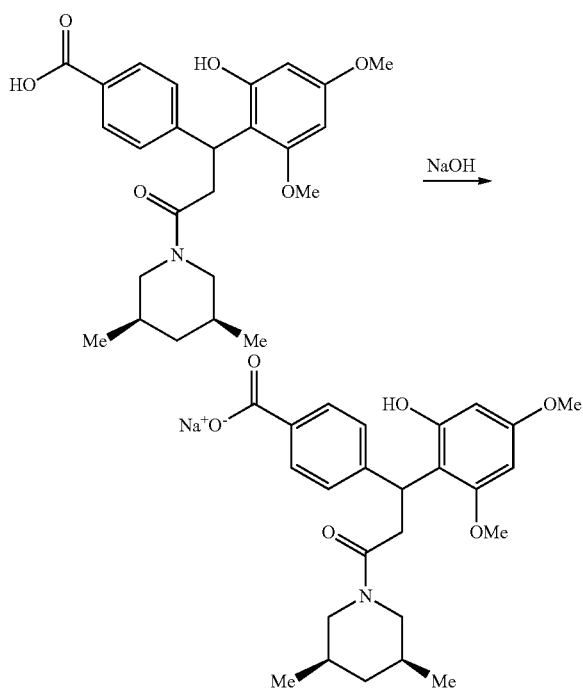

A round bottom flask is charged with the Compound 202 (0.001 mol) and THF (5 mL) and the mixture is stirred at room temperature. 0.5 mL of a sodium hydroxide solution (0.001 mol of NaOH) is added and the mixture was stirred for 30 minutes at room temperature. The solvents are removed at reduced pressure and the resultant semi-solid is taken up in diethyl ether where upon a white solid precipitated out upon standing. This mixture is allowed to sit at room temperature overnight. The solvent is decanted off and the solid dried under reduced pressure give the desired salt as a white solid.

Alternate Method for preparation of sodium salt: Compound 202 (44.1 mg, 0.10 mmol) and NaOH (0.10 mL of 1.0 N, 0.10 mmol) in 1.0 mL of water is stirred for 10 min. The clear solution is dried down by lyophilizer to give sodium salt of Compound 202 as a white powder.

The pharmaceutically acceptable salts of the compounds of formula I, wherein $R^3$ is $CO_2H$, $SO_3H$, or $CH_2CO_2H$ can be prepared following the procedures described above. For examples salts of Compound 99, 101, 201, 202, 317-332, 401-405, 407-412, 414, 416, 417, or 418 can be prepared using the procedures described above.

Assays

Development of a High-Throughput Screening Assay

Methods: The *Drosophila* S2 cell line was originally purchased from Invitrogen and was maintained in Schneider's medium supplemented with 10% heat-inactivated bovine fetal calf serum and antibiotics (Invitrogen). Gal4 DNA binding domain (G4DBD) corresponding to amino acids 1 through 147 of Gal4 protein was PCR amplified to make a fusion construct with mouse RORγt (amino acids 79 to the carboxyl terminal end) lacking its DNA binding domain. The resulting chimeric gene was subcloned into the copper inducible pMT/V5-His A vector (available from Invitrogen). In a similar manner, Gal4 fusion constructs were prepared with mouse RORα (amino acids 142 to end) or *Drosophila* DHR3 (amino acids 120 to end). Coding sequences for firefly luciferase (available from Promega) were PCR amplified and subcloned into pUAST vector containing Gal4 binding enhancer sequences. pUAST is a commonly used *Drosophila* vector used by ordinarily skilled practitioners and has been described by Brand et al. (Development 118(2):401-415, 1993), the entire contents of which is incorporated herein in its entirety.

*Renilla* luciferase construct under the polIII promoter was obtained from Dr. Dasgupta's laboratory (NYU medical center). In order to generate stable cell lines, cells were co-transfected with pMT-G4DBD-RORγt, pMT-G4DBD-RORα, pMT-G4DBD-DHR3, or pMT-G4DBDVP16 and pHygro plasmids (Invitrogen) and screened for resistant colonies in the presence of hygromycin (0.3 mg/mL). More than 150 independent RORγ stable clones with luciferase reporters (pMt-RORγ luc) were tested for their suitability for the high-throughput screening (HTS) based on the following criteria: high signal-to background ratio in 384- and 1,536- well plates, their high induction rate upon the addition of copper, and RORγ/γt specificity probed by the dsRORγ- or RORγ/γt antagonist-mediated suppression. Positive clones were further transfected with pUAST-firefly luciferase, polIII-*Renilla* luciferase, and pCoPuro (Iwaki, Figuera et al. 2003) ("Rapid selection of *Drosophila* S2 cells with the puromycin resistance gene." *Biotechniques* 35(3): 482-4, 486) and selected with puromycin (2.5 ug/ml). Seven clones were finally selected, and one of them (stable clone #25) was subsequently used for large-scale HTS. Using similar methods, stable clones with genomic integration of the luciferase reporters and other reporters were generated such as pMT-RORα_luc, pMT-DHR3_luc, or pMT-VP16_luc.

Results and Discussion: An activity-based assay system that permits high-throughput screening (HTS) for chemical modulators of RORγt transcriptional activity was developed. Since RORγt is located exclusively in cell nuclei, even when mutations are introduced in the putative ligand binding pocket, RORγt-dependent transcriptional activation, rather than the often used ligand-induced cytoplasm to nucleus translocation of hormone receptor, served as a better readout. A cell-based assay was used to eliminate cell-impermeable or toxic molecules and to perform screening in a biologically relevant setting. The system employed provided a high signal-to-noise ratio and was able to handle a large-scale screen, as well as be cost-effective. S2 cells were derived from late stage *Drosophila melanogaster* embryos with hemocyte-like morphology and gene expression profiles (Schneider, I. *J Embryol Exp Morphol*, 1972, 27, 353-65). They grew at room temperature as a semi-adherent monolayer with no requirement for $CO_2$, making it easy to apply large sets of small chemical molecules and to transfer cells without trypsin treatment.

Like other hormone receptors, RORγt contains both a DNA binding domain (DBD) and a ligand binding domain (LBD). The DBD was replaced with the heterologous yeast GAL4 DBD, because the endogenous DNA binding sites for RORγt are less well characterized.

The GAL4-RORγt fusion construct was placed under the control of a copper inducible promoter, and stable S2 cell lines with genomic integration of this construct were generated. The copper inducible promoter ensures a tight regulation of GAL4-RORγt expression and allows small molecules to get into the cells prior to its induction, thus increasing their effects on GAL4-RORγt. The reporter cells also carried the firefly luciferase reporter, whose expression is regulated by five copies of the GAL4 binding site enhancer (UAS) and a constitutive heat shock promoter, along with a control plasmid, pol III-driven *Renilla* luciferase. Pol III-*Renilla* luciferase was previously shown to serve as an excellent transfection and cell viability control in the S2 cell system. Use of Pol III-*Renilla* luciferase permitted normalization of RORγt-driven firefly luciferase activity and reduced cytotoxic effects and corrected for potential imprecise dispensation of cells in culture medium (Armknecht, S. et al. *Methods Enzymol,* 2005, 392, 55-73). When Cu++ was added, the ratio of firefly to *Renilla* luciferase activity (FR ratio) in these cells increased more than 100-fold compared to control cells lacking GAL4-RORγt (~34 fold increase compared to GAL4-RORγt cells treated with dsROR). RORγt induces robust transcriptional activation in *Drosophila* S2 cells in 384-well plates. For test with transient transfection, firefly reporter under GAL4 binding sites and Pol III-*Renilla* control plasmids were transiently transfected along with dsRNA (75 ng), targeting EYFP or RORγ, into both control or pMT-GAL4-RORγt stable S2 cell lines (10,000 cells/well). After three days, copper was added to induce GAL4-RORγt, and dual luciferase activity was measured following overnight incubation. The increase was also observed when the experiment was carried out in 384-well plates, demonstrating that it can be adopted as a high-throughput screen. Co-transfecting dsRNA that targets RORγt suppressed ROR-mediated firefly luciferase induction, demonstrating that this activity is ROR dependent.

In order to confirm that the RORγt function in S2 cells was physiologically relevant, it was first confirmed that *Drosophila* has a RORγt homologue. Mouse encodes three different ROR proteins, RORα, RORβ, and RORγ. RORγ and RORγt are two isoforms that differ in non-translated N-terminal mRNA sequences. Indeed, *Drosophila* has one ROR homologue, *Drosophila* hormone receptor 3 (DHR3) (King-Jones, K. & Thummel, C. S. *Nat Rev Genet,* 2005, 6, 311-23). Structure-based alignment using BLAST revealed 48% amino acid identity between DHR3 and RORγt.

Next it was confirmed that RORγt ligands are likely present in *Drosophila* S2 cells. Since many ligands for nuclear hormone receptors are found to be sterols or their derivatives, growth of cells in medium lacking FBS (fetal bovine serum) or medium supplemented with fatty-acid stripped serum (charcoal treated) was attempted. Only a small decrease of the FR ratio was detected in cells grown in this condition, and the results were not conclusive. Previous studies have shown that the introduction of a single amino acid change inside the ligand binding pocket of RORβ abrogates its function as a transcriptional activator, suggesting that RORβ is a ligand-dependent hormone receptor. The crystal structure of the protein strongly suggested that replacement of alanine 269 with amino acids carrying bulkier side chains, such as valine and phenylalanine, would prevent binding of endogenous ligands without affecting the correct folding of the ligand binding domain (Stehlin, C. et al. *Embo J,* 2001, 20, 5822-31). When the corresponding alanine residue in the putative ligand binding pocket of RORγt was replaced with phenylalanine, the mutant protein was no longer sufficient to induce Th17 cell differentiation when transduced into naive mouse CD4+ T cells, consistent with the presence of cognate RORγt ligand(s) in these cells. The Ala to Phe mutation in RORγt also completely abrogated transcriptional activation of firefly luciferase expression without affecting the transcription of control *Renilla* luciferase, suggesting that RORγt ligand is present in the *Drosophila* assay system. Indeed, introduction of alanine to phenylalanine (F) mutation in a putative ligand binding pocket abolishes activity of RORγt in this system. As confirmed by immunoblot, the alanine to phenylalanine mutation did not, however, affect protein stability.

DHR3 is transcriptionally regulated by 20-hydroxyecdysone (20E) and is essential for fly larval development (King-Jones, supra). It has been shown that E75, another 20E-dependent fly nuclear hormone receptor, negatively regulates the function of DHR3 (White, K. P., Hurban, P., Watanabe, T. & Hogness, D. S. *Science,* 1997, 276, 114-17; Reinking, J. et al. *Cell,* 2005, 122, 195-207. Indeed, co-expression of E75a or E75b (two *Drosophila* E75 isoforms) decreased the level of DHR3-mediated transcriptional activation in a dosage-dependent manner. E75 is a hormone receptor having antagonizing activities of DHR3 and RORγt. Transfection of increased amount of E75a or E75b resulted in concomitant reduction of FR ratio. Each well received the same amount of DNA in transfection mix. These fly genes also function as dosage-dependent negative regulators for mouse RORγt activity in S2 cells, without affecting the functions of an irrelevant transcriptional activator VP16, strongly suggesting that the ROR/DHR3 core regulatory mechanism is conserved between mouse and fly systems. Collectively, these data confirm the accuracy and relevance of the above approach utilizing the heterologous S2 cell system in order to identify chemical agonists or antagonists of the mouse hormone receptor RORγt.

Measurement of Luciferase Activity.

Methods: Promega Dual-Glo system is widely used for HTS as the luciferase substrates. Cell culture medium was reduced to the final volume of 10 μl or less and 10 μl of Dual-glo and 10 μl of Stop-glo luciferase substrates were added in a sequential manner (Promega). Firefly and *Renilla* luciferase activity was determined by measuring luminescence signals using an automated 384-well plate reader equipped with multiple stack units (such as the Analyst GT or Envision plate readers).

Results and Discussion: The Dual-Glo luciferase assay system from Promega facilitated measuring luciferase activity in HTS. First, it did not require a washing step, and the luciferase activities of both the firefly and the *Renilla* could be measured in the same well one after the other. Second, the signals that it produced remained stable for more than two hours, making it possible to measure activity from many different plates for a given experiment. Since the reagents are expensive, the volume of medium was reduced to one third prior to adding luciferase substrates, so that fewer substrates were used. However, when minimizing cost is less of a priority, the luciferase substrates used in the primary assay may be directly added to cells without going through this additional step.

HTS for Identification of RORγ/γt Antagonists Using RORγ/γt-luc Stable Cell Lines Methods: 600 G4DBD-RORγ/γt-luc reporter (#25) or G4DBD-VP16-luc reporter cells were distributed into each well of 1,536-well white bottom plates in 4 μl S2 cell culture volume containing hygromicin (300 μg/ml) and puromycin (2 μg/ml). Small compounds in seven different concentrations range from 46 μM to 1.7 nM were pin-transferred (23 nl) by a robot (Inglese et al., 2006, Proc. Natl. Acad. Sci. 103:11473-8). After one-hour incubation, 1 of culture medium solution containing copper sulfate (to final 0.7 mM) and 10 μM RORγ/γt antagonists were added to each well. After 20-hour incubation at ambient temperature, 1.5 μl firefly luciferase detection mix was added and the luciferase activities were measured in 10 min. ViewLux luminometers were used for measuring luciferase signal.

Results and Discussion: Even though G4BD-RORγt stable cells with transient transfection of two luciferase constructs were successfully used for small-scale screening and led the present inventors to identify specific RORγ/γt antagonists in Harvard LCCB, it became problematic to apply the same method to larger scale screens with chemical libraries covering more than 250,000 compounds. First, transient transfection method often produced well-to-well variation due to incomplete mixing and unequal distribution of transfection mix. There is also day-to-day variation when preparing the master transfection mix. Second, in order to save reagent and to handle large quantities of chemicals, it was necessary to do the screen with reduced numbers of cells in a smaller culture volume. Moreover, performing the screen with 1,536-well plates is more efficient than performing the screen with 384-well plates. Thus, new RORγ/γt-luc reporter stable cells were developed to eliminate the necessity of repeated transfection and to achieve increased well-to-well consistency. When tested in a 384-well plate, even small numbers of cells (400 cells/well) gave high firefly luciferase signal (thus high RORγ/γt activity), which is suppressed (22-fold reduction when 400 cells are used) by addition of a RORγ/γt antagonist. The new stable cell line systems also turned out to be suitable for FITS in 1,536-well plates, because z' value is 0.75 when 600 cells are used per well with 10 µl total cell culture volume.

Using RORγ/γt-luc reporter lines, the pilot screen with the LOPAC (Sigma) library was performed through a NIH roadmap program to identify RORγ/γt antagonist compounds. LOPAC contains 1,280 pharmacologically active compounds. Among these, approximately 40 compounds were found as initial hits (~0.3%). These hits were tested against validation screens to identify RORγ/γt specific compounds. To facilitate a large-scale validation, VP16-luc reporter cell lines with genomic integrations of G4BD-VP16, UASt-ffluc, and polIII-Rluc were developed as discussed earlier. These cells also exhibited robust and consistent VP16 activity in 1,536-well plates (data not shown), and thus can be used as a good control reporter to weed-out compounds inhibiting general transcription, the function of GAL4 DNA binding domain, and a nuclear import of GAL4 chimeric proteins. Indeed, many compounds were identified as initial hits to reduce RORγ/γt activity from the pilot LOPAC screen, but later were found to be non-specific inhibitors, because they reduced both RORγ/γt and VP16 activities. Intriguingly, previously identified RORγ/γt specific antagonists identified by small scale HTS, also selectively inhibited RORγ/γt activity without affecting VP16, confirming their specificity on RORγ/γt. A large-scale screen covering more than 250,000 compounds was carried out against RORγ/γt-luc and VP16-luc reporter systems in parallel to identify RORγ/γt specific antagonists in a systematic manner.

Secondary assays directed toward evaluating the ability of such compounds to suppress mouse or human Th17 cell differentiation are also encompassed herein. Exemplary secondary assays that serve to confirm bona fide RORγ inhibitors include without limitation:

Secondary Screening Lists
1) S2 cell reporter system: Identified hits from HTS are further screened and their specificity confirmed by testing against RORγ-luc, VP16-luc, RORα-luc, and DHR3-luc reporter S2 cell lines. Compounds either having no activity on VP16, RORα, and DHR3 or having ten times higher $IC_{50}$ values on such reporters are selected for further tests.
2) Cytokine induced mouse Th17 cells differentiation. Effects on mouse endogenous RORγt in a relevant physiological setting were determined by testing compounds in the Th17 cell differentiation assay. Compounds having RORγt inhibitory activity are predicted to suppress Th17 cell differentiation. Th1 or regulatory T cell differentiation was used as a counter-screen method to select specific compounds that only affect Th17 cell differentiation without having pleiotrophic effects on general T cell proliferation or cytokine production.
3) ROR dependent Th17 cell differentiation. Compounds were further tested, by examining their effects on T cells expressing RORα or RORγ. Compounds that directly inhibit RORγ are expected to inhibit RORγ- but not RORα-dependent Th17 cell differentiation. Compounds affecting IL17a production or ROR regulatory pathways, however, are expected to inhibit both.
4) Human Th17 cell differentiation. Compound effects on human RORγt will be tested by treating human cord blood CD4 T cells with select compounds to determine if such compounds alter differentiation into Th17 lineages.

With aspects of the claimed invention now being generally described, these will be more readily understood by reference to the following examples, which are included merely for purposes of illustration of certain features and embodiments of the presently claimed invention and are not intended to be limiting.

EXAMPLES

As detailed above, in order to identify small molecules to antagonize RORγ/γt transcriptional activity, the present inventors developed insect cell line based reporter systems, expressing murine RORγ/γt or closely related transcriptional activators. Since their cognate DNA binding sites were not well characterized, the DNA binding domains (DBD) of RORγ/γt, RORα (mouse homolog for POPγ), and DHR3 (*Drosophila* orthologue for ROR family proteins) were replaced with the heterologous yeast GAL4 DBD. The transcriptionally active domain of general transcriptional activator VP16 was also fused with GAL4 DBD. The GAL4 fusion constructs were placed under the control of a copper inducible promoter, and stable S2 cell lines with genomic integration of these four reporter constructs were generated. The copper inducible promoter ensures tight regulation of GAL4-fusion protein expression and it allows small molecules to get into the cells prior to protein induction, thus increasing their effects on GAL4 reporters. The stable reporter cell lines also encode the firefly luciferase reporter, whose expression is regulated by five copies of the GAL4 binding site enhancer (UAS), along with the pol III-driven *Renilla* luciferase reporter. Pol III-*Renilla* luciferase was included to serve as cell viability control in the S2 cell system (Armknecht, S. et al. *Methods Enzymol* 392, 55-73 (2005).

From screening a chemical compounds library consisting of 4,812 compounds, including known Bioactives and Prestwick collections, a number of compounds were identified as small molecule inhibitors for the RORγ/γt transcriptional activity.

$IC_{50}$ Determinations

A cell-based reporter assay was used to detect RORγt-mediated activity. This assay, called RORγt employed *Drosophila* Schneider cells that were stably transfected with two vectors: a gene expressing a fusion of the Gal4 DNA binding domain and RORγt transactivation domain under the control of the metallothionine promoter and a *Photinus* luciferase reporter regulated by the Gal4 binding site enhancer, UAS. Copper addition to the medium induced expression of the Gal4-RORγt fusion, which subsequently induced expression of the UAS-luciferase reporter. Small molecule inhibitors of RORγt activity were detected by a decrease in luciferase reporter activity. Cells (600/well) were dispensed into white solid 1536-well plates (Greiner) using a solenoid-based dispenser. Following transfer of 23 mL compound or DMSO vehicle by a pin tool, the plates were incubated 1 hr at ambient temperature, and 1 uL/well copper sulfate (700 uM final concentration) was added. The plates were centrifuged 15 s at 1000 RPM and incubated 20 hr at ambient temperature. After addition of 1.5 uL *Photinus* luciferase detection reagent, the plates were incubated 10 min at ambient temperature and then read by a ViewLux (Perkin Elmer) to detect luminescence. The concentration-response data were fit using a reported algorithm (Wang, Y. et al. Current Chemical Genomics, 2010, 57-66). Efficacy is expressed as % of the maximal response of control inhibitor (Digoxin), set at 100%. $IC_{50}$ is the concentration at which compound exhibits half-maximal efficacy.

A number of representative amido compounds of this invention were or can be tested for their inhibitory activity. The amido compounds of the invention along with their $IC_{50}$ and Efficacy values, as determined using conventional methods to those skilled in the art, are listed below in Table 1. For the purpose of Table 1 and Table 1A, the $IC_{50}$ values are expressed as follows:

++++ compound exhibited $IC_{50}$<1 μM
+++ compound exhibited $IC_{50}$ 1-10 μM
++ compound exhibited $IC_{50}$ 11-50 μM
+ compound exhibited $IC_{50}$>50 μM

TABLE 1

$IC_{50}$ Values for Exemplary Compounds

| Sample ID | Compd # | Structure | MW (Calcd) | MW (obsvd) | $IC_{50}$ (μM) | Efficacy (%) |
|---|---|---|---|---|---|---|
| NCGC00238411 | 70 | 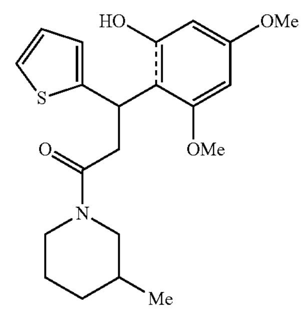 | 389.52 | 390.30 | +++ | −95.0 |
| NCGC00242603 | 79 | 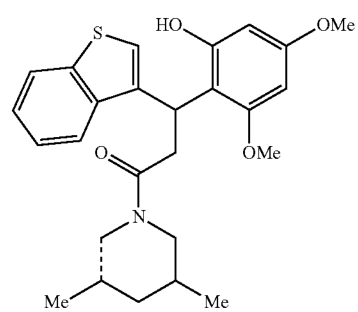 | 453.61 | 454.20 | +++ | 90.8 |
| NCGC00242608 | 83 | 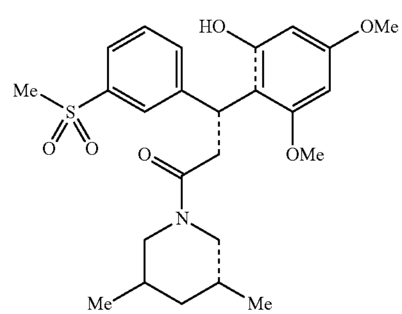 | 475.61 | 476.20 | +++ | −93.79 |

TABLE 1-continued

IC₅₀ Values for Exemplary Compounds

| Sample ID | Compd # | Structure | MW (Calcd) | MW (obsvd) | IC₅₀ (μM) | Efficacy (%) |
|---|---|---|---|---|---|---|
| NCGC00242609 | 84 | 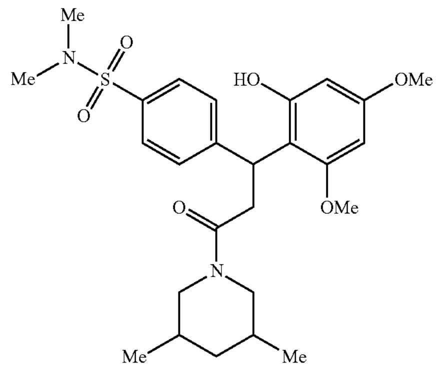 [SMILES: COc1cc(O)c(C(CC(=O)N2CC(C)CC(C)C2)c2ccc(S(=O)(=O)N(C)C)cc2)c(OC)c1] | 504.65 | 505.20 | ++ | −102.71 |
| NCGC00242620 | 95 | 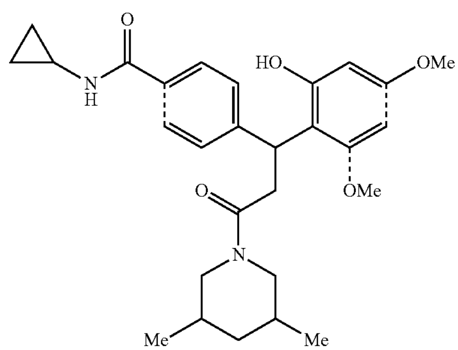 | 480.61 | 481.20 | +++ | −93.06 |
| NCGC00242624 | 99 | 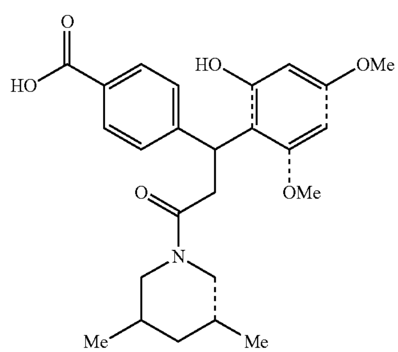 | 441.53 | 442.20 | +++ | −92.59 |
| NCGC00242625 | 100 | 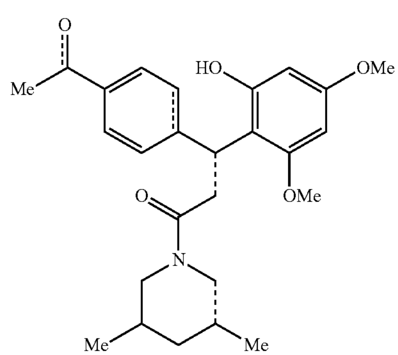 | 439.56 | 440.20 | ++++ | −93.60 |

TABLE 1-continued

IC$_{50}$ Values for Exemplary Compounds

| Sample ID | Compd # | Structure | MW (Calcd) | MW (obsvd) | IC$_{50}$ (μM) | Efficacy (%) |
|---|---|---|---|---|---|---|
| NCGC00242626 | 101 | 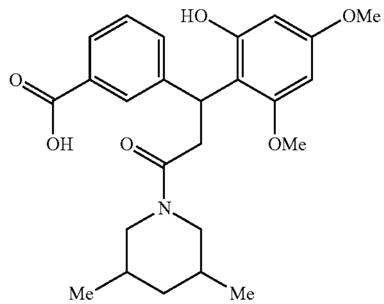 [SMILES: COc1cc(O)c(C(CC(=O)N2CC(C)CC(C)C2)c2cccc(C(=O)O)c2)c(OC)c1] | 441.53 | 442.20 | +++ | −88.72 |
| NCGC00242632 | 106 | 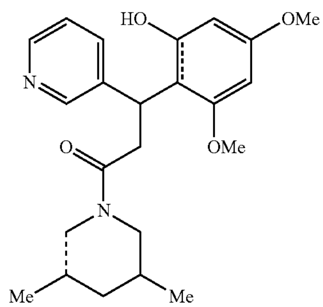 | 398.51 | 399.20 | +++ | −96.9 |
| NCGC00242633 | 107 | 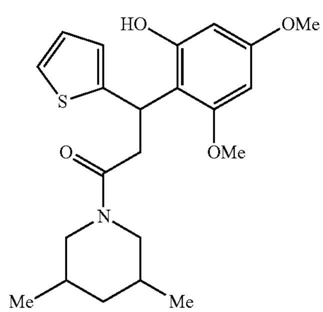 [SMILES: COc1cc(O)c(C(CC(=O)N2CC(C)CC(C)C2)c2cccs2)c(OC)c1] | 403.54 | 404.20 | +++ | −94.9 |
| NCGC00242634 | 108 | 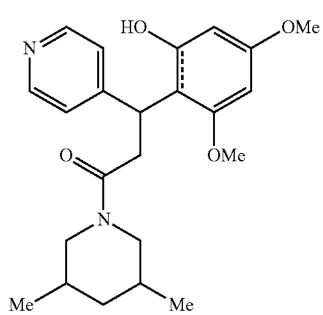 | 398.51 | 399.20 | ++ | −118.67 |

TABLE 1-continued

IC$_{50}$ Values for Exemplary Compounds

| Sample ID | Compd # | Structure | MW (Calcd) | MW (obsvd) | IC$_{50}$ (μM) | Efficacy (%) |
|---|---|---|---|---|---|---|
| NCGC00242606 | 111 | 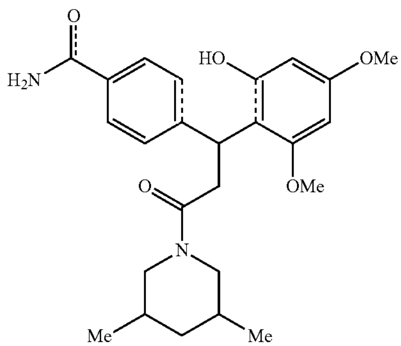 | 440.54 | 441.20 | +++ | −96.74 |
| NCGC00242631 | 139 | 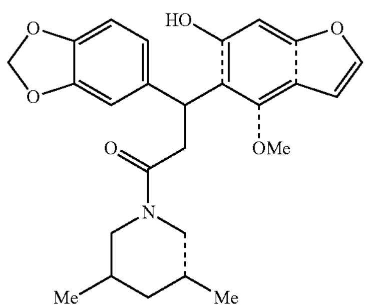 | 451.52 | 452.20 | +++ | −94.5 |
| NCGC00242638 | 142 | 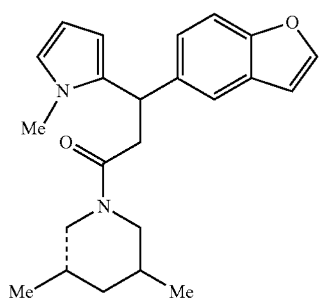 | 368.48 | 369.10 | + | −9.3 |
| NCGC00242642 | 146 | 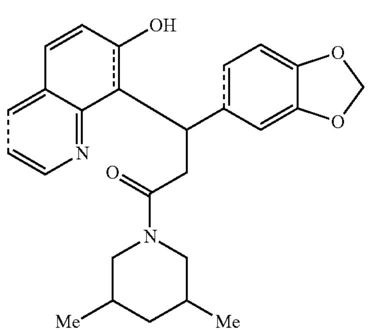 | 432.52 | 433.10 | +++ | −94.07 |

TABLE 1-continued

IC$_{50}$ Values for Exemplary Compounds

| Sample ID | Compd # | Structure | MW (Calcd) | MW (obsvd) | IC$_{50}$ (μM) | Efficacy (%) |
|---|---|---|---|---|---|---|
| NCGC00249676 | 201 | [structure: 4-(HO$_2$C)phenyl and 2,4,6-trimethoxyphenyl on CH, with CH$_2$C(O)-N(3,5-dimethylpiperidine)] | 455.5 | 456.1 | ++++ | −87 |

* The stereochemistry is not confirmed.

The following additional representative amido compounds of this invention, which are prepared in according the methods described herein or can be prepared following the methods described in the literature or following the methods known to those skilled in the art, are given in Table 1A, Table 1B, and Table 1C.

TABLE 1A

Additional Compounds of the Invention

| Sample ID | Compd # | Structure | MW (Calcd) | MW (obsvd) | IC$_{50}$ (μM) |
|---|---|---|---|---|---|
| NCGC00249675 | 202 | [structure: 4-carboxyphenyl and 2-hydroxy-4,6-dimethoxyphenyl on CH, with CH$_2$C(O)-N(3,5-dimethylpiperidine)] | 441.53 | 442.20 | ++++ |
| A03Y01C01 | 203 | [structure: 2-methylimidazol-5-yl and 2-hydroxy-4,6-dimethoxyphenyl on CH, with CH$_2$C(O)-N(3,5-dimethylpiperidine)] | 403.53 | 402.1 | +++ |

TABLE 1A-continued

Additional Compounds of the Invention

| Sample ID | Compd # | Structure | MW (Calcd) | MW (obsvd) | IC$_{50}$ (μM) |
|---|---|---|---|---|---|
| A04Y01C01 | 204 | 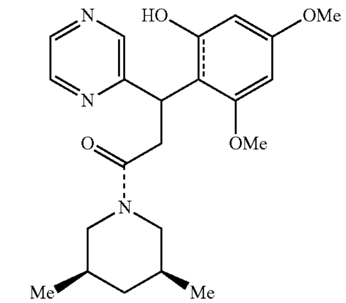 | 401.51 | 400.1 | +++ |
| A05Y01C01 | 205 | 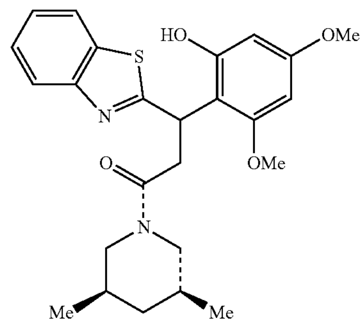 | 456.61 | 455.1 | ++++ |
| B03Z01C01 | 206 | 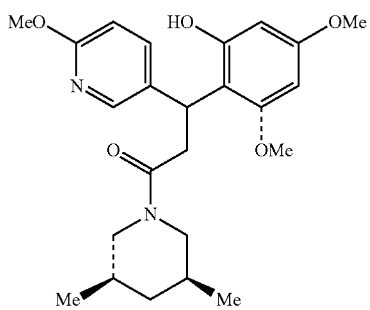 | 431.56 | 429.1 | ++++ |

TABLE 1B

Further Additional Compounds of the Invention

| Compd # | Structure | MW (Calcd) |
|---|---|---|
| 301 | 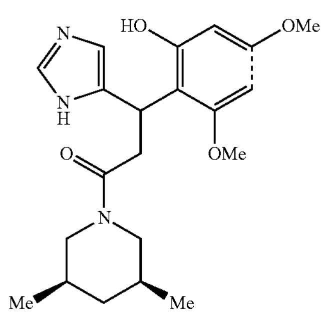 | 387.48 |

TABLE 1B-continued

Further Additional Compounds of the Invention

| Compd # | Structure | MW (Calcd) |
|---|---|---|
| 302 | 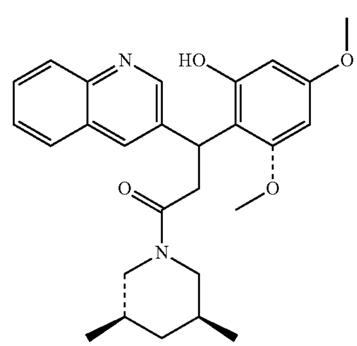 | 448.57 |

TABLE 1B-continued

Further Additional Compounds of the Invention

| Compd # | Structure | MW (Calcd) |
|---|---|---|
| 303 | 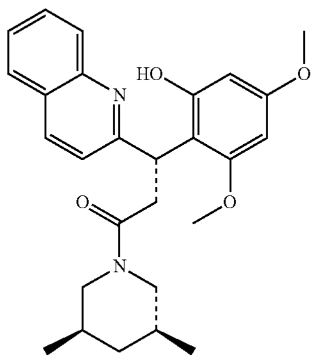 | 448.57 |
| 304 | 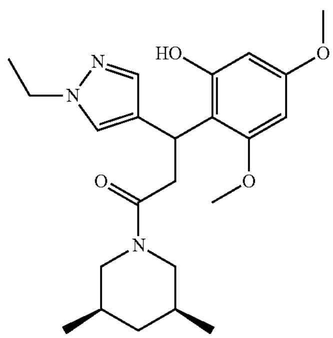 [SMILES: CCn1cc(C(CC(=O)N2C[C@H](C)C[C@H](C)C2)c2c(O)cc(OC)cc2OC)cn1] | 415.54 |
| 305 | 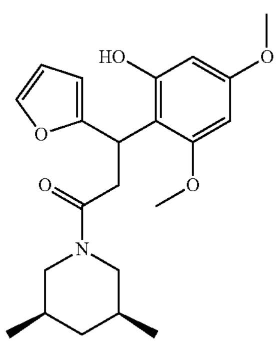 | 387.48 |
| 306 | 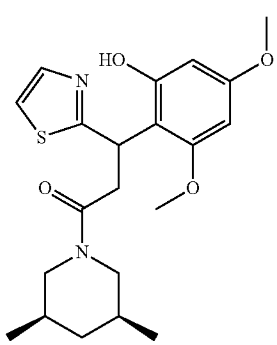 | 404.53 |
| 307 | | 400.52 |
| 308 | | 383.49 |
| 309 | | 396.54 |
| 310 | | 409.58 |

TABLE 1B-continued

Further Additional Compounds of the Invention

| Compd # | Structure | MW (Calcd) |
|---|---|---|
| 311 | 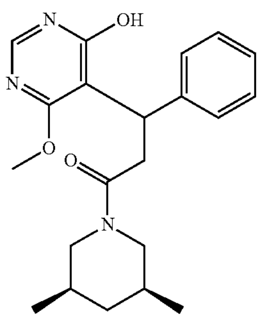 [SMILES: COc1ncnc(O)c1C(CC(=O)N1C[C@H](C)C[C@H](C)C1)c1ccccc1] | 369.47 |
| 312 | 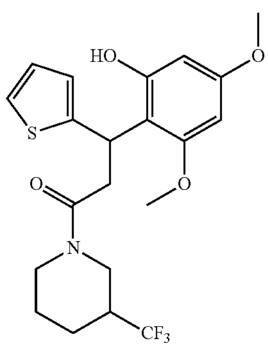 [SMILES: COc1cc(O)c(C(CC(=O)N2CCCC(C(F)(F)F)C2)c2cccs2)c(OC)c1] | 443.49 |
| 313 | 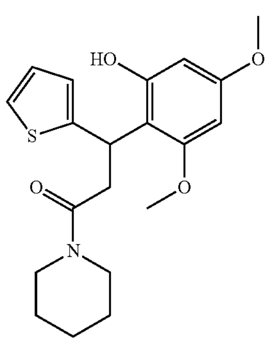 [SMILES: COc1cc(O)c(C(CC(=O)N2CCCCC2)c2cccs2)c(OC)c1] | 375.49 |
| 314 | 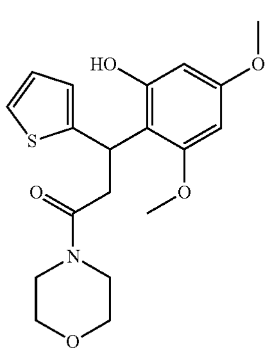 [SMILES: COc1cc(O)c(C(CC(=O)N2CCOCC2)c2cccs2)c(OC)c1] | 377.46 |
| 315 | | 391.49 |
| 316 | | 405.52 |
| 317 | | 412.49 |
| 318 | | 426.52 |

TABLE 1B-continued
Further Additional Compounds of the Invention
| Compd # | Structure | MW (Calcd) |
|---|---|---|
| 319 | 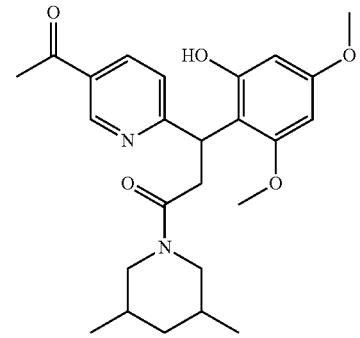 [SMILES: COc1cc(O)c(C(CC(=O)N2CC(C)CC(C)C2)c2ccc(C(C)=O)cn2)c(OC)c1] | 440.54 |
| 320 | 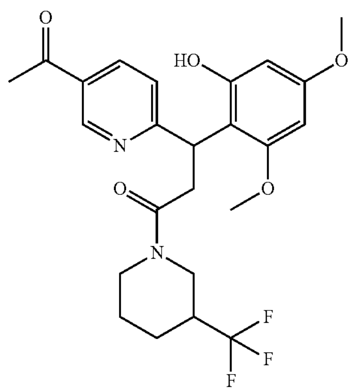 [SMILES: COc1cc(O)c(C(CC(=O)N2CCCC(C(F)(F)F)C2)c2ccc(C(C)=O)cn2)c(OC)c1] | 480.49 |
| 321 | 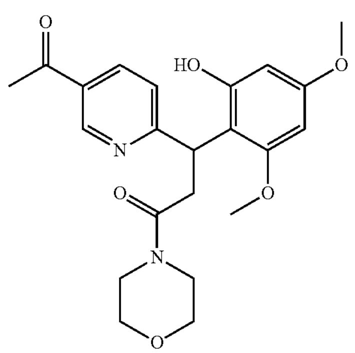 [SMILES: COc1cc(O)c(C(CC(=O)N2CCOCC2)c2ccc(C(C)=O)cn2)c(OC)c1] | 414.46 |
| 322 | 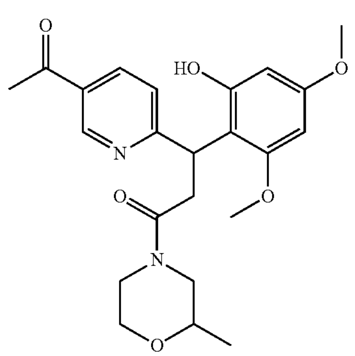 [SMILES: COc1cc(O)c(C(CC(=O)N2CCOC(C)C2)c2ccc(C(C)=O)cn2)c(OC)c1] | 428.52 |
| 323 | 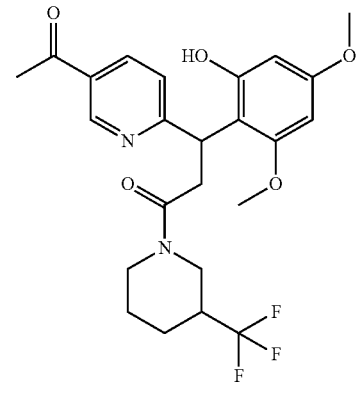 | 442.54 |
| 324 | | 482.49 |
| 325 | | 412.49 |
| 326 | | 426.52 |

TABLE 1B-continued

Further Additional Compounds of the Invention

| Compd # | Structure | MW (Calcd) |
|---|---|---|
| 327 | 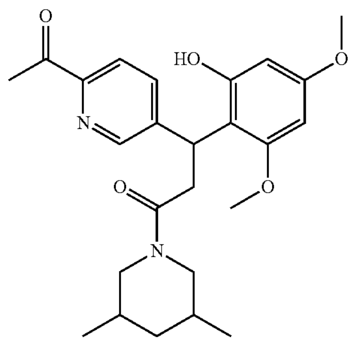 [SMILES: COc1cc(O)c(C(CC(=O)N2CC(C)CC(C)C2)c2ccc(C(C)=O)nc2)c(OC)c1] | 440.54 |
| 328 | 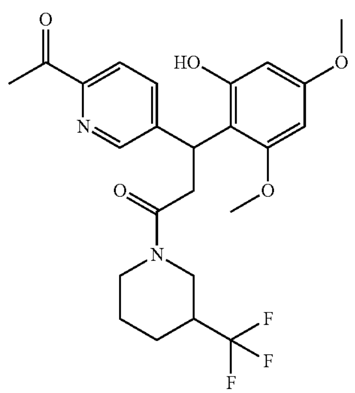 [SMILES: COc1cc(O)c(C(CC(=O)N2CCCC(C(F)(F)F)C2)c2ccc(C(C)=O)nc2)c(OC)c1] | 480.49 |
| 329 | 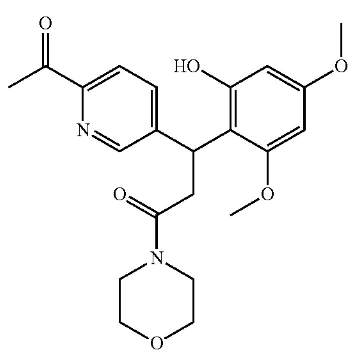 [SMILES: COc1cc(O)c(C(CC(=O)N2CCOCC2)c2ccc(C(C)=O)nc2)c(OC)c1] | 414.46 |
| 330 | 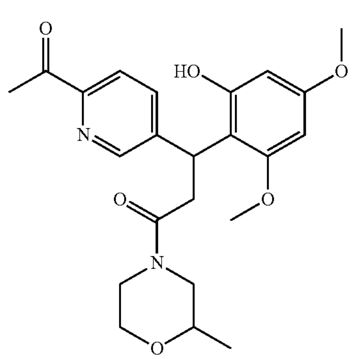 [SMILES: COc1cc(O)c(C(CC(=O)N2CCOC(C)C2)c2ccc(C(C)=O)nc2)c(OC)c1] | 428.52 |
| 331 | | 442.54 |
| 332 | | 482.49 |
| 333 | | 453.54 |
| 334 | | 453.54 |

TABLE 1B-continued

Further Additional Compounds of the Invention

| Compd # | Structure | MW (Calcd) |
|---|---|---|
| 335 | 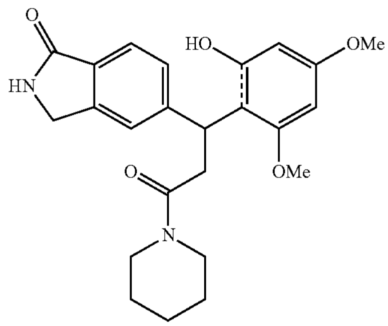 | 424.50 |
| 336 | 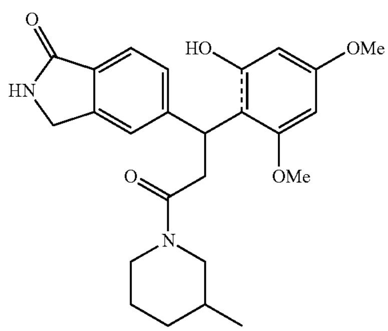 | 438.53 |
| 337 | 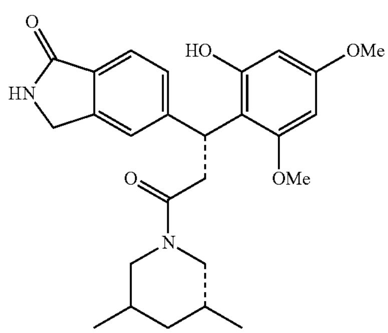 | 452.56 |
| 338 | 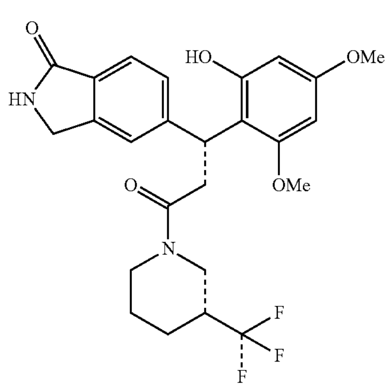 | 492.50 |
| 339 | | 426.50 |
| 340 | | 440.53 |
| 341 | | 454.56 |
| 342 | | 494.50 |

TABLE 1B-continued

Further Additional Compounds of the Invention

| Compd # | Structure | MW (Calcd) |
|---|---|---|
| 343 | 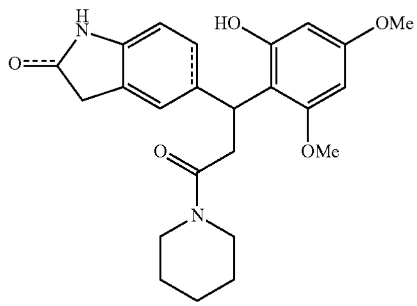 | 424.50 |
| 344 | 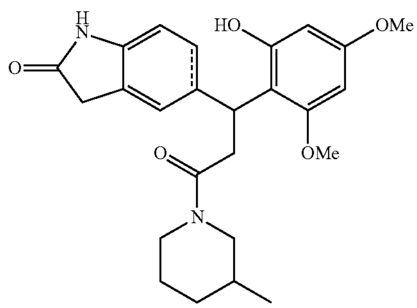 | 438.53 |
| 345 | 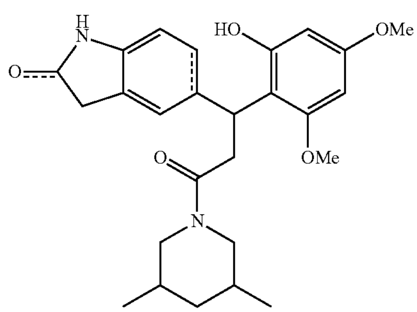 | 452.56 |
| 346 | 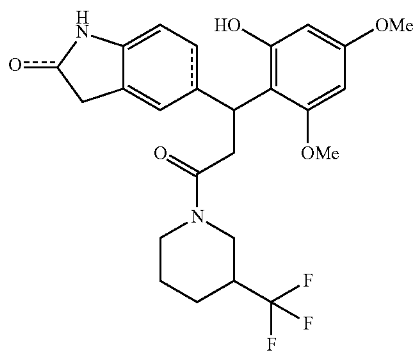 | 492.50 |
| 347 | | 426.50 |
| 348 | | 440.53 |
| 349 | | 454.56 |
| 350 | | 494.50 |

TABLE 1C

More Additional Compounds of the Invention

| Compd # | Structure | MW (Calcd) |
|---|---|---|
| 401 | 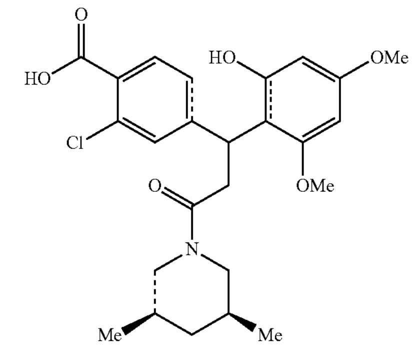 | 475.97 |
| 402 | 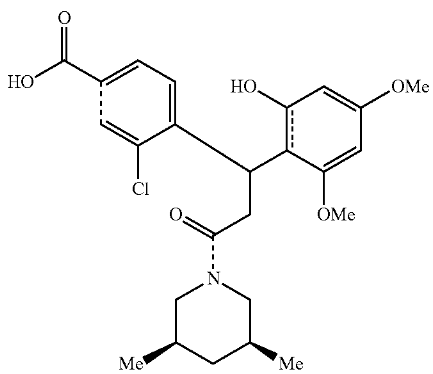 | 475.97 |
| 403 | 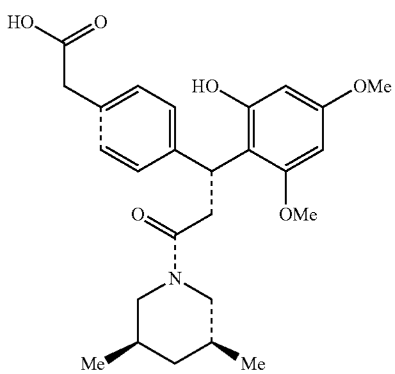 | 455.56 |
| 404 | 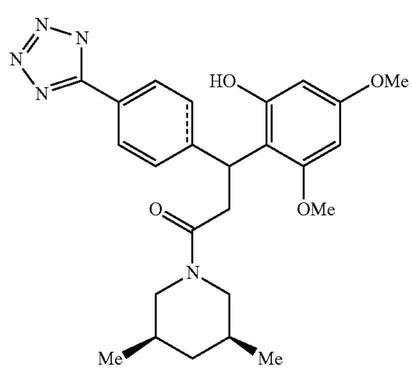 | 465.56 |
| 405 | | 443.50 |
| 406 | | 518.63 |
| 407 | | 475.97 |
| 408 | | 431.47 |

TABLE 1C-continued

More Additional Compounds of the Invention

| Compd # | Structure | MW (Calcd) |
|---|---|---|
| 409 | 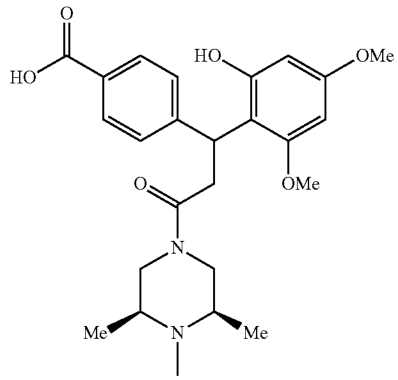 [SMILES: COc1cc(O)c(C(CC(=O)N2C[C@@H](C)N(C)[C@@H](C)C2)c2ccc(C(=O)O)cc2)c(OC)c1] | 456.54 |
| 410 | 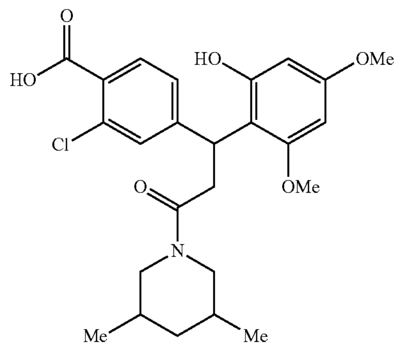 [SMILES: COc1cc(O)c(C(CC(=O)N2CC(C)CC(C)C2)c2ccc(C(=O)O)c(Cl)c2)c(OC)c1] | 475.97 |
| 411 | 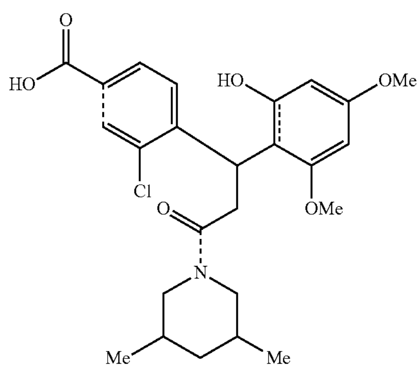 | 475.97 |
| 412 | 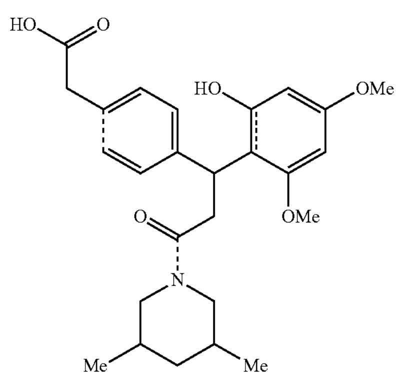 | 455.56 |
| 413 | | 465.56 |
| 414 | | 443.50 |
| 415 | | 518.63 |
| 416 | | 475.97 |

TABLE 1C-continued

More Additional Compounds of the Invention

| Compd # | Structure | MW (Calcd) |
|---|---|---|
| 417 | 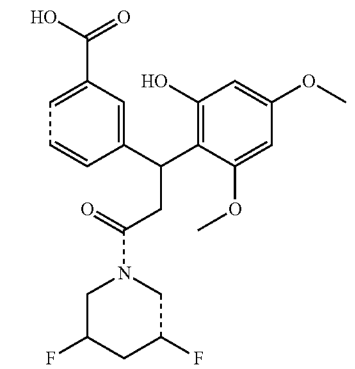 | 449.46 |
| 418 | 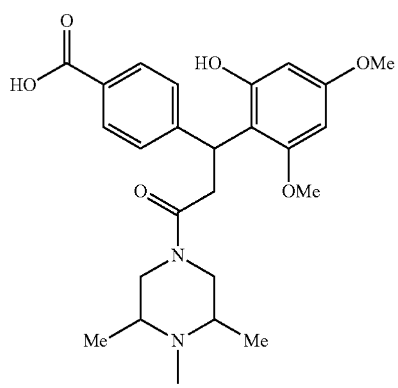 | 456.54 |

Th17 Assay
Effects of Compound Derivatives at Various Concentrations on Mouse Th17 Polarization Percentage of DMSO treated IL-17a producing cells was set at 100. Naive mouse CD4 T cells (CD25⁻, CD62L⁺, and CD44$^{low-int}$) were sorted and cultured with CD3/CD28 stimulatory antibodies in the presence of TGFβ (0.1 ng/ml) and IL6 (20 ng/ml). Compounds were added on Day 1 and cells were analyzed on Day 4. For intracellular cytokine staining, cells were incubated for 5 h with phorbol ester (50 ng/ml; Sigma), ionomycin (500 ng/ml; Sigma) and GolgiStop (BD). When needed, surfaces were stained by incubation for 15 min on ice with PECy7-conjugated CD4 (BD Biosciences). The Cytofix/Cytoperm buffer set (BD) was used for intracellular staining. Cells were fixed and made permeable for 30 min on ice and were stained for 30 min on ice in permeabilization buffer with Alexa647-conjugated anti-IL17a (eBioscience) and PE-conjugated anti-IFNg (eBioscience). An LSR II (BD Biosciences) and FlowJo software (Tree Star) were used for flow cytometry. RORg IC$_{50}$ value acquired from the S2 cell reporter assay is listed for comparison.

A number of representative amido compounds of this invention were or can be tested for their Th17 inhibitory activity. The exemplary amido compounds of the invention along with their Th17 and S2 RORg IC$_{50}$ values, as determined using conventional methods to those skilled in the art, are listed below in Table 2. For the purpose of Table 2, the IC$_{50}$ values are expressed as follows:
++++ compound exhibited TH17 IC$_{50}$<1 µM
+++ compound exhibited TH17 IC$_{50}$ 1-10 µM
++ compound exhibited TH17 IC$_{50}$ 11-20 µM
+ compound exhibited TH17 IC$_{50}$>20 µM
**** compound exhibited RORg IC$_{50}$<1 µM
*** compound exhibited RORg IC$_{50}$ 1-10 µM
** compound exhibited RORg IC$_{50}$ 11-20 µM
* compound exhibited RORg IC$_{50}$>20 µM

TABLE 2

Th17 and RORγ S2 Cell IC$_{50}$ values for Exemplary Compounds

| ID | Compd ID | Th 17 IC$_{50}$ µM | S2 cell RORg IC$_{50}$ µM |
|---|---|---|---|
| NCGC00238427 | RC1 | +++ | **** |
| NCGC00242624 | 99 | +++ | **** |
| NCGC00242626 | 101 | + | *** |

Figure 2:
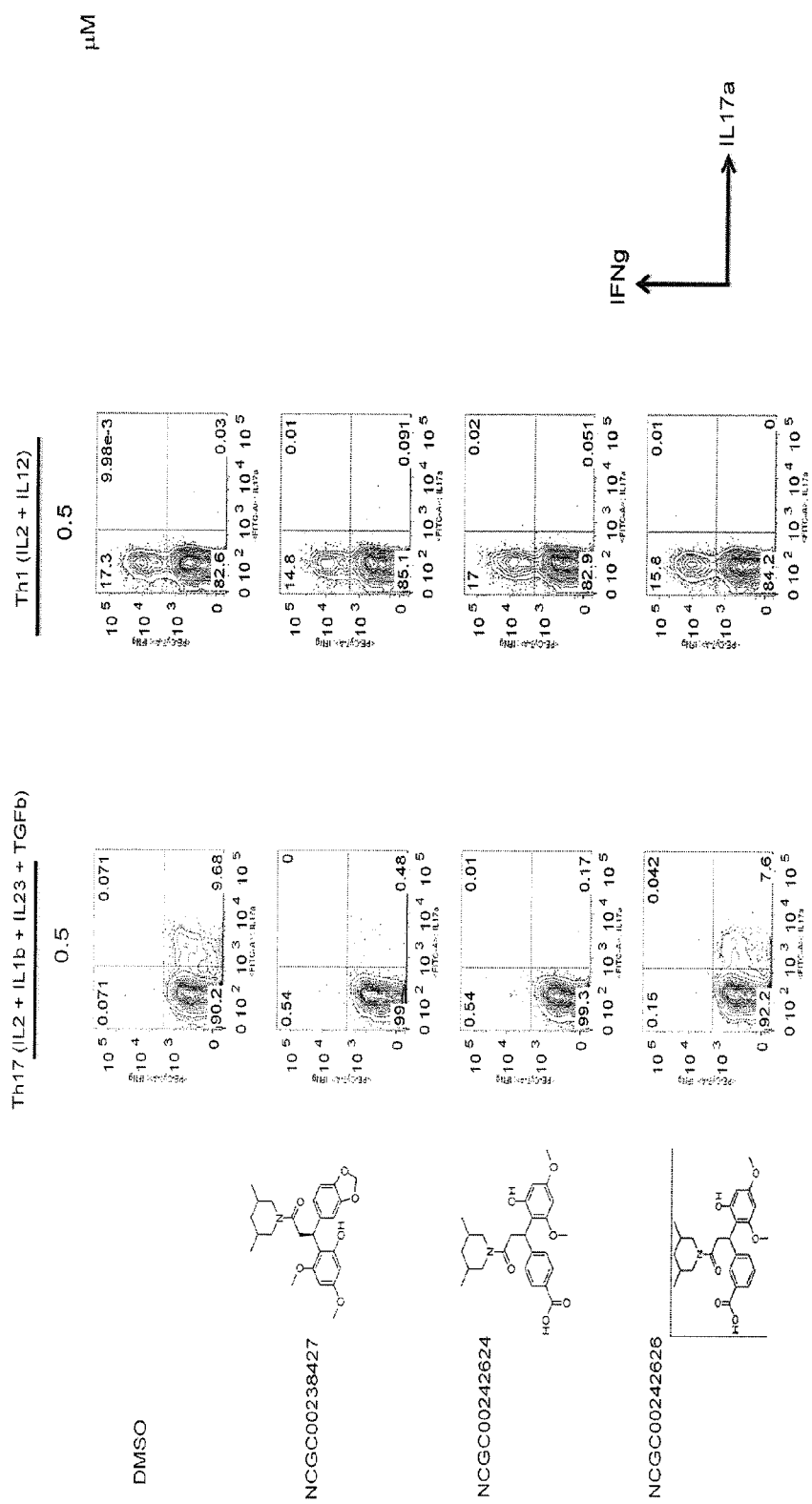
FIG. 2 shows FACS plot analyses revealing that NCGC00242624 and NCGC00238427 selectively suppress human Th17, but not human Th1, cell differentiation. Compound NCGC00242626 serves as a negative control along with the carrier control DMSO, neither of which exhibits the ability to suppress human Th17 or Th1 cell differentiation.

FIG. 1 shows FACS plot analyses demonstrating that NCGC00242624 (ID 99) and NCGC00238427 (at the indicated concentrations) suppress mouse Th17 cell differentiation, as measured by IL17a production. As shown in FIG. 2, NCGC00242624 suppresses human Th17 cell differentiation to a degree similar to that of NCGC00238427 (RC1).

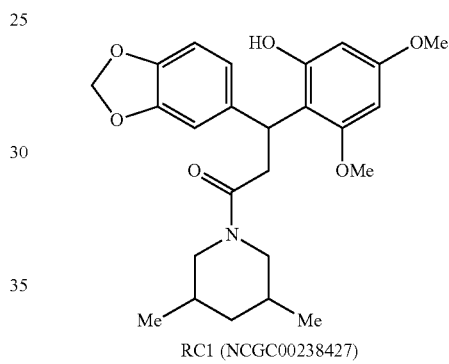

RC1 (NCGC00238427)

With respect to the methodological details pertaining to FIG. 1, naive CD4 T cells (CD25⁻, CD62L⁺, and CD44$^{low-int}$) were sorted and cultured with CD3/CD28 stimulatory antibodies in the presence of TGFβ (0.1 ng/ml) and IL6 (20 ng/ml). Compounds were added on Day 1 and cells were analyzed on Day 4. For intracellular cytokine staining, cells were incubated for 5 h with phorbol ester (50 ng/ml; Sigma), ionomycin (500 ng/ml; Sigma) and GolgiStop (BD). The Cytofix/Cytoperm buffer set (BD) was used for intracellular staining. Cells were fixed and made permeable for 30 min on ice and were stained for 30 min on ice in permeabilization buffer with Alexa647-conjugated anti-IL17a (eBioscience) and PE-conjugated anti-IFNγ (eBioscience). An LSR II (BD Biosciences) and FlowJo software (Tree Star) were used for flow cytometry.

FIG. 2 shows FACS plot analyses demonstrating that treatment with either 0.5 NCGC00242624 (ID 99) or NCGC00238427 selectively suppresses human Th17 cell differentiation. FIG. 2 also reveals that treatment with either 0.5 µM NCGC00242624 or NCGC00238427 does not inhibit Th1 cell differentiation, as measured by IFNγ production, from naive CD4 T cells. These results suggest that NCGC00242624 and NCGC00238427 do not inhibit general T cell proliferation or cytokine production. For Th1 differentiation, IL12 (10 ng/ml) and IL2 (100 U/ml) were added to naive CD4 T cell cultures instead of TGFβ and IL6.

FIG. 3 shows FACS plot analyses revealing that treatment with either 0.5 µM NCGC00242624 or NCGC00238427 selectively inhibits RORγt overexpression dependent IL17a production in human CD4 T cells. RORα overexpression dependent IL17a production in human CD4 T cells is, however, unaffected by treatment with either 0.5 μM NCGC00242624 or NCGC00238427. These results demonstrate that the effect of these compounds is selective for RORγt dependent human Th17 cell differentiation. Briefly, CD3+ CD4+ CD45RA+ naive human T cells were isolated from peripheral blood derived from healthy donors. The naive T cells were cultured in XVIVO-20 (Lonza) medium for 7 days in the presence of IL2 and stimulatory CD3 and CD28 antibodies. Cells were infected with lentivirus encoding human RORα or RORγ and compound or DMSO was added on day 2. FACS plot analysis is shown after gating on GFP expressing (virus infected) cells.

Half-life in Human Liver Microsomes (HLM)

Test compounds (1 μM) are incubated with 3.3 mM $MgCl_2$ and 0.78 mg/mL HLM (HL101) in 100 mM potassium phosphate buffer (pH 7.4) at 37° C. on the 96-deep well plate. The reaction mixture is split into two groups, a non-P450 and a P450 group. NADPH is only added to the reaction mixture of the P450 group. An aliquot of samples of the P450 group is collected at 0, 10, 30, and 60 min time points, where the 0 min time point indicated the lime at which NADPH is added into the reaction mixture of the P450 group. An aliquot of samples of non-P450 group is collected at −10 and 65 min time points. Collected aliquots are extracted with acetonitrile solution containing an internal standard. The precipitated protein is spun down in centrifuge (2000 rpm, 15 min). The compound concentration in supernatant is measured by LC/MS/MS system.

The half-life value is obtained by plotting the natural logarithm of the peak area ratio of compounds/internal standard versus time. The slope of the line of best fit through the points yields the rate of metabolism (k). This is converted to a half-life value using following equations:

Half-life=ln 2/k

The results of the tests and corresponding $t_{1/2}$ values are set forth in Table 3, below.

TABLE 3

Half Life ($t_{1/2}$) of Exemplary Compounds

| Sample ID | Compd # | Structure | % Remaining @ 60 min | $CL_{int}$ (uM/Min/mg proteins) | $t_{1/2}$ (min) |
|---|---|---|---|---|---|
| Verapamil | | 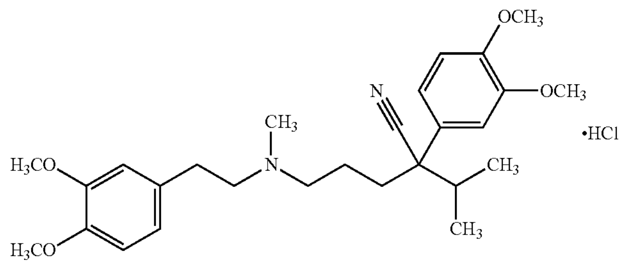 [SMILES: COc1ccc(CCN(C)CCCC(C#N)(c2ccc(OC)c(OC)c2)C(C)C)cc1OC ; Cl] | 16.49 | 62.8 | 22.1 |
| NCGC00242624 | 99 | 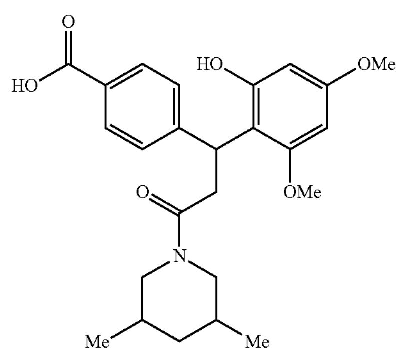 [SMILES: COc1cc(O)c(C(CC(=O)N2CC(C)CC(C)C2)c2ccc(C(=O)O)cc2)c(OC)c1] | 51.36 | 21.6 | 64.2 |
| NCGC00242637 | 141 | 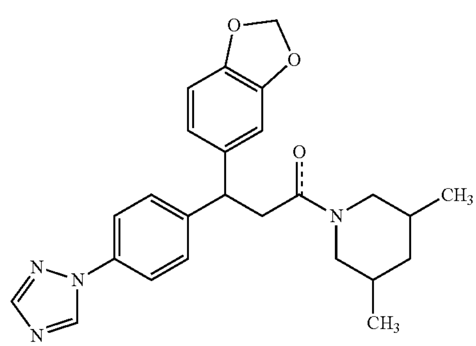 | 9.02 | 107.8 | 12.9 |

TABLE 3-continued

Half Life ($t_{1/2}$) of Exemplary Compounds

| Sample ID | Compd # | Structure | % Remaining @ 60 min | $CL_{int}$ (uM/Min/mg proteins) | $t_{1/2}$ (min) |
|---|---|---|---|---|---|
| NCGC00242649 | 150 | 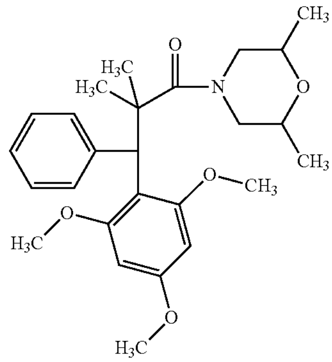 [SMILES: COc1cc(OC)c(C(c2ccccc2)C(C)(C)C(=O)N2CC(C)OC(C)C2)c(OC)c1] | 6.79 | 173.2 | 8 |
| NCGC00242657 | 157 | 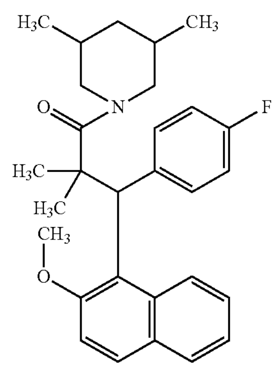 [SMILES: COc1ccc2ccccc2c1C(c1ccc(F)cc1)C(C)(C)C(=O)N1CC(C)CC(C)C1] | 6.78 | 200.8 | 6.9 |

The above stability data shows that the compounds of the present invention, ID 99 and 141, have better or improved stability over the compounds with IDs 150 and 157. The compound 99 also showed improved stability with respect to verapamil.

From the foregoing description, various modifications and changes in the compositions and methods of this invention will occur to those skilled in the art. All such modifications coming within the scope of the appended claims are intended to be included therein.

All publications, including but not limited to patents and patent applications, cited in this specification are herein incorporated by reference as if each individual publication were specifically and individually indicated to be incorporated by reference herein as though fully set forth.

The chemical names of compounds of invention given in this application are generated using Open Eye Software's Lexichem naming tool, Symyx Renassance Software's Reaction Planner or MDL's ISIS Draw Autonom Software tool and not verified. Preferably, in the event of inconsistency, the depicted structure governs.

What is claimed is:

1. A compound according to formula IIIa:

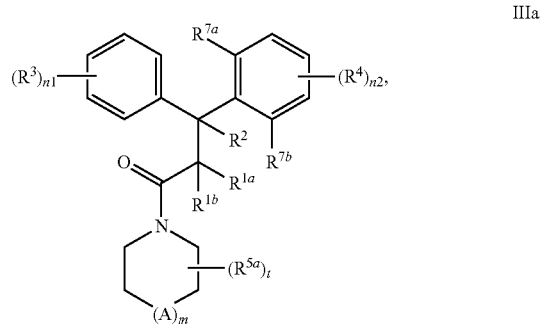

IIIa or a pharmaceutically acceptable salt, solvate or prodrug thereof;

or stereoisomers, isotopic variants and tautomers thereof;

wherein
each $R^{1a}$ and $R^{1b}$ is independently H, substituted or unsubstituted $C_1$-$C_6$ alkyl, or CN, or $R^{1a}$ and $R^{1b}$ joined together to form cycloalkyl ring;
$R^2$ is H, substituted or unsubstituted $C_1$-$C_6$ alkyl, or aryl; or one of $R^{1a}$ and $R^{1b}$ is joined to the C of $CR^2$ to form a cyclopropyl ring; or $R^2$ is joined to the C of $CR^{1a}R^{1b}$ to form a cyclopropyl ring;
each $R^3$ and $R^4$ is independently selected from H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol; or any two adjacent $R^3$ groups, or any two adjacent $R^4$ groups may join together to form a substituted or unsubstituted carbocyclic or heterocyclic ring;
n1 is 1, 2, 3, 4 or 5;
n2 is 1, 2, or 3;
A is $CR^{8a}R^{8b}$, $NR^{8a}$, O, or S; m is 0 or 1;
each $R^{5a}$ is alkyl, substituted alkyl, halo, haloalkyl, hydroxyalkyl, aryl, heteroaryl, CN, alkoxyalkyl, amido, hydroxyl, alkoxy or substitituted alkoxy; and t is 0, 1, 2, or 3;
$R^{7a}$ is H, OH, substituted or unsubstituted alkyl, substituted or unsubstituted alkoxy, substituted or unsubstituted acyl, substituted or unsubstituted acylamino, substituted or unsubstituted alkylamino, substituted or unsubstituted alkythio, substituted or unsubstituted alkoxycarbonyl, substituted or unsubstituted alkylarylamino, substituted or unsubstituted amino, substituted or unsubstituted arylalkyl, sulfo, substituted sulfo, substituted sulfonyl, substituted sulfinyl, substituted sulfanyl, substituted or unsubstituted aminosulfonyl, substituted or unsubstituted alkylsulfonyl, substituted or unsubstituted arylsulfonyl, azido, substituted or unsubstituted carbamoyl, carboxyl, cyano, substituted or unsubstituted aryl, substituted or unsubstituted heteroaryl, substituted or unsubstituted cycloalkyl, substituted or unsubstituted heterocycloalkyl, substituted or unsubstituted dialkylamino, halo, nitro, and thiol;
$R^{7b}$ is $R^4$; or any two adjacent $R^4$ and $R^{7b}$ groups may join together to form a substituted or unsubstituted carbocyclic or heterocyclic ring; and
each $R^{8a}$ and $R^{8b}$ is independently H, substituted or unsubstituted $C_1$-$C_6$ alkyl, substituted or unsubstituted aryl, or substituted or unsubstituted heteroaryl;
provided that
i) at least one $R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl;
and wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;
ii) when $R^3$ is $CONR^{3a}R^{3b}$, $R^{3a}$ and $R^{3b}$ joined together to form a morpholino ring, m is 1, and A is O; then $R^{7a}$ is other than H;
iii) when the compound is

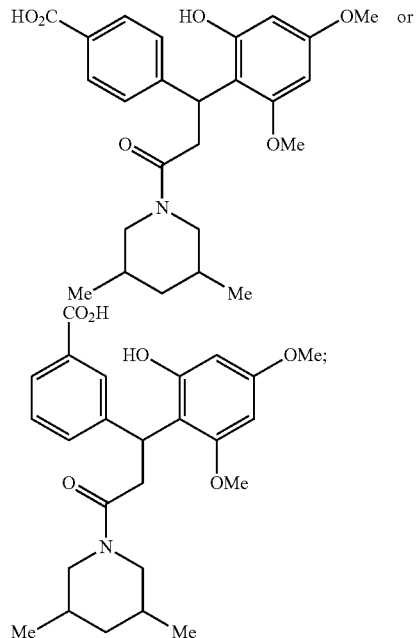

then the compound is in the form of a sodium, potassium, calcium, or ammonium salt; and
iv) the compound is other than

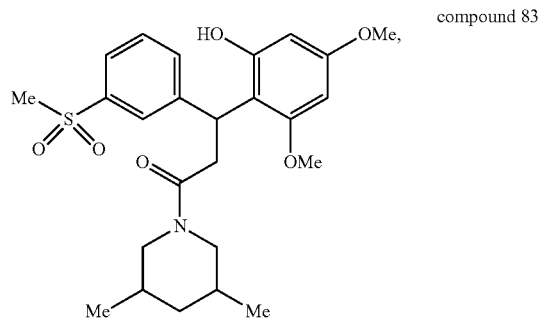

compound 83

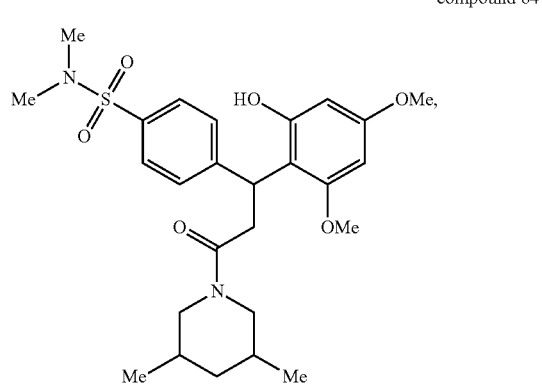

compound 84

-continued compound 95

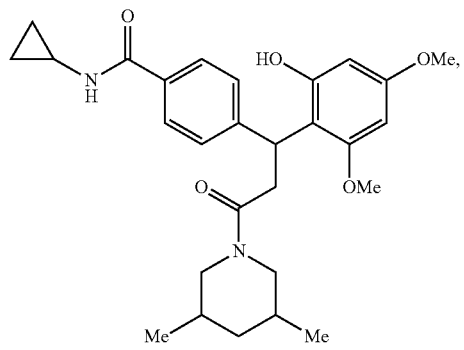

compound 100

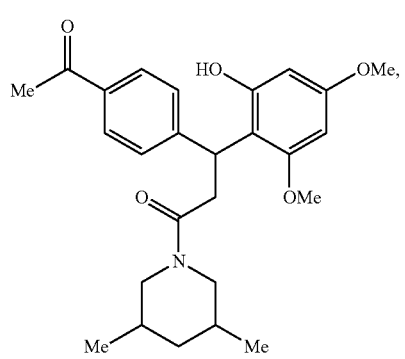

compound 111

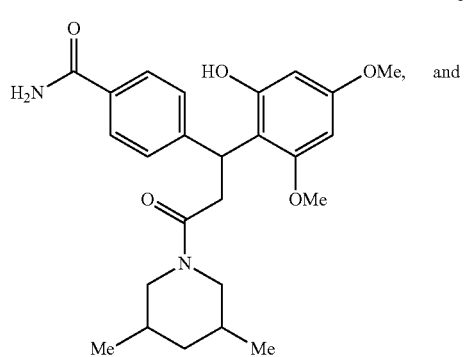

compound 139

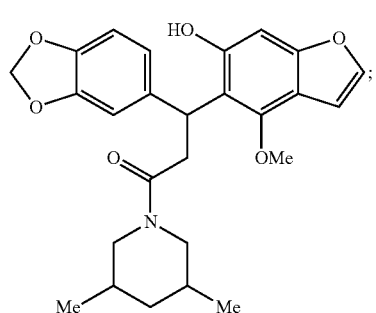

or a pharmaceutically acceptable salt, solvate or prodrug thereof;
or stereoisomers, isotopic variants and tautomers thereof.

2. The compound according to claim 1, wherein
each of $R^{7a}$ and $R^{7b}$ is independently OH, substituted or unsubstituted alkyl, substituted or unsubstituted alkoxy, CN, halo, amido, or haloalkyl; or
each of $R^{7a}$ and $R^{7b}$ is independently halo, $C_1$-$C_6$ alkyl, CN, OH, or $C_1$-$C_6$ alkoxy; or each of $R^{7a}$ and $R^{7b}$ is independently Cl, F, Me, $CF_3$, CN, OH, or OMe; or
one of $R^{7a}$ and $R^{7b}$ is OH; and the other is alkoxy; or
each of $R^{7a}$ and $R^{7b}$ is OH or alkoxy; or
one of $R^{7a}$ and $R^{7b}$ is OH; and the other is OMe.

3. The compound according to claim 1, wherein $R^{1a}$ and $R^{1b}$ is independently H, CN, or Me; or
each of $R^{1a}$ and $R^{1b}$ is H or Me; or
one of $R^{1a}$ and $R^{1b}$ is H; and the other is CN.

4. The compound according to claim 1, wherein $R^4$ is H, alkyl, substituted alkyl, halo, haloalkyl, hydroxyalkyl, alkoxyalkyl, amido, hydroxyl, cyano, or alkoxy; or
$R^4$ is H, halo, $C_1$-$C_6$ alkyl, CN, OH, or $C_1$-$C_6$ alkoxy; or
$R^4$ is H, Cl, F, Me, $CF_3$, CN, OH, or OMe.

5. The compound according to claim 1, wherein the compound is according to formula IVa, IVb, IVe, or IVf:

IVa
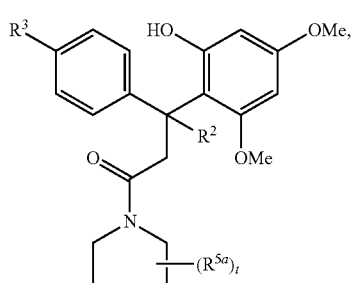

IVb
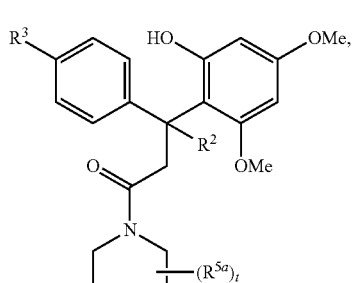

IVe
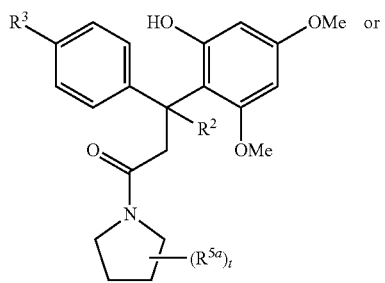

-continued

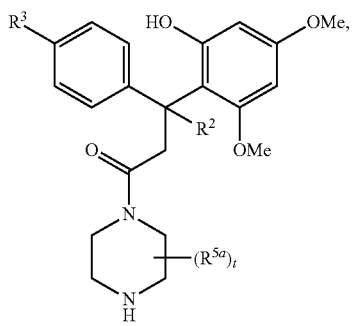

IVf or a pharmaceutically acceptable salt, solvate or prodrug thereof;

or stereoisomers, isotopic variants and tautomers thereof;

and wherein $R^2$, $R^5$, and $R^6$ are as in claim 1;

$R^3$ is selected from $CO_2H$, $CH_2CO_2H$, $COR^{3a}$, $CONR^{3a}R^{3b}$, $SO_3H$, $SOR^{3a}$, $SO_2R^{3a}$, and heteroaryl; wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl; or $R^{3a}$ and $R^{3b}$ may join together to form a substituted or unsubstituted heterocyclic ring;

each $R^{5a}$ is alkyl, substituted alkyl, halo, haloalkyl, hydroxyalkyl, aryl, heteroaryl, CN, alkoxyalkyl, amido, hydroxyl, alkoxy or substitituted alkoxy; t is 0, 1, 2, or 3;

provided that i) when the compound is

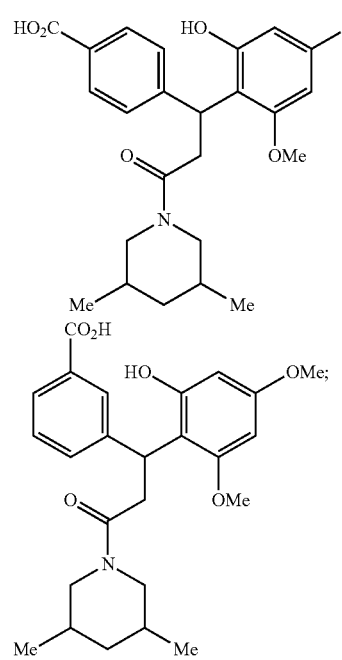

then the compound is in the form of a sodium, potassium, calcium, or ammonium salt; and ii) the compound is other than

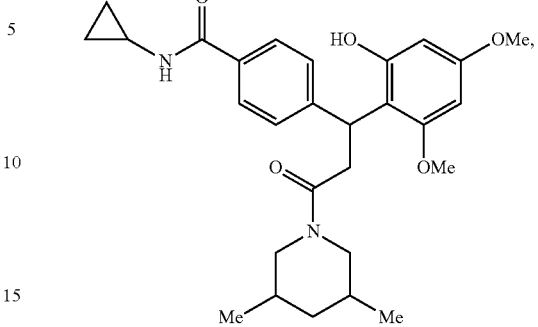

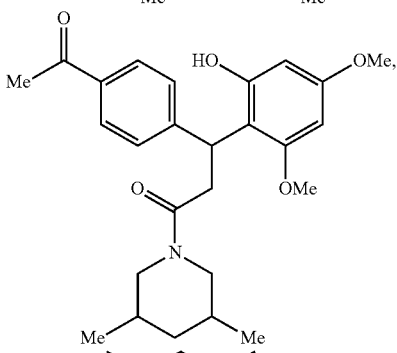

6. The compound according to claim 1, wherein $R^3$ is $CO_2H$, $SO_3H$, or $CH_2CO_2H$; or $R^3$ is pyrrolyl, furanyl, thienyl, imidazolyl, oxazolyl, thiazolyl, pyrazolyl, isoxazolyl, triazolyl, oxadiazolyl, thiadiazolyl, and tetrazolyl; or $R^3$ is 1,3,4-triazolyl or tetrazol-5-yl; or $R^3$ is $CONR^{3a}R^{3b}$; wherein each $R^{3a}$ and $R^{3b}$ is independently selected from H, substituted or unsubstituted alkyl, substituted or unsubstituted cycloalkyl, substituted or unsubstituted aryl, and substituted or unsubstituted heteroaryl.

7. The compound according to claim 1, wherein $R^2$ is H, Me, OH or Ph.

8. The compound according to claim 1, wherein t is 0; or t is 1 or 2; and each $R^{5a}$ is independently OH, Ph, benzyl, or Me; or t is 1; and $R^{5a}$ is Me, Et, n-Pr, or n-Bu; or t is 1; and $R^{5a}$ is 3-Me, 3-Et, 3-n-Pr, or 3-n-Bu; or t is 2; and one $R^{5a}$ is 3-Me and the other is 5-Me.

9. The compound according to claim 1, wherein the compound is according to formula VIIa, VIIb, VIIc, VIId, VIIe, or VIIf:

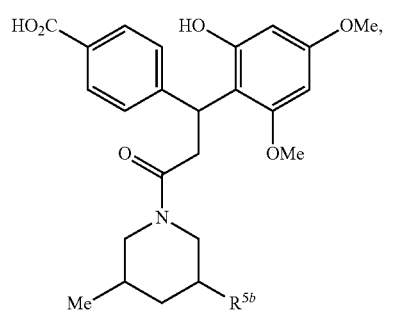

VIIa

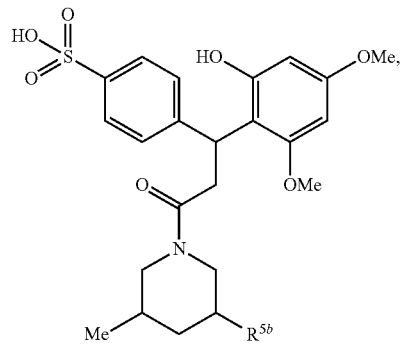

VIIb

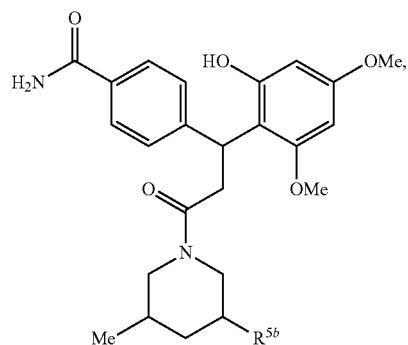

VIIc

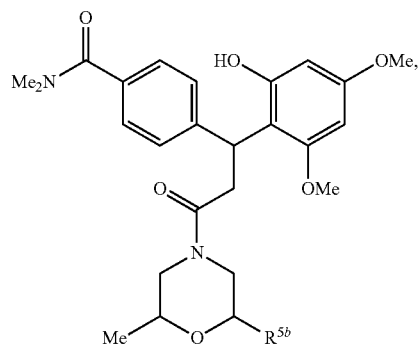

VIId

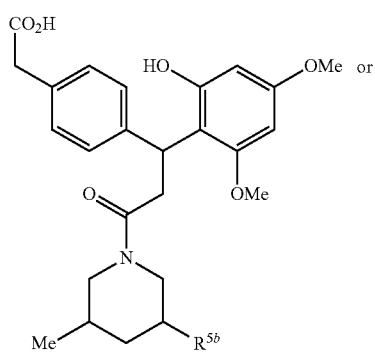

VIIe

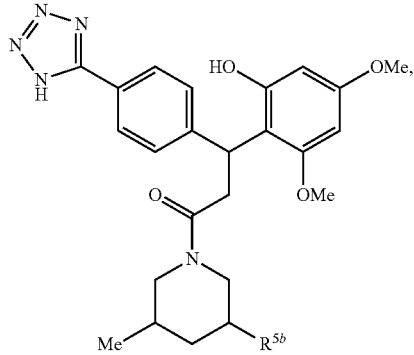

VIIf and wherein $R^{5b}$ is H or Me;

or a pharmaceutically acceptable salt, solvate or prodrug thereof;

or stereoisomers, isotopic variants and tautomers thereof.

10. The compound according to claim 1, wherein the compound is according to formula VIIIa, VIIIb, or VIIIc:

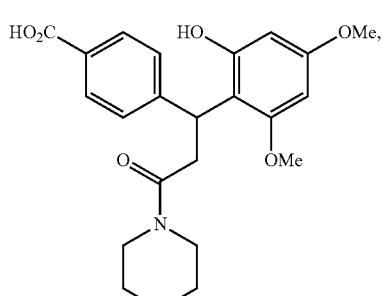

VIIIa

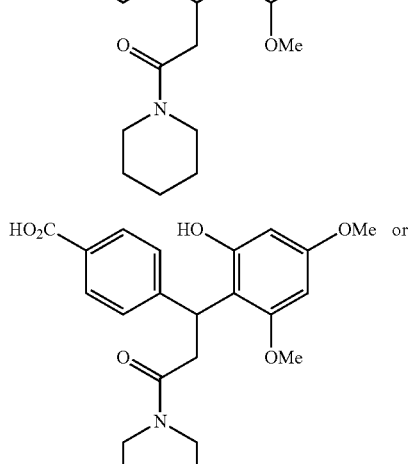

VIIIb

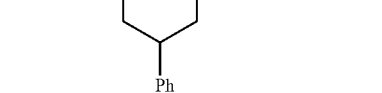

-continued

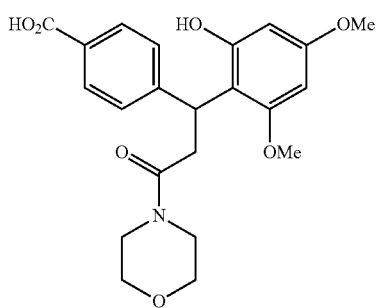

VIIIc or a pharmaceutically acceptable salt, solvate or prodrug thereof;

or stereoisomers, isotopic variants and tautomers thereof.

11. The compound according to claim 1, wherein the compound is according to formula IXa, IXb, or IXc:

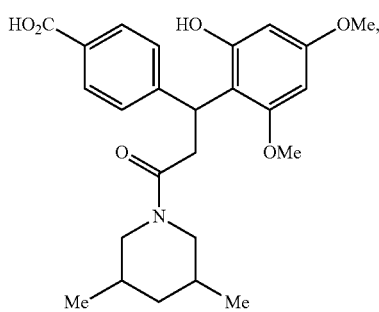

IXa

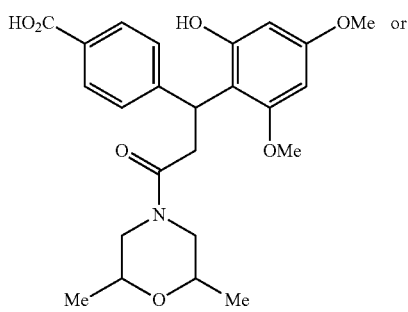

IXb

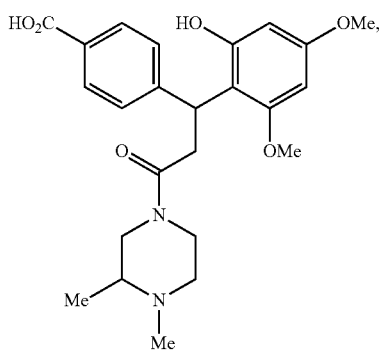

IXc or a pharmaceutically acceptable salt, solvate or prodrug thereof;

or stereoisomers, isotopic variants and tautomers thereof.

12. A compound selected from

| Compd # | Structure |
|---|---|
| 202 | 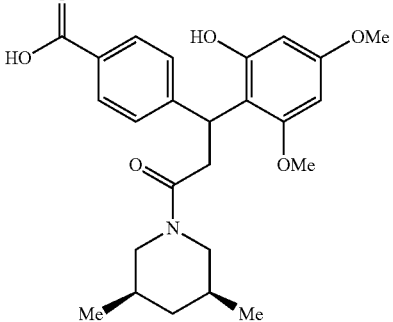 |
| 401 | 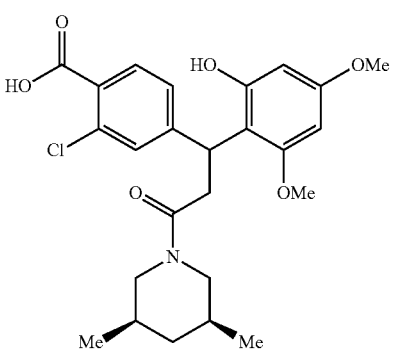 |
| 402 | 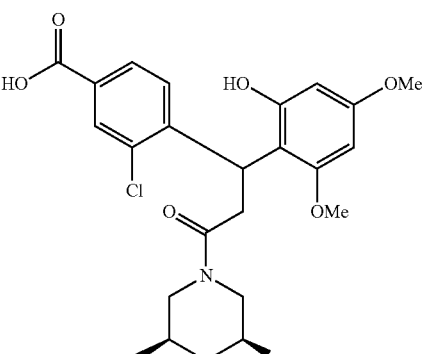 |
| 403 | 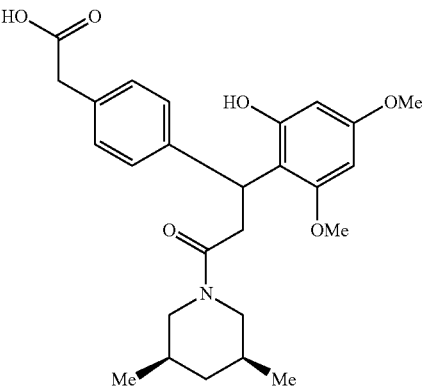 [SMILES: COc1cc(O)c(C(CC(=O)N2C[C@H](C)C[C@H](C)C2)c2ccc(CC(=O)O)cc2)c(OC)c1] |

125
-continued

| Compd # | Structure |
|---|---|
| 404 | 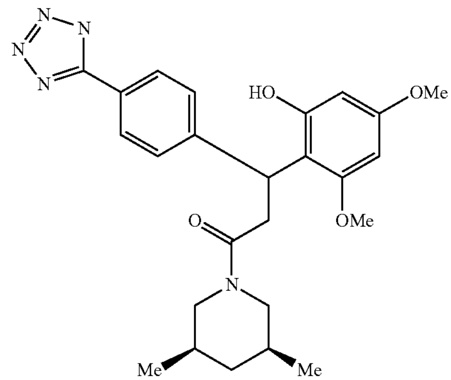 [SMILES: COc1cc(O)c(C(CC(=O)N2C[C@H](C)C[C@H](C)C2)c2ccc(-c3nnn[nH]3)cc2)c(OC)c1] |
| 405 | 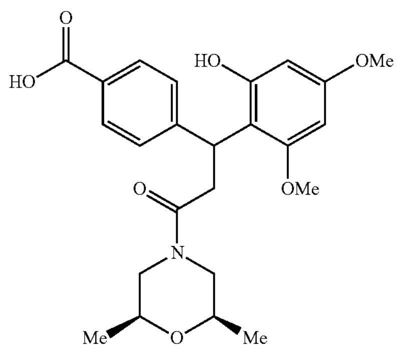 |
| 407 | 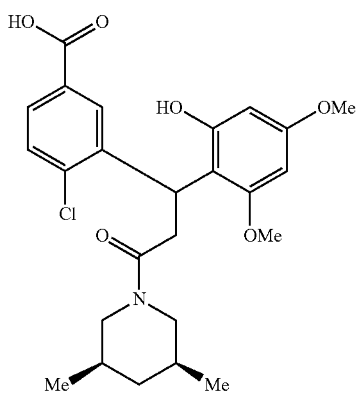 [SMILES: COc1cc(O)c(C(CC(=O)N2C[C@H](C)C[C@H](C)C2)c2cc(C(=O)O)ccc2Cl)c(OC)c1] |
| 408 | 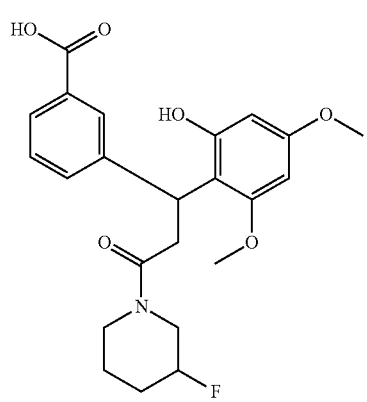 [SMILES: COc1cc(O)c(C(CC(=O)N2CCCC(F)C2)c2cccc(C(=O)O)c2)c(OC)c1] |

126
-continued

| Compd # | Structure |
|---|---|
| 409 | 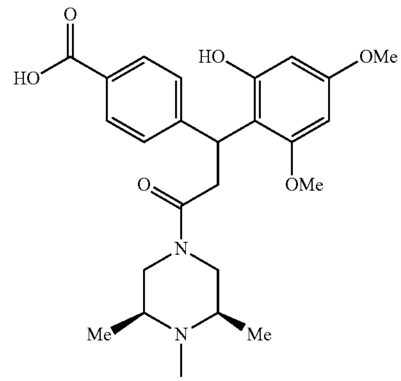 [SMILES: COc1cc(O)c(C(CC(=O)N2C[C@@H](C)N(C)[C@@H](C)C2)c2ccc(C(=O)O)cc2)c(OC)c1] |
| 410 | 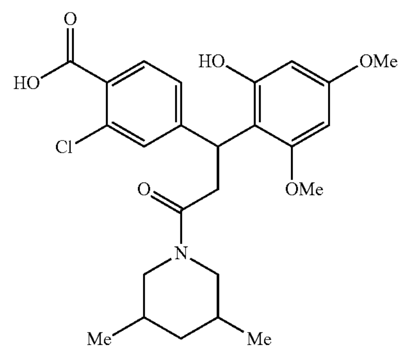 [SMILES: COc1cc(O)c(C(CC(=O)N2CC(C)CC(C)C2)c2ccc(C(=O)O)c(Cl)c2)c(OC)c1] |
| 411 | 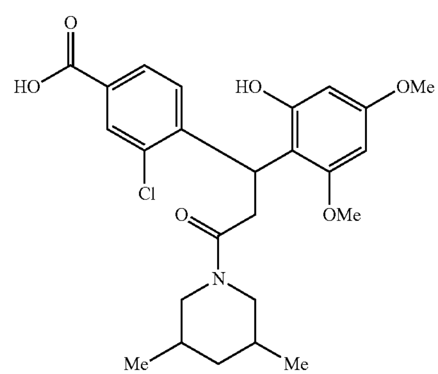 [SMILES: COc1cc(O)c(C(CC(=O)N2CC(C)CC(C)C2)c2ccc(C(=O)O)cc2Cl)c(OC)c1] |
| 412 | 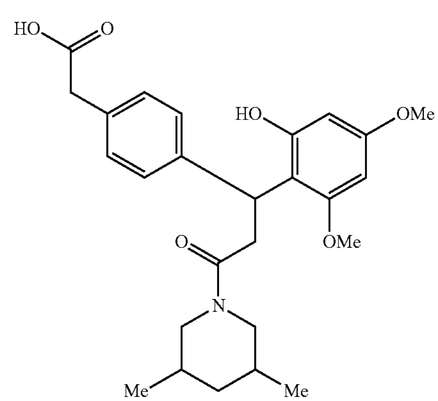 [SMILES: COc1cc(O)c(C(CC(=O)N2CC(C)CC(C)C2)c2ccc(CC(=O)O)cc2)c(OC)c1] |

| Compd # | Structure |
|---|---|
| 413 | (structure) |
| 414 | (structure) |
| 416 | (structure) |
| 417 | (structure) ; and |
| 418 | (structure) | or a pharmaceutically acceptable salt, solvate or prodrug thereof; or stereoisomers, isotopic variants and tautomers thereof.

13. A pharmaceutical composition of the compound according to either one of claim 1 or 12.

* * * * *

UNITED STATES PATENT AND TRADEMARK OFFICE
CERTIFICATE OF CORRECTION

PATENT NO. : 9,765,063 B2
APPLICATION NO. : 14/343410
DATED : September 19, 2017
INVENTOR(S) : Dan Littman et al.

It is certified that error appears in the above-identified patent and that said Letters Patent is hereby corrected as shown below:

In the Specification

At Column 1, Lines 13-16, replace:
""""This invention was made with government support under Grant Number R01A1080885 awarded by the National Institutes of Health. The Government has certain rights in the invention."""""

With:
--This invention was made with government support under grant numbers R01 AI080885 and K99 DK091508 awarded by the National Institutes of Health. The government has certain rights in the invention.--

Signed and Sealed this
Twenty-eighth Day of May, 2019

Andrei Iancu
*Director of the United States Patent and Trademark Office*